(12) United States Patent
Yang

(10) Patent No.: US 8,818,737 B2
(45) Date of Patent: Aug. 26, 2014

(54) METHODS, SYSTEMS, ALGORITHMS AND MEANS FOR DESCRIBING THE POSSIBLE CONFORMATIONS OF ACTUAL AND THEORETICAL PROTEINS AND FOR EVALUATING ACTUAL AND THEORETICAL PROTEINS WITH RESPECT TO FOLDING, OVERALL SHAPE AND STRUCTURAL MOTIFS

(75) Inventor: Jiaan Yang, Indianapolis, IN (US)

(73) Assignee: Sundia Meditech Company, Ltd., Shanghai (CN)

( * ) Notice: Subject to any disclaimer, the term of this patent is extended or adjusted under 35 U.S.C. 154(b) by 1292 days.

(21) Appl. No.: 12/524,572

(22) PCT Filed: Jan. 30, 2008

(86) PCT No.: PCT/US2008/001159
§ 371 (c)(1),
(2), (4) Date: Jul. 25, 2009

(87) PCT Pub. No.: WO2008/094547
PCT Pub. Date: Aug. 7, 2008

(65) Prior Publication Data
US 2009/0319193 A1 Dec. 24, 2009

Related U.S. Application Data

(60) Provisional application No. 60/898,529, filed on Jan. 31, 2007, provisional application No. 61/004,094, filed on Nov. 23, 2007, provisional application No. 61/062,775, filed on Jan. 29, 2008.

(51) Int. Cl.
*G01N 31/00* (2006.01)
*G01N 30/50* (2006.01)
*G06G 7/58* (2006.01)

(52) U.S. Cl.
USPC .................................. 702/27; 702/19; 703/11

(58) Field of Classification Search
CPC . G01N 33/68; G01N 2333/47; G01N 24/087; G06F 19/16; G06F 19/18; G06F 19/22; G06F 19/24; G06F 19/701; G06F 19/706
See application file for complete search history.

*Primary Examiner* — Eric S DeJong
(74) *Attorney, Agent, or Firm* — Matthias Scholl P.C.; Matthias Scholl

(57) ABSTRACT

Methods, systems, algorithms and means for describing, analyzing and predicting protein folding motifs and other structures are provided. In one aspect, the Protein Folding Shape Code (PFSC) methods, systems, algorithms and means of the present invention apply generally to all of the categories of protein analysis and description, and are especially relevant to the geometric analysis and descriptions of proteins from their respective sequences or sequence portions. In a novel approach, the present inventions render analysis with respect to the alpha carbons of five-amino acid elements of a protein, utilizing available data to derive torsion angles and pitch distances, to thereby generate a series of overlapping analysis that can be expressed by a plurality of 27 vectors. Methods, systems and algorithms of the invention can be embodied in any computing device or portion thereof, and are adaptable to describe, analyze and predict the folding and other three-dimensional aspects of the structures of biomolecules such as nucleic acids, carbohydrates and glycoproteins. As yet another advantage, the present invention is adaptable as a tool for describing the conformations of many other organic molecules, and are thus especially suitable for use in the design of drugs, and the discovery and design of molecules which are to be adapted to interact with drugs.

20 Claims, 14 Drawing Sheets

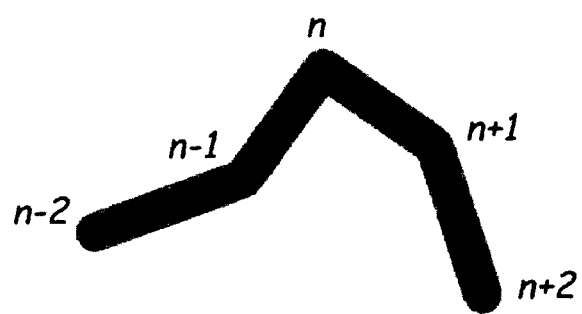
FIG. 1 Element of 5 Consecutive $C_\alpha$ Atoms from the N-Terminus to the C-Terminus

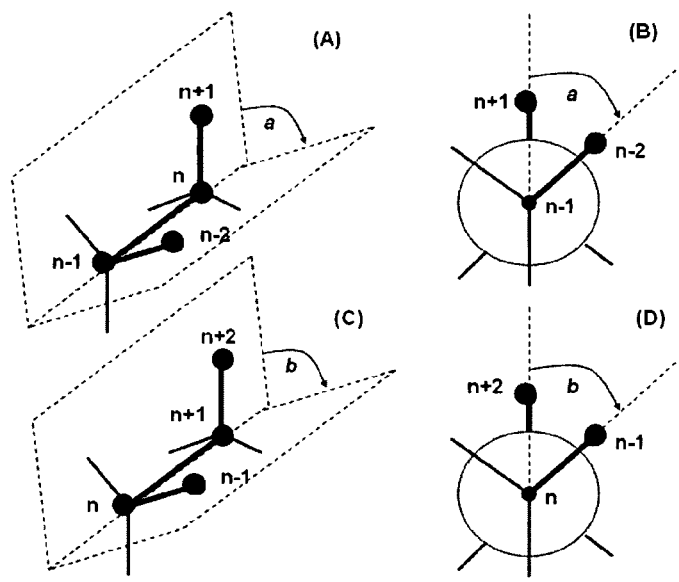

FIG. 2 Two Torsion Angles in an Element (A) The first torsion angle, $a$, is defined as the angle between the first plane, which is defined by the $C_\alpha$ atoms n-2, n-1 and n, and the second plane, which is defined by the $C_\alpha$ atoms n-1, n and n+1. (B) The side view of torsion angle $a$. (C) The second torsion angle, $b$, is defined as the angle between the second plane, which is defined by $C_\alpha$ atoms n-1, n and n+1, and the third plane, which is defined by the $C_\alpha$ n, n+1 and n+2. (D) The side view of torsion angle $b$.

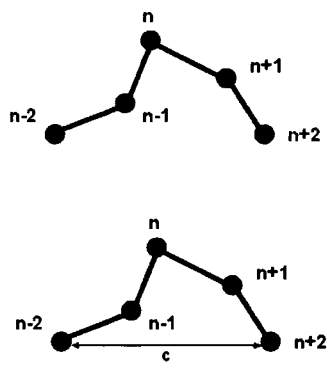
FIG. 3 Pitch Distance in an Element
Top is the ball and stick view of 5 consecutive $C_\alpha$ atoms segment. The balls represent the 5 $C_\alpha$ atoms in an element, and the sticks connect each $C_\alpha$ atoms. The $C_\alpha$ atoms are labeled as n-2, n-1, n, n+1 and n+2. The line c between n-2 and n+2 in bottom image is the pitch distance between the $C_\alpha$ atoms n-2 and n+1.

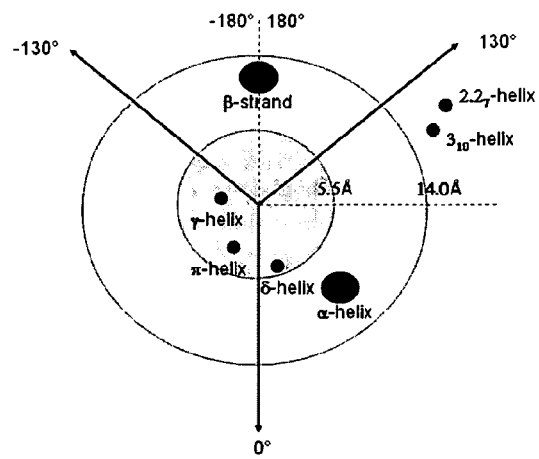

FIG. 4 Partitioning of Torsion Angles and Pitch Distance in an Element

In one embodiment, the first torsion angle and the second torsion angle are partitioned into three range values, such as 0° to 130°, >130° to 180° and -180° to -130°, and -130° to 0°; and the pitch distance is partitioned into three range values, such as 0Å to 5.5Å, > 5.5Å to 14.0Å and > 14.0Å to 20 Å. The partitioning of the two torsion angles and the pitch distance results in the identification of different folding motifs using different Protein Folding Shape Code vectors. For example, the folding motifs α-helix, β-strand, γ-helix and π-helix, δ-helix, and $3_{10}$ helix and $2.2_7$ helix fit into five different regions.

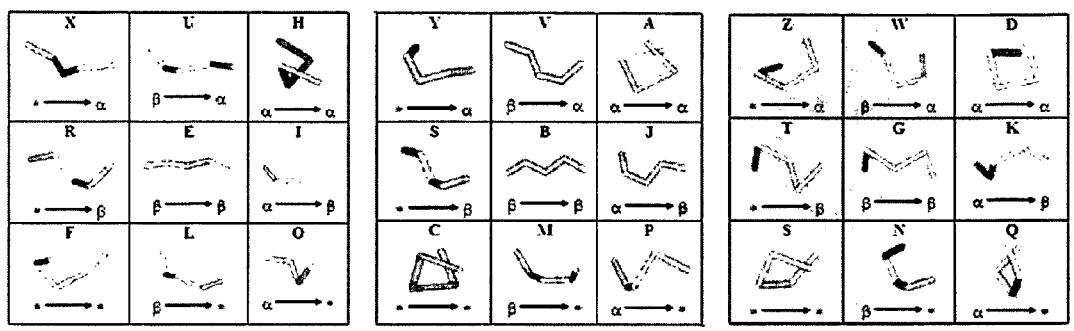

FIG. 5 27 Protein Folding Shape Code Vectors

The 27 Protein Folding Shape Code (PFSC) vectors can be represented in three blocks of nine vectors. The three blocks represent the three pitch distance value ranges; the nine vectors in each block represent the nine folding shape patterns. Each vector is simultaneously represented by a letter, a folding shape pattern, and an arrow signifying the folding characteristics at the N-terminus and the C-terminus. Under this notation of using an arrow, "α" represents a α-helix folding characteristics at the terminus, "β" represents a β-strand folding characteristics at the terminus, and "*" represents a random coil folding characteristics at the terminus.

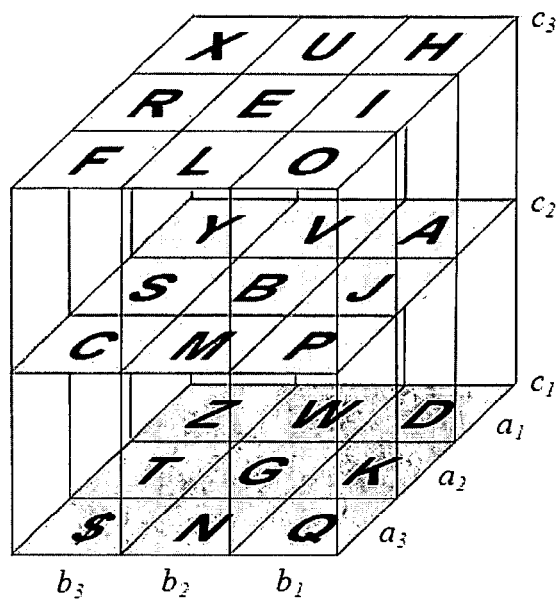

FIG. 6 Relationship of the PFSC Vectors According to Torsion Angles and Pitch Distnace The three horizontal layers represent the three pitch distance value ranges. The nine vectors in each horizontal layer represent the partitioning of each of the first and second torsion angles into three value ranges. Therefore, the nine vectors in each vertical layer belong to same torsion angle value range. Here $a_i$ is the index of the first torsion angle, $b_j$ is the index of the second torsion angel, and $c_k$ is the index of pitch distance between the first and the fifth alpha carbon atoms in an element.

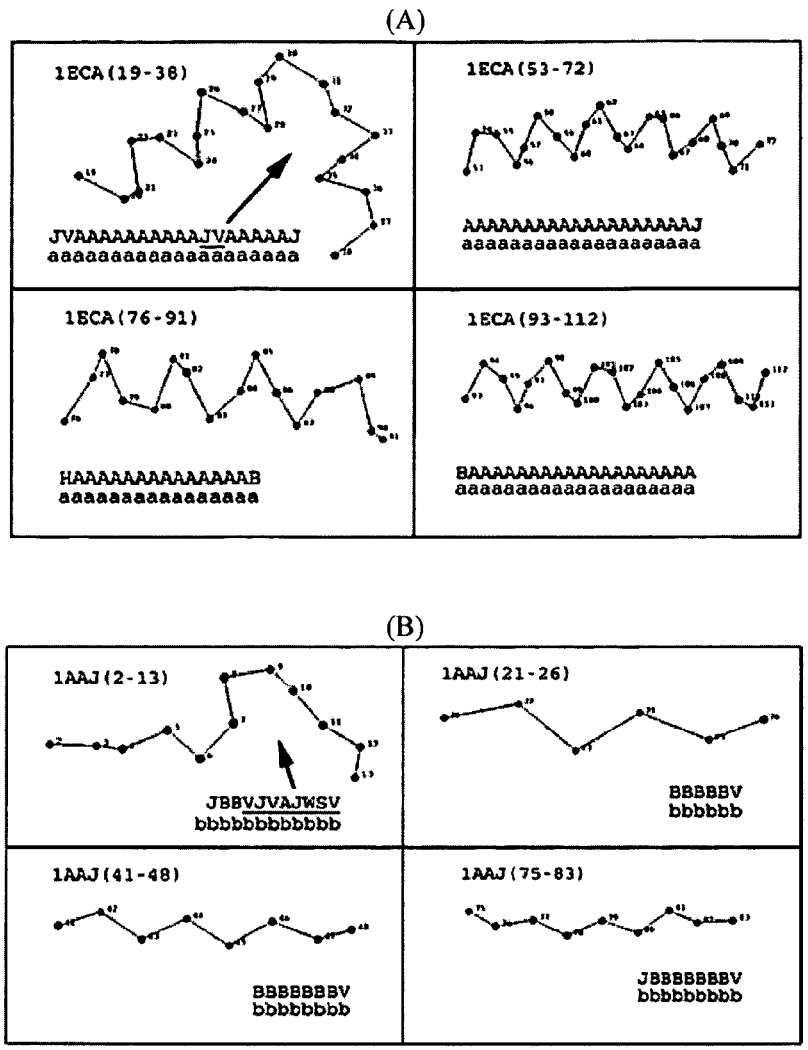

FIG. 7 Comparison of the PFSC and PDB Methods in Assigning Secondary Structures

This is a comparison of the assignment of secondary structures by the PFSC method and by the authors who submitted the protein structures to the PDB. (A) Comparison of α-helix assignments for four fragments in the protein PDB ID 1ECA. (B). Comparison of β-strand assignments for four fragments in the protein PDB ID 1AAJ. Each fragment is labeled with residue numbers. The PFSC is displayed in uppercase letters and PDB data in lowercase letters. The underlined PFSC vectors represent disruptions in the secondary structure that are not reported by the authors to the PDB.

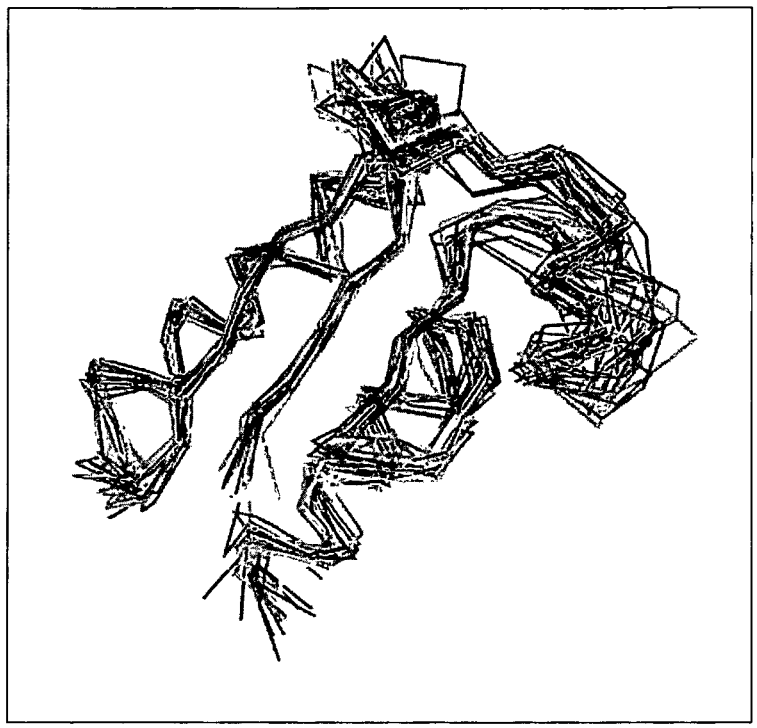
FIG. 8 The Superimposed 3D Structures of 20 Conformers of the Oxidized Form of *E. coli* Glutaredoxin (PDB ID 1EGO).
The structures are superimposed by fitting N, $C_\alpha$ and C' of the polypeptide backbones.

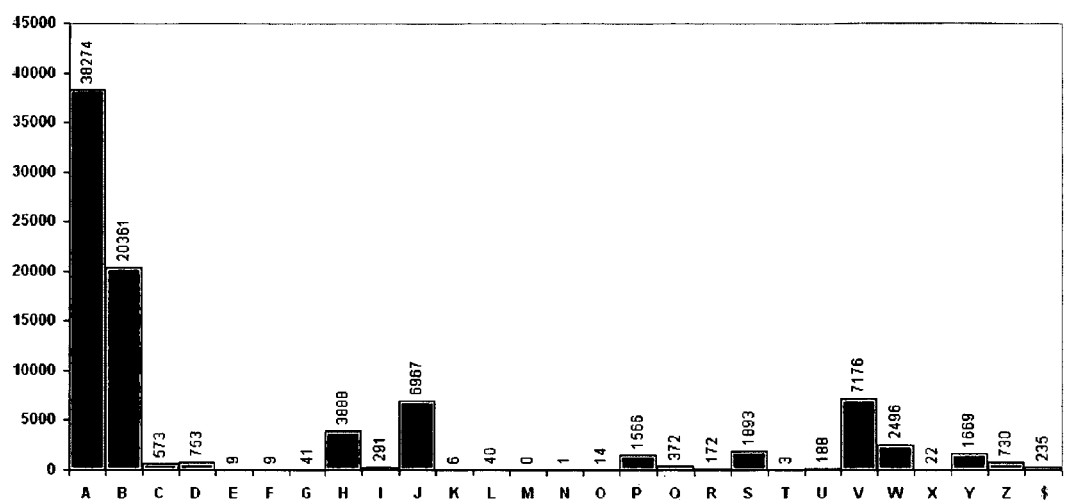
FIG. 9 Frequency of Appearance of PFSC Vectors for SALIGN Benchmark
The horizontal axis represents the 27 PFSC vectors. Each vertical bar indicates the number of appearance of the corresponding PFSC vector in the 268 protein chains for SALIGN benchmark.

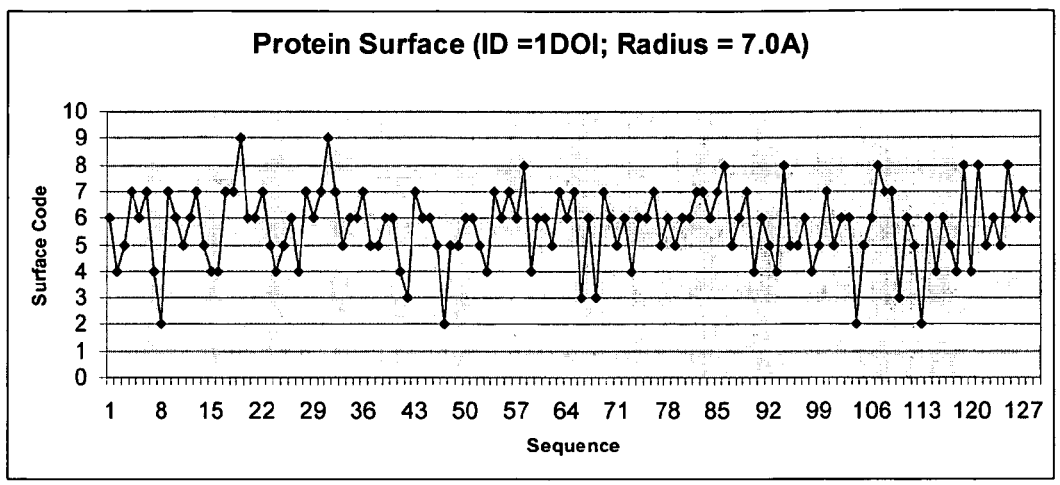
FIG. 10 Accessible Protein Folding Surface Code for the protein 1DOI
The APSC are obtained by using a sphere with radius 7.0Å. The vertical scale is the APSC: 7, 8 and 9 represent protrusions toward the outside of the surface of the sphere, 4, 5 and 6 represent the surface of the sphere, and 2 and 3 represent pockets underneath of the surface, and 0 and 1 represent inaccessible areas.

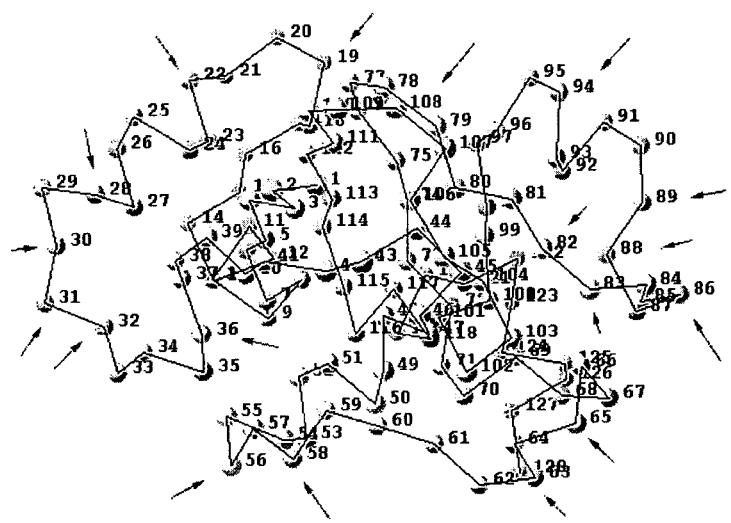
FIG. 11 Protein 1DOI Showing Protrusions from the Surface
The arrows indicate where the protrusions are with respect to the surface of a radius of 7.0Å.

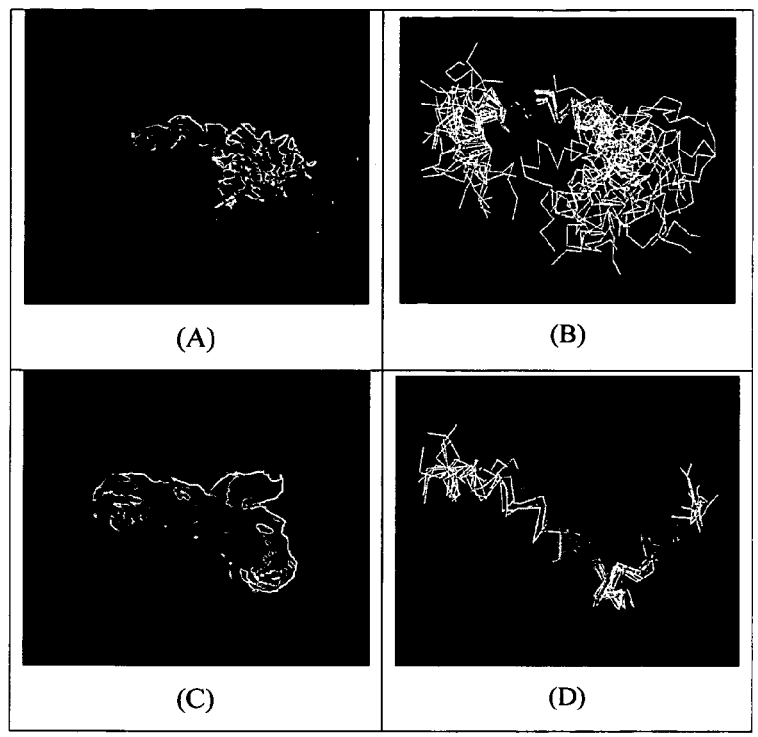

FIG. 12 Superimposed Conformers of Alzheimer Amyloid β-peptide (1-42) Peptides (A) and (B) are PDB ID 1z0q in ribbon view and carbon backbone view. (C) and (D) are PDB ID 1iyt in ribbon view and carbon backbone view. The 3D structures are determined by NMR. The structures of 1z0q are the results of 30 conformers in HFIP/H2O 30:70 (v/v) aqueous mixtures. The structures of 1iyt are the results of 10 conformers in HFIP/H2O 80:20 (v/v) aqueous mixtures.

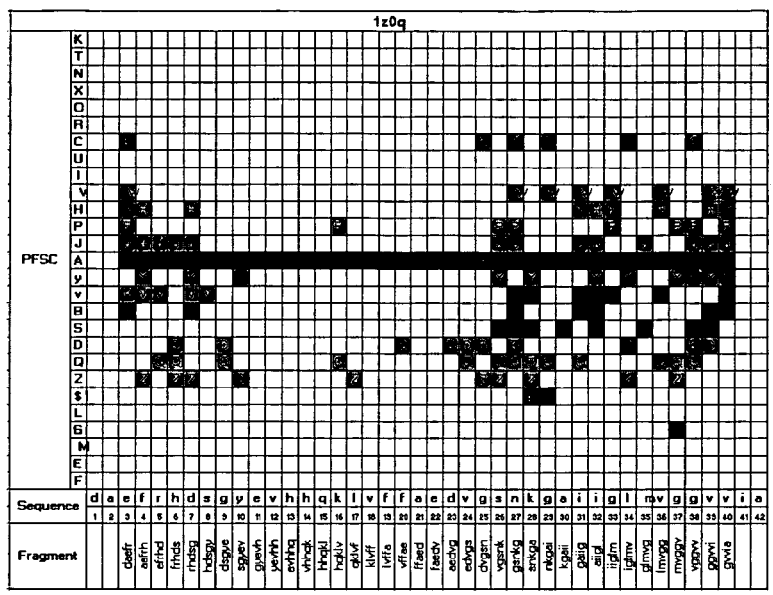
FIG. 13 UPFSM of the 30 Conformers of the Protein 1z0q
The UPFSM shows the distribution of the PFSC vectors for the 30 conformers of the protein 1z0q in HFIP/H2O 30:70 (v/v) aqueous mixtures.

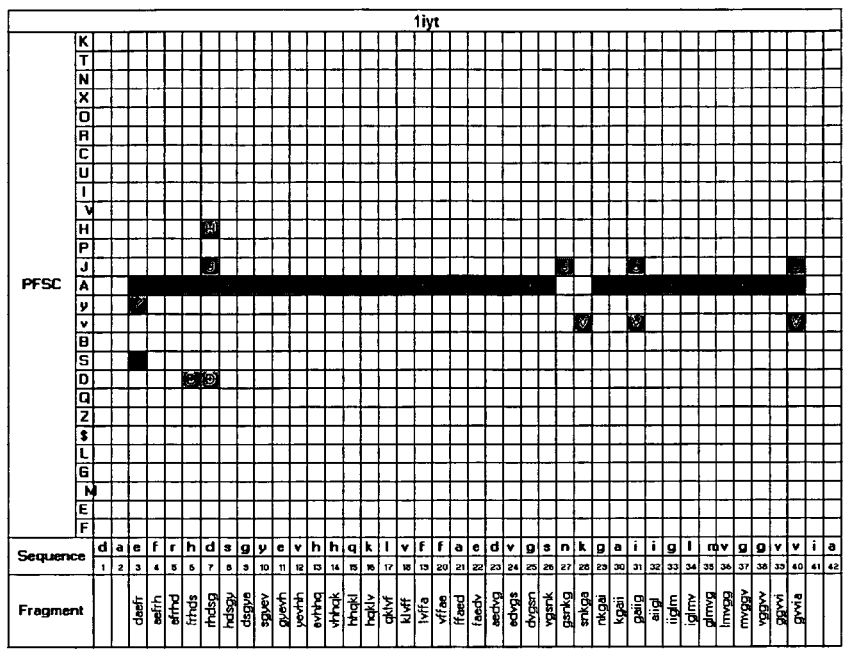
FIG. 14 UPFSM of the 30 Conformers of the Protein 1iyt
The UPFSM shows the distribution of the PFSC vectors for the 30 conformers of the protein 1iyt in HFIP/H2O 80:20 (v/v) aqueous mixtures.

SEQUENCE LISTING

```
<160> NUMBER OF SEQ ID NOS: 62

<210> SEQ ID NO 1
<211> LENGTH: 136
<212> TYPE: PRT
<213> ORGANISM: Chironomus thummi

<400> SEQUENCE: 1

Leu Ser Ala Asp Gln Ile Ser Thr Val Gln Ala Ser Phe Asp Lys Val
1               5                   10                  15

Lys Gly Asp Pro Val Gly Ile Leu Tyr Ala Val Phe Lys Ala Asp Pro
            20                  25                  30

Ser Ile Met Ala Lys Phe Thr Gln Phe Ala Gly Lys Asp Leu Glu Ser
        35                  40                  45

Ile Lys Gly Thr Ala Pro Phe Glu Thr His Ala Asn Arg Ile Val Gly
    50                  55                  60

Phe Phe Ser Lys Ile Ile Gly Glu Leu Pro Asn Ile Glu Ala Asp Val
65                  70                  75                  80

Asn Thr Phe Val Ala Ser His Lys Pro Arg Gly Val Thr His Asp Gln
                85                  90                  95

Leu Asn Asn Phe Arg Ala Gly Phe Val Ser Tyr Met Lys Ala His Thr
            100                 105                 110

Asp Phe Ala Gly Ala Glu Ala Ala Trp Gly Ala Thr Leu Asp Thr Phe
        115                 120                 125

Phe Gly Met Ile Phe Ser Lys Met
    130                 135

<210> SEQ ID NO 2
<211> LENGTH: 105
<212> TYPE: PRT
<213> ORGANISM: Paracoccus denitrificans
```

<400> SEQUENCE: 2

Asp Lys Ala Thr Ile Pro Ser Glu Ser Pro Phe Ala Ala Glu Val
1               5                   10                  15

Ala Asp Gly Ala Ile Val Val Asp Ile Ala Lys Met Lys Tyr Glu Thr
                20                  25                  30

Pro Glu Leu His Val Lys Val Gly Asp Thr Val Thr Trp Ile Asn Arg
            35                  40                  45

Glu Ala Met Pro His Asn Val His Phe Val Ala Gly Val Leu Gly Glu
        50                  55                  60

Ala Ala Leu Lys Gly Pro Met Met Lys Glu Gln Ala Tyr Ser Leu
65                  70                  75                  80

Thr Phe Thr Glu Ala Gly Thr Tyr Asp Tyr His Cys Thr Pro His Pro
                85                  90                  95

Phe Met Arg Gly Lys Val Val Val Glu
                100                 105

<210> SEQ ID NO 3
<211> LENGTH: 155
<212> TYPE: PRT
<213> ORGANISM: Escherichia coli

<400> SEQUENCE: 3

Met Leu Lys Gln Val Glu Ile Phe Thr Asp Gly Ser Cys Leu Gly Asn
1               5                   10                  15

Pro Gly Pro Gly Gly Tyr Gly Ala Ile Leu Arg Tyr Arg Gly Arg Glu
                20                  25                  30

Lys Thr Phe Ser Ala Gly Tyr Thr Arg Thr Thr Asn Asn Arg Met Glu
            35                  40                  45

Leu Met Ala Ala Ile Val Ala Leu Glu Ala Leu Lys Glu His Cys Glu
        50                  55                  60

Val Ile Leu Ser Thr Asp Ser Gln Tyr Val Arg Gln Gly Ile Thr Gln
65                  70                  75                  80

Trp Ile His Asn Trp Lys Lys Arg Gly Trp Lys Thr Ala Asp Lys Lys
                85                  90                  95

Pro Val Lys Asn Val Asp Leu Trp Gln Arg Leu Asp Ala Ala Leu Gly
                100                 105                 110

Gln His Gln Ile Lys Trp Glu Trp Val Lys Gly His Ala Gly His Pro
            115                 120                 125

Glu Asn Glu Arg Cys Asp Glu Leu Ala Arg Ala Ala Met Asn Pro
        130                 135                 140

Thr Leu Glu Asp Thr Gly Tyr Gln Val Glu Val
145                 150                 155

<210> SEQ ID NO 4
<211> LENGTH: 186
<212> TYPE: PRT
<213> ORGANISM: Gallus gallus

<400> SEQUENCE: 4

Val Arg Ser Leu Asn Ser Ile Val Ala Val Cys Gln Asn Met Gly Ile
1               5                   10                  15

Gly Lys Asp Gly Asn Leu Pro Trp Pro Pro Leu Arg Asn Glu Tyr Lys
                20                  25                  30

Tyr Phe Gln Arg Met Thr Ser Thr Ser His Val Glu Gly Lys Gln Asn
            35                  40                  45

```
Ala Val Ile Met Gly Lys Lys Thr Trp Phe Ser Ile Pro Glu Lys Asn
 50                  55                  60

Arg Pro Leu Lys Asp Arg Ile Asn Ile Val Leu Ser Arg Glu Leu Lys
 65                  70                  75                  80

Glu Ala Pro Lys Gly Ala His Tyr Leu Ser Lys Ser Leu Asp Asp Ala
                 85                  90                  95

Leu Ala Leu Leu Asp Ser Pro Glu Leu Lys Ser Lys Val Asp Met Val
                100                 105                 110

Trp Ile Val Gly Gly Thr Ala Val Tyr Lys Ala Ala Met Glu Lys Pro
                115                 120                 125

Ile Asn His Arg Leu Phe Val Thr Arg Ile Leu His Glu Phe Glu Ser
130                 135                 140

Asp Thr Phe Phe Pro Glu Ile Asp Tyr Lys Asp Phe Lys Leu Leu Thr
145                 150                 155                 160

Glu Tyr Pro Gly Val Pro Ala Asp Ile Gln Glu Asp Gly Ile Gln
                165                 170                 175

Tyr Lys Phe Glu Val Tyr Gln Lys Ser Val
                180                 185

<210> SEQ ID NO 5
<211> LENGTH: 85
<212> TYPE: PRT
<213> ORGANISM: Escherichia coli

<400> SEQUENCE: 5

Leu Thr Gln Glu Arg Lys Arg Glu Ile Ile Glu Gln Phe Lys Val His
 1               5                  10                  15

Glu Asn Asp Thr Gly Ser Pro Glu Val Gln Ile Ala Ile Leu Thr Glu
                 20                  25                  30

Gln Ile Asn Asn Leu Asn Glu His Leu Arg Val His Lys Lys Asp His
             35                  40                  45

His Ser Arg Arg Gly Leu Leu Lys Met Val Gly Lys Arg Arg Arg Leu
 50                  55                  60

Leu Ala Tyr Leu Arg Asn Lys Asp Val Ala Arg Tyr Arg Glu Ile Val
 65                  70                  75                  80

Glu Lys Leu Gly Leu
                 85

<210> SEQ ID NO 6
<211> LENGTH: 256
<212> TYPE: PRT
<213> ORGANISM: Bacillus licheniformis

<400> SEQUENCE: 6

Asp Asp Phe Ala Lys Leu Glu Glu Gln Phe Asp Ala Lys Leu Gly Ile
 1               5                  10                  15

Phe Ala Leu Asp Thr Gly Thr Asn Arg Thr Val Ala Tyr Arg Pro Asp
                 20                  25                  30

Glu Arg Phe Ala Phe Ala Ser Thr Ile Lys Ala Leu Thr Val Gly Val
             35                  40                  45

Leu Leu Gln Gln Lys Ser Ile Glu Asp Leu Asn Gln Arg Ile Thr Tyr
 50                  55                  60

Thr Arg Asp Asp Leu Val Asn Tyr Asn Pro Ile Thr Glu Lys His Val
 65                  70                  75                  80

Asp Thr Gly Met Thr Leu Lys Glu Leu Ala Asp Ala Ser Leu Arg Tyr
                 85                  90                  95
```

```
Ser Asp Asn Ala Ala Gln Asn Leu Ile Leu Lys Gln Ile Gly Pro
            100                 105                 110

Glu Ser Leu Lys Lys Glu Leu Arg Lys Ile Gly Asp Glu Val Thr Asn
    115                 120                 125

Pro Glu Arg Phe Glu Pro Leu Asn Glu Val Asn Pro Gly Glu Thr
130                 135                 140

Gln Asp Thr Ser Thr Ala Arg Ala Leu Val Thr Ser Leu Arg Ala Phe
145                 150                 155                 160

Ala Leu Glu Asp Lys Leu Pro Ser Glu Lys Arg Glu Leu Leu Ile Asp
                165                 170                 175

Trp Met Lys Arg Asn Thr Thr Gly Asp Ala Leu Ile Arg Ala Gly Val
                180                 185                 190

Pro Asp Gly Trp Glu Val Ala Asp Lys Thr Gly Ala Ala Ser Tyr Gly
                195                 200                 205

Thr Arg Asn Asp Ile Ala Ile Ile Trp Pro Pro Lys Gly Asp Pro Val
210                 215                 220

Val Leu Ala Val Leu Ser Ser Arg Asp Lys Lys Asp Ala Lys Tyr Asp
225                 230                 235                 240

Asp Lys Leu Ile Ala Glu Ala Thr Lys Val Val Met Lys Ala Leu Asn
                245                 250                 255

<210> SEQ ID NO 7
<211> LENGTH: 16
<212> TYPE: PRT
<213> ORGANISM: Escherichia coli

<400> SEQUENCE: 7

Leu Thr Gln Glu Arg Lys Arg Glu Ile Ile Glu Gln Phe Lys Val His
1               5                   10                  15

<210> SEQ ID NO 8
<211> LENGTH: 26
<212> TYPE: PRT
<213> ORGANISM: Escherichia coli

<400> SEQUENCE: 8

Gly Ser Pro Glu Val Gln Ile Ala Ile Leu Thr Glu Gln Ile Asn Asn
1               5                   10                  15

Leu Asn Glu His Leu Arg Val His Lys Lys
            20                  25

<210> SEQ ID NO 9
<211> LENGTH: 28
<212> TYPE: PRT
<213> ORGANISM: Escherichia coli

<400> SEQUENCE: 9

Lys Asp His His Ser Arg Arg Gly Leu Leu Lys Met Val Gly Lys Arg
1               5                   10                  15

Arg Arg Leu Leu Ala Tyr Leu Arg Asn Lys Asp Val
            20                  25

<210> SEQ ID NO 10
<211> LENGTH: 15
<212> TYPE: PRT
<213> ORGANISM: Escherichia coli

<400> SEQUENCE: 10

Lys Asp Val Ala Arg Tyr Arg Glu Ile Val Glu Lys Leu Gly Leu
1               5                   10                  15
```

<210> SEQ ID NO 11
<211> LENGTH: 12
<212> TYPE: PRT
<213> ORGANISM: Bacillus licheniformis

<400> SEQUENCE: 11

Asp Asp Phe Ala Lys Leu Glu Glu Gln Phe Asp Ala
1               5                   10

<210> SEQ ID NO 12
<211> LENGTH: 8
<212> TYPE: PRT
<213> ORGANISM: Bacillus licheniformis

<400> SEQUENCE: 12

Leu Asp Thr Gly Thr Asn Arg Thr
1               5

<210> SEQ ID NO 13
<211> LENGTH: 7
<212> TYPE: PRT
<213> ORGANISM: Bacillus licheniformis

<400> SEQUENCE: 13

Tyr Arg Pro Asp Glu Arg Phe
1               5

<210> SEQ ID NO 14
<211> LENGTH: 20
<212> TYPE: PRT
<213> ORGANISM: Bacillus licheniformis

<400> SEQUENCE: 14

Phe Ala Ser Thr Ile Lys Ala Leu Thr Val Gly Val Leu Leu Gln Gln
1               5                   10                  15

Lys Ser Ile Glu
            20

<210> SEQ ID NO 15
<211> LENGTH: 9
<212> TYPE: PRT
<213> ORGANISM: Bacillus licheniformis

<400> SEQUENCE: 15

Ser Ile Glu Asp Leu Asn Gln Arg Ile
1               5

<210> SEQ ID NO 16
<211> LENGTH: 8
<212> TYPE: PRT
<213> ORGANISM: Bacillus licheniformis

<400> SEQUENCE: 16

Tyr Thr Arg Asp Asp Leu Val Asn
1               5

<210> SEQ ID NO 17
<211> LENGTH: 13
<212> TYPE: PRT
<213> ORGANISM: Bacillus licheniformis

<400> SEQUENCE: 17

Tyr Asn Pro Ile Thr Glu Lys His Val Asp Thr Gly Met

<210> SEQ ID NO 18
<211> LENGTH: 15
<212> TYPE: PRT
<213> ORGANISM: Bacillus licheniformis

<400> SEQUENCE: 18

Gly Met Thr Leu Lys Glu Leu Ala Asp Ala Ser Leu Arg Tyr Ser
1               5                   10                  15

<210> SEQ ID NO 19
<211> LENGTH: 15
<212> TYPE: PRT
<213> ORGANISM: Bacillus licheniformis

<400> SEQUENCE: 19

Ser Asp Asn Ala Ala Gln Asn Leu Ile Leu Lys Gln Ile Gly Gly
1               5                   10                  15

<210> SEQ ID NO 20
<211> LENGTH: 15
<212> TYPE: PRT
<213> ORGANISM: Bacillus licheniformis

<400> SEQUENCE: 20

Gly Gly Pro Glu Ser Leu Lys Lys Glu Leu Arg Lys Ile Gly Asp
1               5                   10                  15

<210> SEQ ID NO 21
<211> LENGTH: 7
<212> TYPE: PRT
<213> ORGANISM: Bacillus licheniformis

<400> SEQUENCE: 21

Gly Asp Glu Val Thr Asn Pro
1               5

<210> SEQ ID NO 22
<211> LENGTH: 7
<212> TYPE: PRT
<213> ORGANISM: Bacillus licheniformis

<400> SEQUENCE: 22

Asn Pro Glu Arg Phe Glu Pro
1               5

<210> SEQ ID NO 23
<211> LENGTH: 10
<212> TYPE: PRT
<213> ORGANISM: Bacillus licheniformis

<400> SEQUENCE: 23

Arg Phe Glu Pro Glu Leu Asn Glu Val Asn
1               5                   10

<210> SEQ ID NO 24
<211> LENGTH: 7
<212> TYPE: PRT
<213> ORGANISM: Bacillus licheniformis

<400> SEQUENCE: 24

Val Asn Pro Gly Glu Thr Gln
1               5

```
<210> SEQ ID NO 25
<211> LENGTH: 8
<212> TYPE: PRT
<213> ORGANISM: Bacillus licheniformis

<400> SEQUENCE: 25

Gly Glu Thr Gln Asp Thr Ser Thr
1               5

<210> SEQ ID NO 26
<211> LENGTH: 17
<212> TYPE: PRT
<213> ORGANISM: Bacillus licheniformis

<400> SEQUENCE: 26

Thr Ser Thr Ala Arg Ala Leu Val Thr Ser Leu Arg Ala Phe Ala Leu
1               5                   10                  15

Glu

<210> SEQ ID NO 27
<211> LENGTH: 18
<212> TYPE: PRT
<213> ORGANISM: Bacillus licheniformis

<400> SEQUENCE: 27

Lys Leu Pro Ser Glu Lys Arg Glu Leu Leu Ile Asp Trp Met Lys Arg
1               5                   10                  15

Asn Thr

<210> SEQ ID NO 28
<211> LENGTH: 10
<212> TYPE: PRT
<213> ORGANISM: Bacillus licheniformis

<400> SEQUENCE: 28

Arg Asn Thr Thr Gly Asp Ala Leu Ile Arg
1               5                   10

<210> SEQ ID NO 29
<211> LENGTH: 9
<212> TYPE: PRT
<213> ORGANISM: Bacillus licheniformis

<400> SEQUENCE: 29

Ala Leu Ile Arg Ala Gly Val Pro Asp
1               5

<210> SEQ ID NO 30
<211> LENGTH: 6
<212> TYPE: PRT
<213> ORGANISM: Bacillus licheniformis

<400> SEQUENCE: 30

Ile Trp Pro Ile Trp Pro
1               5

<210> SEQ ID NO 31
<211> LENGTH: 7
<212> TYPE: PRT
<213> ORGANISM: Bacillus licheniformis

<400> SEQUENCE: 31

Pro Lys Gly Asp Pro Val Val
```

```
<210> SEQ ID NO 32
<211> LENGTH: 18
<212> TYPE: PRT
<213> ORGANISM: Bacillus licheniformis

<400> SEQUENCE: 32

Tyr Asp Asp Lys Leu Ile Ala Glu Ala Thr Lys Val Val Met Lys Ala
1               5                   10                  15

Leu Asn

<210> SEQ ID NO 33
<211> LENGTH: 8
<212> TYPE: PRT
<213> ORGANISM: Escherichia coli

<400> SEQUENCE: 33

His Glu Asn Asp Thr Gly Ser Pro
1               5

<210> SEQ ID NO 34
<211> LENGTH: 7
<212> TYPE: PRT
<213> ORGANISM: Escherichia coli

<400> SEQUENCE: 34

His Lys Lys Asp His His Ser
1               5

<210> SEQ ID NO 35
<211> LENGTH: 13
<212> TYPE: PRT
<213> ORGANISM: Bacillus licheniformis

<400> SEQUENCE: 35

Asp Ala Lys Leu Gly Ile Phe Ala Leu Asp Thr Gly Thr
1               5                   10

<210> SEQ ID NO 36
<211> LENGTH: 11
<212> TYPE: PRT
<213> ORGANISM: Bacillus licheniformis

<400> SEQUENCE: 36

Thr Gly Thr Asn Arg Thr Val Ala Tyr Arg Pro
1               5                   10

<210> SEQ ID NO 37
<211> LENGTH: 7
<212> TYPE: PRT
<213> ORGANISM: Bacillus licheniformis

<400> SEQUENCE: 37

Pro Asp Glu Arg Phe Ala Phe
1               5

<210> SEQ ID NO 38
<211> LENGTH: 7
<212> TYPE: PRT
<213> ORGANISM: Bacillus licheniformis

<400> SEQUENCE: 38

Arg Phe Ala Phe Ala Ser Thr
```

```
1               5

<210> SEQ ID NO 39
<211> LENGTH: 10
<212> TYPE: PRT
<213> ORGANISM: Bacillus licheniformis

<400> SEQUENCE: 39

Leu Asn Gln Arg Ile Thr Tyr Thr Arg Asp
1               5                   10

<210> SEQ ID NO 40
<211> LENGTH: 7
<212> TYPE: PRT
<213> ORGANISM: Bacillus licheniformis

<400> SEQUENCE: 40

Val Asn Tyr Asn Pro Ile Thr
1               5

<210> SEQ ID NO 41
<211> LENGTH: 8
<212> TYPE: PRT
<213> ORGANISM: Bacillus licheniformis

<400> SEQUENCE: 41

Leu Arg Tyr Ser Asp Asn Ala Ala
1               5

<210> SEQ ID NO 42
<211> LENGTH: 7
<212> TYPE: PRT
<213> ORGANISM: Bacillus licheniformis

<400> SEQUENCE: 42

Lys Ile Gly Asp Glu Val Thr
1               5

<210> SEQ ID NO 43
<211> LENGTH: 8
<212> TYPE: PRT
<213> ORGANISM: Bacillus licheniformis

<400> SEQUENCE: 43

Glu Val Thr Asn Pro Glu Arg Phe
1               5

<210> SEQ ID NO 44
<211> LENGTH: 7
<212> TYPE: PRT
<213> ORGANISM: Bacillus licheniformis

<400> SEQUENCE: 44

Leu Asn Glu Val Asn Pro Gly
1               5

<210> SEQ ID NO 45
<211> LENGTH: 8
<212> TYPE: PRT
<213> ORGANISM: Bacillus licheniformis

<400> SEQUENCE: 45

Asn Pro Gly Glu Thr Gln Asp Thr
1               5
```

```
<210> SEQ ID NO 46
<211> LENGTH: 7
<212> TYPE: PRT
<213> ORGANISM: Bacillus licheniformis

<400> SEQUENCE: 46

Thr Gln Asp Thr Ser Thr Ala
1               5

<210> SEQ ID NO 47
<211> LENGTH: 7
<212> TYPE: PRT
<213> ORGANISM: Bacillus licheniformis

<400> SEQUENCE: 47

Met Lys Arg Asn Thr Thr Gly
1               5

<210> SEQ ID NO 48
<211> LENGTH: 15
<212> TYPE: PRT
<213> ORGANISM: Bacillus licheniformis

<400> SEQUENCE: 48

Pro Asp Gly Trp Glu Val Ala Asp Lys Thr Gly Ala Ala Ser Tyr
1               5                   10                  15

<210> SEQ ID NO 49
<211> LENGTH: 15
<212> TYPE: PRT
<213> ORGANISM: Escherichia coli

<400> SEQUENCE: 49

Ser Tyr Gly Thr Arg Asn Asp Ile Ala Ile Ile Trp Pro Pro Lys
1               5                   10                  15

<210> SEQ ID NO 50
<211> LENGTH: 15
<212> TYPE: PRT
<213> ORGANISM: Bacillus licheniformis

<400> SEQUENCE: 50

Gly Asp Pro Val Val Leu Ala Val Leu Ser Ser Arg Asp Lys Lys
1               5                   10                  15

<210> SEQ ID NO 51
<211> LENGTH: 10
<212> TYPE: PRT
<213> ORGANISM: Bacillus licheniformis

<400> SEQUENCE: 51

Lys Lys Asp Ala Lys Tyr Asp Asp Lys Leu
1               5                   10

<210> SEQ ID NO 52
<211> LENGTH: 13
<212> TYPE: PRT
<213> ORGANISM: Escherichia coli

<400> SEQUENCE: 52

Gln Phe Lys Val His Glu Asn Asp Thr Gly Ser Pro Glu
1               5                   10

<210> SEQ ID NO 53
```

```
<211> LENGTH: 9
<212> TYPE: PRT
<213> ORGANISM: Escherichia coli

<400> SEQUENCE: 53

Val His Lys Lys Asp His His Ser Arg
1               5

<210> SEQ ID NO 54
<211> LENGTH: 9
<212> TYPE: PRT
<213> ORGANISM: Bacillus licheniformis

<400> SEQUENCE: 54

Leu Asp Thr Gly Thr Asn Arg Thr Val
1               5

<210> SEQ ID NO 55
<211> LENGTH: 20
<212> TYPE: PRT
<213> ORGANISM: Bacillus licheniformis

<400> SEQUENCE: 55

Leu Asn Gln Arg Ile Thr Tyr Thr Arg Asp Asp Leu Val Asn Tyr Asn
1               5                   10                  15

Pro Ile Thr Glu
            20

<210> SEQ ID NO 56
<211> LENGTH: 17
<212> TYPE: PRT
<213> ORGANISM: Bacillus licheniformis

<400> SEQUENCE: 56

Arg Lys Ile Gly Asp Glu Val Thr Asn Pro Glu Arg Phe Glu Pro Glu
1               5                   10                  15

Leu

<210> SEQ ID NO 57
<211> LENGTH: 13
<212> TYPE: PRT
<213> ORGANISM: Bacillus licheniformis

<400> SEQUENCE: 57

Leu Asn Glu Val Asn Pro Gly Glu Thr Gln Asp Thr Ser
1               5                   10

<210> SEQ ID NO 58
<211> LENGTH: 11
<212> TYPE: PRT
<213> ORGANISM: Bacillus licheniformis

<400> SEQUENCE: 58

Phe Ala Leu Glu Asp Lys Leu Pro Ser Glu Lys
1               5                   10

<210> SEQ ID NO 59
<211> LENGTH: 11
<212> TYPE: PRT
<213> ORGANISM: Bacillus licheniformis

<400> SEQUENCE: 59

Lys Arg Asn Thr Thr Gly Asp Ala Leu Ile Arg
1               5                   10
```

```
<210> SEQ ID NO 60
<211> LENGTH: 13
<212> TYPE: PRT
<213> ORGANISM: Bacillus licheniformis

<400> SEQUENCE: 60

Ser Arg Asp Lys Lys Asp Ala Lys Tyr Asp Asp Lys Leu
1               5                   10

<210> SEQ ID NO 61
<211> LENGTH: 85
<212> TYPE: PRT
<213> ORGANISM: Escherichia coli

<400> SEQUENCE: 61

Met Gln Thr Val Ile Phe Gly Arg Ser Gly Cys Pro Tyr Cys Val Arg
1               5                   10                  15

Ala Lys Asp Leu Ala Glu Lys Leu Ser Asn Glu Arg Asp Asp Phe Gln
                20                  25                  30

Tyr Gln Tyr Val Asp Ile Arg Ala Glu Gly Ile Thr Lys Glu Asp Leu
            35                  40                  45

Gln Gln Lys Ala Gly Lys Pro Val Glu Thr Val Pro Gln Ile Phe Val
    50                  55                  60

Asp Gln Gln His Ile Gly Gly Tyr Thr Asp Phe Ala Ala Trp Val Lys
65                  70                  75                  80

Glu Asn Leu Asp Ala
                85

<210> SEQ ID NO 62
<211> LENGTH: 26
<212> TYPE: PRT
<213> ORGANISM: Haloarcula marismortui

<400> SEQUENCE: 62

Glu Ala Ala Glu Ala Gln Gly Tyr Asp Trp Pro Phe Ser Cys Arg Ala
1               5                   10                  15

Gly Ala Cys Ala Asn Cys Ala Ala Ile Val
                20                  25
```

METHODS, SYSTEMS, ALGORITHMS AND MEANS FOR DESCRIBING THE POSSIBLE CONFORMATIONS OF ACTUAL AND THEORETICAL PROTEINS AND FOR EVALUATING ACTUAL AND THEORETICAL PROTEINS WITH RESPECT TO FOLDING, OVERALL SHAPE AND STRUCTURAL MOTIFS

PRIORITY STATEMENT

This Patent Cooperation Treaty (PCT) application claims priority to U.S. Provisional App. 60/898,529, filed Jan. 31, 2007, U.S. Provisional App. 61/004,094, filed Nov. 23, 2007, and U.S. Provisional App. 61/062,775, filed Jan. 29, 2008.

FIELD OF THE INVENTION

The present invention is directed to means and methods for describing protein folding in three-dimensional space.

BACKGROUND OF THE INVENTION

Although three-dimensional structures of proteins are available at the atomic level, for example, from experimental measurements such as X-ray crystallography and nuclear magnetic resonance (NMR) or computational simulations, the description of protein folding and the consequent shapes is still a challenging subject. In a folded protein, some local fragments can be described as α-helices and β-strands that are due to hydrogen bond formation. However, the remaining local fragments of the protein are commonly irregular coils, loops and other shapes and conformations that are difficult to identify and describe.

Several methods have been developed to compare protein structures with alignment of secondary structures, such as Dali (see Holm L, Sander C., J. Mol. Biol., 1993a; 233: 123-138), STRUCTAL (see Gerstein M, Levitt, M. In Proc. Fourth Int. Conf. on Intell. Sys. for Mol. Biol. Menlo Park, Calif.: AAAI Press. 1996. p 59-67.), VAST (see Gibrat J F, Madel T, Bryant S H. Curr. Opin. Struct. Biol. 1996; 6:377-385.), LOCK (see Singh A P, Brutlag D L. In Proc. Fifth Int. Conf. on Intell. Sys. for Mol. Biol. Menlo Park, Calif.: AAAI Press. 1997. p 284-293.), 3DSearch (see Singh A, Brutlag D. 3dSearch http://gene.stanford.edu/3dSearch.), CE (see Shindyalov I N, Bourne P E. Protein Eng. 1998; 11(9):739-47.), SSM (see Krissinel E, Henrick K, Acta Crystallogr D Biol Crystallogr. 2004; 60(Pt 12 Pt 1): 2256-2268.), PALI (see Balaji S, Sujatha S, Kumar S S C, Srinivasan, N. PALI, Nucleic Acids Res. 2001; 29: 61-65.), and the like, all of which are hereby incorporated by reference. The structural classification of protein has been defined and stored by SCOP and CATH database (see Park J H, Ryu S Y, Kim C L, Park I K J., Genome Informatics 2001; 12: 350-351; and Hadley C, Jones D T. Structure 1999; 7(9): 1099-112).

A significant challenge in the study of protein folding relates to the need or the requirement to describe and compare the possible types of folding motifs. It has been estimated that there can be as many as 4,000 possible types of folding in protein, among which about 2,000 types are known in naturally-occurring proteins (see Govindarajan S, Recabarren R, Goldstein R A., Proteins. 1999; 35(4): 408-414). Because of the existence of such a large number of rare and unnatural types of folds, a comprehensive database for all the existing types of folding is difficult. The lack of knowledge regarding protein folding and conformation has led to the development of many technologies.

For example, U.S. Pat. No. 5,265,030 to Skolnick et al. is a method for determining a protein's tertiary structure from a primary sequence of amino acid residues. Specifically, the method in the '030 patent considers the free unconstrained interactions between residues and between side chains, and tracks the entire folding operation from the protein's unfolded state to its full folded state. The '030 patent does not use torsion angles and pitch distances within overlapping elements, wherein each element consists of five consecutive amino acids, to describe protein folding.

U.S. Pat. No. 5,680,319 to Rose et al. is directed to a computer-assisted method for predicting the three-dimensional structure of a protein fragment from its amino acid sequence. This method starts with a defined polypeptide chain of defined sequence, preferably in a fully extended conformation, and uses idealized geometry and highly simplified energy functions to fold the chain in hierarchic stages to predict both secondary and super-secondary structures. The '319 patent does not use torsion angles and pitch distances within overlapping elements, wherein each element consists of five amino acids to describe protein folding.

U.S. Pat. Nos. 6,345,235 and 6,516,277 to Edgecombe et al. are directed to determining multi-dimensional topology of a substance within a volume. Specifically, the methods determine molecular shape and structural information of proteins using van der Waals surfaces, electrostatic potentials or electron density. The '235 and '277 patents do not use torsion angles and pitch distances within overlapping elements, wherein an element consists of five amino acids, to describe protein folding.

U.S. Pat. No. 6,512,981 Eisenberg et al. is directed to a computer-assisted method for assigning an amino acid probe sequence to a known three-dimensional protein structure. Specifically, the method uses the amino acid sequence of the probe, and the sequence-derived properties of the probe sequence, such as the secondary structure, and solvent accessibility to compute an alignment score. The '981 patent does not use torsion angles and pitch distances within overlapping elements, wherein each element consists of five amino acids, to describe protein folding.

U.S. Pat. No. 6,792,355 to Hansen et al. is a method for separating two or more subsets of polypeptides within a set of polypeptides using the steps of selecting a sequence comparison signature for each amino acid sequence, constructing a distance arrangement according to the distance between each of the sequence comparison signatures, and identifying a first and second cluster of sequence comparison signatures. The '355 patent does not use torsion angles and pitch distances within overlapping elements, wherein each element consists of five amino acids, to describe protein folding.

U.S. Pat. No. 6,832,162 to Floudas et al. is directed to an ab initio prediction of the secondary and tertiary protein structures by using selected force fields to calculate first, the low energy conformations of overlapping pentapeptides and then, the total free energy of the entire system. The '162 patent does not use torsion angles and pitch distances within overlapping elements, wherein each element consists of five amino acids, to describe protein folding.

U.S. Pat. No. 7,158,888 to McRee et al. is related to determining a structure of a target biomolecule such as a protein from X-ray diffraction data. Specifically, the method in the '888 patent performs multiple molecular replacement searches on the X-ray data using a search model, compares molecular replacement solutions thus derived, and predicts which search model biomolecule has superior structure identity with the target biomolecule. The '888 patent does not use torsion angles and pitch distances within overlapping elements, wherein each element consists of five amino acids, to describe protein folding.

U.S. Pat. No. 7,288,382 to Harbury et al. is a method for structural analysis of proteins, including mapping of the sites for ligand binding, and protein-protein interactions. Specifically, the method in the '382 patent introduces cysteine residues by translational misincorporation such that the misincorporated cysteines serve as targets for modification. The '382 does not use torsion angles and pitch distances within overlapping elements, wherein each element consists of five amino acids, to describe protein folding.

In sum, none of the conventional methods for describing protein folding and conformations are satisfactory. Therefore, there remains a need for a method to describe all possible types of folding in proteins. There also remains a need for an algorithm to compare folding among different proteins or different conformations of the same protein.

SUMMARY OF THE INVENTION

In accordance with the several objects of the invention, methods, systems, algorithms and means for analyzing, predicting or expressing the conformation of a target protein, or portions of the target protein, are provided. The methods and systems of the invention can be embodied in a computer, or in any device capable of performing the steps of the method with respect to one or more portions of a protein or to one or more entire proteins, or with respect to one or more comparative proteins, or with respect to one or more theoretical or predictive examples of desired proteins. Thus, the present invention encompasses any device, such as a computer or computational chip, as well as the algorithms for carrying out the present methods.

Although in some preferred embodiments the target protein preferably is oriented from its N-terminus to its C-terminus in order to take advantage of publicly available data that is provided in the N-to-C termini direction, in other embodiments, the means and methods of the invention can be practiced with respect to sequences in the C-terminus to N-terminus direction.

In one preferred embodiment, the method of the invention comprises five salient steps. These five steps are: Step A, dividing a target protein or at least one portion of a target protein into elements, wherein each element consists of five consecutive amino acids, the five consecutive amino acids consisting of a first amino acid, a second amino acid, a third amino acid, a fourth amino acid and a fifth amino acid, and wherein each amino acid comprises an alpha carbon atom; and then performing Step B, determining a range value for a first torsion angle with respect to a first element, wherein the first torsion angle is determined with respect to a first plane and a second plane wherein the first plane is defined by the alpha carbons of the first, second and third amino acids, the second plane is defined by the alpha carbons of the second, third and fourth amino acids, and the first torsion angle lies between the first plane and the second plane, and wherein each torsion angle range value for the first and second torsion angles is selected from the group of ranges consisting of range $a_1$, range $a_2$, and range $a_3$; and then performing Step C, determining a range value for a second torsion angle with respect to the first element, wherein the second torsion angle is determined with respect to the second plane and a third plane, wherein the third plane is defined by the alpha carbons of the third, fourth and fifth amino acids, and the second torsion angle lies between the second plane and the third plane wherein each range angle value for the first and second torsion angles is selected from the group of ranges consisting of range $b_1$, range $b_2$, and range $b_3$; and then performing Step D, determining the pitch distance range value between the alpha carbon of the first amino acid and the alpha carbon of the fifth amino acid to obtain a first element pitch range value, and wherein each pitch distance range value is selected from the group of ranges consisting of range $c_1$, range $c_2$, and range $c_3$, and then performing Step E, combining the values obtained from Steps B, C and D to obtain a first element vector.

The various steps and permutations of the means and method of the invention are preferably performed by one or more of the Protein Folding Shape Code (PFSC) algorithms of the invention. In one salient aspect of the invention, each succeeding element of the target protein overlaps the preceding element by four amino acids. Thus, the algorithms of the invention are applied to successive elements such that the resultant vectors provide many permutations with respect to the evaluation and description of the possible conformations of the protein or protein portion. In another key aspect, the first torsion angle lies substantially normal to both the first plane and the second plane, and the second torsion angle lies substantially normal to both the second plane and the third plane.

In some preferred embodiments of the invention, for some functions of the processes, steps and algorithms of the invention, the third alpha carbon of each five-carbon element of the five amino acids of the element is designated as the center carbon upon which certain algorithmic operations can be performed. Thus, methods of the invention include wherein, with respect to the center carbon of the five alpha carbons, the first alpha-carbon is designated the $(n-2)^{th}$ alpha carbon, the second alpha carbon is designated the $(n-1)^{th}$ alpha carbon, the third alpha carbon is the center alpha carbon and is designated the $n^{th}$ alpha carbon, the fourth alpha carbon is designated the $(n+1)^{th}$ alpha carbon, and the fifth alpha carbon is designated the $(n+2)^{th}$ alpha carbon.

In accordance with other advantages of the means, methods and algorithms of the invention, the method of the invention can be used to evaluate, analyze or describe succeeding elements of a portion of a protein or the entire protein. In some preferred embodiments, these successive elements are subjected to further steps of the method, these steps being Step F, repeating Step A with respect to a second element of the target protein, wherein the second element consists of five consecutive amino acids, the five consecutive amino acids consisting of a second element first amino acid (which is the same as the first element first amino acid), a second element second amino acid (which is the same as the third amino acid of the first element), a second element third amino acid (which is the same as the fourth amino acid of the first element, a second element fourth amino acid (which is the same as the fifth amino acid of the first element) and a second element fifth amino acid (which is in addition to the last four amino acids of the first element). As in the other steps of the invention, the method necessarily is performed with respect to the alpha carbon atoms of each amino acid of the element.

As the next step G in the method of the invention, Step B is repeated with respect to the second element of the target protein to obtain a first range value for a first torsion angle with respect to the second element, wherein the first torsion angle of the second element is determined with respect to a first plane of the second element and a second plane of the second element, wherein the first plane of the second element is defined by the alpha carbons of the first, second and third amino acids of the second element, the second plane of the second element is defined by the alpha carbons of the second, third and fourth amino acids, and the first torsion angle lies between the first plane and the second plane of the second element, and wherein each torsion angle range value for the first torsion angle is selected from the group of ranges consisting of range $a_1$, range $a_2$, and range $a_3$, and then performing Step H, repeating Step C with respect to the second element of the target protein to obtain a range value for a second torsion angle with respect to the second element, wherein the second torsion angle is determined with respect to a second plane of the second element and a third plane of the second element, wherein the second plane is defined by the alpha carbons of the second, third and fourth amino acids of the second element, the third plane is defined by the alpha carbons of the third, fourth and fifth amino acids of the second element, and the second torsion angle lies between the second plane and the third plane of the second element, wherein the torsion angle range value for the second torsion angle of the second element is selected from the group of ranges consisting of range $b_1$, range $b_2$, and range $b_3$, and then performing the Step I, consisting of repeating Step D with respect to the second element of the target protein to determine the pitch distance range value between the alpha carbons of the first and fifth amino acids of the second element to obtain a second element pitch range value, and wherein each pitch distance range value is selected from the group of ranges consisting of range $c_1$, range $c_2$, and range $c_3$, and then performing Step J, repeating Step E to combine the values obtained from steps G, H and I to obtain a second element vector.

The method or methods of the present invention may be performed as many times as desired with respect to additional elements of a protein portion or to the entire protein. Thus, by repeating Steps A, B, C, D and E with respect to successive overlapping elements of the target protein, a first set of vectors can be obtained, the first set corresponding to at least a portion of the target protein. By iteratively repeating Steps A, B, C, D and E with respect to successive elements of an entire protein, a complete set of vectors can be obtained for the entire protein.

A set of vectors can be obtained, the complete set corresponding to the entire target protein. With the present methods, systems and algorithms, the possible conformations of an actual or theoretical protein can be obtained. In the context of the present invention, "conformation" means any aspect of the protein or portion thereof that pertains to the actual, possible or theoretical three-dimensional characteristics of the protein.

Methods of the invention further comprise the repetition of the steps with respect to a second element of the target protein, with respect to a third element of the target protein, and with respect to a few or numerous other succeeding elements of the target protein to arrive at a set of vectors. Thus, one or more sets of vectors regarding the target protein, or a portion of the target protein, may be obtained. Moreover, the sets of vectors can be subjected to the algorithms of the invention to determine one or more aspects of the conformation of the target protein.

In accordance with other salient aspects of the invention, the ranges for the first and second torsion angles can be overlapping or exclusive. For example, in some embodiments of the methods and algorithms of the invention, range $a_1$ is from 0° to 160°, range $a_2$ is from +120° to −120°, and range $a_3$ is from −160° to 0°. In other embodiments, range $a_1$ is from 0° to 130°, range $a_2$ is from +130° to 180° and −180° to −130°, and range $a_3$ is from −130° to 0°. In yet other embodiments, range $b_1$ is from 0° to 160°, range $b_2$ is from +120° to −120°, and range $b_3$ is from −160° to 0°. As another alternate range, in some embodiments, range $b_1$ is from 0° to 130°, range $b_2$ is from 130° to 180° and −180° to −130°, and range $b_3$ is from −130° to 0°.

With respect to the ranges of values for the pitch distances, in some embodiments, the systems and methods of the invention utilize ranges wherein range $c_1$ is from zero to 7.0 Å, range $c_2$ is from 4.0 Å to 17.0 Å, and range $c_3$ is greater than 17.0 Å. In other embodiments, the pitch distance range values for range $c_1$ is from zero to 5.5 Å, for range $c_2$ is from 5.5 Å to 14.0 Å, and range $c_3$ is greater than 14.0 Å. As an additional advantage of the systems, algorithms and methods of the invention, the data for determining which values fall into which ranges for ranges, a1, a2, and a3, for ranges b1, b2, and b3, and for ranges c1, c2, and c3, can be obtained from a database, while some other values can be calculated.

According to the systems, methods and algorithms of the present invention, each element of the protein portion, or the entire protein, preferably is subjected to the PFSC algorithms of the invention to derive one vector for each element, and each vector is one selected from a matrix of 27 vectors. In that matrix, as is shown in FIG. 6, the combination of the values for $a_1$, $b_1$, and $c_1$ yields vector "D;" the combination of the values for $a_1$, $b_1$, and $c_2$ yields vector "A;" the combination of the values for $a_1$, $b_1$, and $c_3$ yields vector "H;" the combination of the values for $a_1$, $b_2$, and $c_1$ yields vector "W;" the combination of the values for $a_1$, $b_2$, and $c_2$, yields vector "V;" the combination of the values for $a_1$, $b_2$, and $c_3$, yields vector "U;" the combination of the values for $a_1$, $b_3$, and $c_1$, yields vector "Z;" the combination of the values for $a_1$, $b_3$, and $c_2$, yields vector "Y;" the combination of the values for $a_1$, $b_3$, and $c_3$, yields vector "X;" the combination of the values for $a_2$, $b_1$, and $c_1$, yields vector "K;" the combination of the values for $a_2$, $b_1$, and $c_2$, yields vector "J;" the combination of the values for $a_2$, $b_1$, and $c_3$, yields vector "I;" the combination of the values for $a_2$, $b_2$, and $c_1$, yields vector "G;" the combination of the values for $a_2$, $b_2$, and $c_2$, yields vector "B;" the combination of the values for $a_2$, $b_2$, and $c_3$, yields vector "E;" the combination of the values for $a_2$, $b_3$, and $c_1$, yields vector "T;" the combination of the values for $a_2$, $b_3$, and $c_2$, yields vector "S;" the combination of the values for $a_2$, $b_3$, and $c_3$, yields vector "R;" the combination of the values for $a_3$, $b_1$, and $c_1$, yields vector "Q;" the combination of the values or $a_3$, $b_1$, and $c_2$, yields vector "P;" the combination of the values for $a_3$, $b_1$, and $c_3$, yields vector "O;" the combination of the values for $a_3$, $b_2$, and $c_1$, yields vector "N;" the combination of the values for $a_3$, $b_2$, and $c_2$, yields vector "M;" the combination of the values for $a_3$, $b_2$, and $c_3$, yields vector "L;" the combination of the values for $a_3$, $b_3$, and $c_1$, yields vector "$;" the combination of the values for $a_3$, $b_3$, and $c_2$, yields vector "C;" and the combination of the values for $a_3$, $b_3$, and $c_3$ yields vector "F."

As an additional advantage of the systems, methods, computer platforms and algorithms of the invention, data regarding the target protein or portions thereof to be evaluated or described in accordance with the various steps of the methods of the invention, such as Steps A, B, C, D, and E may be obtained or derived from one or more databases. Any database or group of databases which is adapted and arranged to provide some or all of the data required for practicing the present invention may be used in conjunction with the invention. Examples of such databases include one or more from the list of databases comprising the Protein Data Bank, the WWPDB, the RCSB PDB, the MSD-EBI, the PDBj, the BMRB, the NCBI MMDB and private databases.

The systems, methods and algorithms of the invention may be provided for performing one or all of the methods, such as Steps A, B, C, D and E, and can be provided in fixed form in a digital processing or storage medium. For example, the algorithms, systems and methods of the invention may be provided in combination with, or as part of, a computing platform comprising a storage device and a data processing unit adapted and arranged for performing the methods of the invention. Moreover, the invention may be embodied within a computer-generated model representing and applying the algorithms of the systems and methods of the invention. As a further advantage, the methods and algorithms of the invention directed to performing one or all of Steps of the methods may be provided via a computer network such as the Internet, or via a website.

In accordance with other advantageous aspects of the invention a computer-facilitated method for describing or expressing the likely permutations of folding of a target protein, wherein the target protein comprises a chain of amino acids in a consecutive sequence, is provided. In one salient aspect, the method preferably comprises the steps of A, providing an algorithm which divides a target protein or at least one portion of a target protein into elements, wherein each element consists of five consecutive amino acids, the five consecutive amino acids consisting of a first amino acid, a second amino acid, a third amino acid, a fourth amino acid and a fifth amino acid, and wherein each amino acid comprises an alpha carbon atom; and B, providing an algorithm which obtains or determines a first torsion angle range value with respect to the first element, wherein the first torsion angle is determined with respect to a first plane and the alpha carbon of the fourth amino acid, wherein the first plane is defined by the alpha carbons of the first, second and third amino acids, and the first torsion angle lies between the first plane and the fourth alpha carbon, and wherein each torsion angle range value for the first and second torsion angles is selected from the group of ranges consisting of range $a_1$, range $a_2$, and range $a_3$, and C, providing an algorithm which obtains or determines a second torsion angle range value with respect to the first element, wherein the second torsion angle is determined with respect to a second plane and the alpha carbon of the fifth amino acid, wherein the second plane is defined by the alpha carbons of the second, third and fourth amino acids, and the second torsion angle lies between the second plane and the fifth alpha carbon, wherein each torsion angle range value for the first and second torsion angles is selected from the group of ranges consisting of range $b_1$, range $b_2$, and range $b_3$, and D, providing an algorithm which determines the range value of the pitch distance between the alpha carbon of the first amino acid and the alpha carbon of the fifth amino acid to obtain a first element pitch range value, and wherein each pitch distance range value is selected from the group of ranges consisting of range $c_1$, range $c_2$, and range $c_3$, and E, providing an algorithm which combines the values obtained from steps B, C and D to obtain a first element vector.

Methods of the invention further comprise the repetition of the steps with respect to a second element of the target protein, with respect to a third element of the target protein, and with respect to a few or numerous other succeeding elements of the target protein to arrive at a set of vectors. Thus, one or more sets of vectors regarding the target protein, or a portion of the target protein, may be obtained. Moreover, the sets of vectors can be subjected to the algorithms of the invention to determine one or more aspects of the conformation of the target protein.

In accordance with other salient aspects of the invention, the ranges for the first and second torsion angles can be overlapping or exclusive. For example, in some embodiments of the methods and algorithms of the invention, range $a_1$ is from 0° to 160°, range $a_2$ is from +120° to −120°, and range $a_3$ is from −160° to 0°. In other embodiments, range $a_1$ is from 0° to 130°, range $a_2$ is from +130° to 180° and −180° to −130°, and range $a_3$ is from −130° to 0°. In yet other embodiments, range $b_1$ is from 0° to 160°, range $b_2$ is from +120° to −120°, and range $b_3$ is from −160° to 0°. As another alternate range, in some embodiments, range $b_1$ is from 0° to 130°, range $b_2$ is from 130° to 180° and −180° to −130°, and range $b_3$ is from −130° to 0°.

With respect to the ranges of values for the pitch distances, in some embodiments, the systems and methods of the invention utilize ranges wherein range $c_1$ is from zero to 7.0 Å, range $c_2$ is from 4.0 Å to 17.0 Å, and range $c_3$ is greater than 17.0 Å. In other embodiments, the pitch distance range values for range $c_1$ is from zero to 5.5 Å, for range $c_2$ is from 5.5 Å to 14.0 Å, and range $c_3$ is greater than 14.0 Å. As an additional advantage of the systems, algorithms and methods of the invention, the data for determining which values fall into which ranges for ranges, a1, a2, and a3, for ranges b1, b2, and b3, and for ranges c1, c2, and c3, can be obtained from a database, while some other values can be calculated.

In yet other key aspects, the present systems, algorithms and methods of the invention include also computer-assisted methods for describing the likely folding conformation of a protein or portion of a protein, the method comprising the steps of (1), selecting a protein or portion of a protein to be described, (2), inputting into a computer the three-dimensional structure of the protein or portion of the protein from a source, wherein the source is a database, (3), dividing the protein or portion of the protein into overlapping elements, wherein each element consists of five consecutive amino acids, (4), identifying the five alpha carbon atoms in each element as the first alpha carbon atom, the second alpha carbon atom, the third alpha carbon atom, the fourth alpha carbon atom, and the fifth alpha carbon atom, (5), executing a calculation algorithm in the computer to compute a first torsion angle, a second torsion angle and a pitch distance, wherein the first torsion angle is the angle between a first plane and a second plane, wherein the first plane is defined by the first, second, and third alpha carbon atoms, and wherein the second plane is defined by the second, third and fourth alpha carbon atoms, wherein the second torsion angle is the angle between a third plane and a fourth plane, wherein the third plane is defined by the second, third and fourth alpha carbon atoms, and wherein the fourth plane is defined by the third, the fourth and the fifth carbon atoms, and wherein the pitch distance is defined by the distance between the first and the fifth alpha carbon atoms, (6), executing a range value algorithm in the computer to match the first torsion angle with a first torsion angle range value, the second torsion angle to a second torsion angle range value, and a pitch distance range value, wherein the first torsion angle range value is a member selected from the group consisting of $a_1$, $a_2$, and $a_3$, the second torsion angle range value is a member selected from the group consisting of $b_1$, $b_2$, and $b_3$, the pitch distance range value is a member selected from the group consisting of $c_1$, $c_2$, and $c_3$, and (7), executing an assignment algorithm in the computer to assign one vector to the element according to the values of $a_1$, $a_2$, $a_3$, $b_1$, $b_2$, $b_3$, $c_1$, $c_2$, and $c_3$.

In yet other embodiments of the present systems, methods and algorithms, the present invention provides for the comparison of two or more proteins, or portions of two or more proteins, as well as the design of proteins having desirable characteristics, or having characteristics analogous to those of model proteins.

The present invention includes also methods for comparing the likely conformation of a first protein to the likely conformation of a second protein, as well as for comparing the conformation of an actual protein to that of a theoretical protein

BRIEF DESCRIPTION OF THE DRAWINGS

In the accompanying drawings which form a part of the specification and are to be read in conjunction therewith and in which like reference numerals are used to indicate like parts in the various views:

FIG. 1 shows schematically a typical element of the invention consisting of 5 consecutive $C_\alpha$ atoms from the N-terminus to the C-terminus;

FIG. 2 shows schematically the two torsion angles in an element of the invention;

FIG. 3 shows schematically the pitch distance in an element of the invention;

FIG. 4 shows schematically the partitioning of the torsion angles and the pitch distance in an element of the invention;

FIG. 5 shows schematically the 27 Protein Folding Shape Code vectors of the invention;

FIG. 6 shows schematically the relationship of the PFSC vectors of the invention according to torsion angles and pitch distance;

FIG. 7 shows schematically the comparison of the PFSC and PDC methods in assigning secondary structures according to the invention;

FIG. 8 shows schematically the superimposed 3D structures of the 20 conformers of the oxidized form of E. coli Glutaredoxin (1EGO);

FIG. 9 shows schematically the frequency of appearance of PFSC vectors for the SALIGN Benchmark;

FIG. 10 shows schematically the Accessible Protein Folding Surface Code of the invention for the protein 1DOI;

FIG. 11 shows schematically the protein 1DOI showing protrusions from the surface;

FIG. 12 shows schematically the superimposed conformers of the Alzheimer amyloid β-peptide (1-42) peptide;

FIG. 13 shows schematically the UPFSM of the 30 conformers of the protein 1z0q according to the invention; and FIG. 14 shows schematically the UPFSM of the 30 conformers of the protein 1iyt according to the invention.

DETAILED DESCRIPTION OF THE INVENTION

Scientific efforts and research regarding the determination and prediction of protein structure research have essentially been focused on a group of approaches for attempting to describe the permutations of protein folding and related structural motifs. Although these aspects of the general scientific approaches are interrelated, these areas of inquiry can generally be organized into five areas of activity: (1) the use of thermodynamic descriptions involving energy calculations, computational dynamic simulations and the like; (2) the geometric determinations of structure from measurements obtained from experiments involving, for example, X-ray crystallography, NMR and the like; (3) geometric predictions directed toward using sequence homologues to predict the likely structure of a known or unknown protein; (4) geometric descriptions which are directed toward analyzing, describing and comparing protein structures; and (5) the utilization of databases and related algorithms as sources that store and analyze data for the purposes of facilitating the analyses of protein structure and function.

The Protein Folding Shape Code (PFSC) methods and algorithms of the present invention relate generally to all of these categories of analytic and descriptive activities. Moreover, the novel approach of the present methods systems and algorithms are especially relevant to the geometric analyses and descriptions of proteins from their respective sequences or sequence portions.

As an additional advantage, the PFSC algorithms and methods of the present invention have applicability beyond those relating to the determination of protein folding, shapes and other structural motifs. Indeed, the present methods, systems and algorithms are adaptable to describe, analyze and predict the folding and other three-dimensional aspects of the structures of biomolecules such as nucleic acids, carbohydrates and glycoproteins. As yet another advantage, the present invention is adaptable as a tool for describing the conformations of many other organic molecules.

This broad applicability of the present invention to many categories and classes of biomolecules and other organic molecules is especially suitable for use in the design of drugs, and the discovery and design of molecules which are to be adapted to interact with drugs. Such molecules include those with allosteric sites, such as proteins and glyco-proteins.

This invention is directed to methods, systems and algorithms that analyze and describe the aspects of conformation, such as shape and folding in the secondary and tertiary structures of proteins. The present methods, systems provide and utilize a set of 27 vectors to describe the protein shape, and therefore the 27 vectors are also known as the "protein folding shape code" (or "PFSC" hereinafter). The methods can thus be known as the "PFSC methods," the systems can also be known as the "PFSC systems," and the computer-based programs and algorithms can be referred to as the "PFSC Programs" or the "PFSC algorithms."

According to the invention, the 27 PFSC vectors are adapted and arranged to provide a comprehensive description of the folding shapes for fragment of 5 consecutive $C_\alpha$ atoms in protein. Provided with the Cartesian coordinates of the $C_\alpha$ atoms of the protein, a computer program, called the PFSC Program, will generate the PFSC as the description of the folding in the protein.

The present PFSC methods, systems and algorithms comprise significant improvements over previous methodologies in describing protein folding. The present invention possesses several unique characteristics. First, a set of 27 vectors is derived mathematically from an enclosed space, so 27 vectors reserve the all possible folding prototypes for a seamless description. The present PFSC methods, systems and algorithms offer ways of describing the folding of the $C_\alpha$ atoms in the protein backbone in a seamless manner.

Second, 27 PFSC vectors represent the folding patterns of five successive protein $C_\alpha$ atoms. Each PFSC pattern is not only a folding shape graphical prototype, but also a mathematical vector with specific folding characteristics attached at the N-terminus and the C-terminus. The 27 PFSC vectors of the invention are able to provide a meaningful description for protein structural assignment.

Third, the 27 PFSC vectors of the present methods, systems, and algorithms do not provide isolated folding patterns but are well associated with one another due to, among other features, their overlap in space and by their sharing of certain vector features. The present PFSC methods, systems and algorithms also describe the relationship of neighboring vectors and detect both gradual and abrupt changes in the three-dimensional relationship of the peptides of a protein being evaluated or analyzed according to the invention. It offers a meaningful interpretation of the three-dimensional aspects of conformation, such as shape and folding of the target protein or at least one portion of the target protein.

Fourth, the PFSC methods, systems and algorithms of the inventions are adapted and arranged to facilitate the conformational analyses of the three-dimensional structure of a protein or a portion of the protein. The present invention is thereby able to describe similarities or dissimilarities of different protein structures, and the similarities or dissimilarities of different conformers of the same protein. As an advantage over traditional superimposition approaches to protein analysis which typically utilize the measurement of root-mean-square deviation (rmsd), the present PFSC, and its related methods and algorithms, provides a supplemental tool useful for analyzing protein conformations, including the capacity for analyzing the details of localized local folding structures.

Fifth, the PFSC methods, systems and algorithms simplify the description of three dimensional folding of proteins by using a one-dimension string of PFSC vectors. The present PFSC methods thus offer a mathematical vector description of folding shapes along a protein backbone, which facilitates the description of the details of protein folding structure description for computer systems and databases.

Sixth, the PFSC method offers a complete and reliable description of folding shape along the protein backbone. With accurate and sensitive description of local fragment and global structure, the present PFSC algorithms and methods provide the fingerprint to identify protein 3D folding structures.

Seventh, according to the invention, the PFSC methods and algorithms can be applied to the analysis of protein misfolding with respect to structures related to diseases. Generated from the PFSC, the universal protein folding shape map ("UPFSM") can be used to interpret protein folding and misfolding data obtained from X-Ray crystallography or NMR spectroscopy experiment data. The UPFSM can simplify and display complicated protein 3-D structures as one-dimensional strings such that structural results from different experiments can be collected and aligned to form a the two-dimensional universal map which accounts for many factors. The location and the types of misfolding segments can therefore be accurately revealed and related to the corresponding experimental conditions with the utilization of the UPSFM.

Eighth, the PFSC methods, systems and algorithms are able to determine and describe expose the active amino acid residues in protein. To align protein folding shape code vector assignment (PFSCV) with the accessible protein surface code (APSC), the protein active sites along $C_\alpha$ atom backbones can be predicted.

Ninth, according to the invention, virtually all given three-dimensional protein structures are able to be assigned with appropriate values from the PFSC, and are able to e stored as part of a new database for PFSC-analyzed proteins, or portions thereof. Furthermore, by using the present means, methods and algorithms, additional databases can be constructed to demonstrate and analyze the correlations between and among five-amino acid elements and their consecutive sequence and folding structural features.

27 PFSC Vectors Represent 5 Consecutive $C_\alpha$ Atoms

Traditionally, a three-dimensional description of a set, or an element, of 5 consecutive $C_\alpha$ atoms in an amino acid chain of give residues would utilize the Cartesian coordinates of x, y, and z. Because of this, a minimum of 15 variables would necessarily be evaluated, or analyzed, in order to describe that set of 5 alpha carbons. In sharp contrast, the present methods, systems and algorithms according to the PFSC method provides novel, computationally efficient and advantageous coordinate transformation by focusing on certain attributes of the set, or the element, that are critical for describing the possible folding characteristics of the five consecutive $C_\alpha$ atoms, and then partitioning the space to obtain vectors selected from a group of 27 PFSC vectors.

There are two more salient factors why a chain of five $C_\alpha$ atoms of an amino sequence are selected as an element upon which a PFSC vector is determined. First, in a typical protein, the secondary structure is formed by repeating conformation unit with a certain number of residues. The numbers of residues per repeating conformation units having a certain number of amino acid residues. The number s of residues per repeating unit or turn are generally well known, such as two $C_\alpha$ atoms for β-strand, 3.6 for right-handed or left-handed α-helix, two for $2.2_7$ helix, three for $3_{10}$ helix, 4.3 for δ-helices, 4.4 for π-helix and 5.1 for γ-helix. The element length from which a vector is determined should therefore span at least one complete repeating conformation of a typical secondary structure at unit. Second, the fragment of any five successive $C_\alpha$ atoms comprising a give amino acid chain has two adjunctive torsion angles. These two torsion angles will provide the information necessary and sufficient to describe a repeating or discontinuous folding pattern, while allowing a simplification, or lowering, of the number of variables which must be considered in order to efficiently describe the continuance of shapes. Therefore, the present PFSC methods, systems and algorithms utilize data regarding the five $C_\alpha$ atoms of a sequence of five amino acids as a basic unit to be evaluated in order to describe the possible folding shape, or conformations that can be expected to produce an appropriately accurate description or prediction for the proteins folds and other conformational characteristics.

The Shape Characteristics of PFSC

To describe possible conformations, such as the likely shape into which a protein, or a portion thereof, is likely to fold, the PFSC methods, systems and algorithms take into account of the geometric, morphological and topological aspects of the likely and possible protein structures. The PFSC method fulfills the criteria for shape description by addressing the issues of scope, uniqueness, stability, sensitivity, efficiency, multi-scale and local explanation as discussed before. Therefore, the present PFSC methods, systems and algorithms are advantageous in the analysis of secondary and tertiary protein structures, including regular fragments and irregular loops. Also the present PFSC methods, algorithms, and systems are able to offer rich and valuable information to comprehensively describe the possible and likely protein folding structures in detail.

In the present methods and systems, 27 PFSC vectors are derived mathematically from an enclosed space. One of these 27 vectors represents the possible prototypes of folding shapes of any sequence of five consecutive $C_\alpha$ atoms of an amino acid sequence or protein. The 27 vectors are represented by 26 alphabetic letters in uppercase and '$' sign. Also each vector carries specific folding characteristics at N- and C-termini as starting and ending points for the vector.

Protein Structure Vs. Shape

There are advantages to describe a protein or a segment of a protein, as a folded structure or shape in an enclosed three-dimensional space. Shape presents salient geometrical information about an element or segment which remains unaffected, while information about the location, scale, and rotational effects can be filtered out from a shape object (Kendall, D G, Advances in Applied Probability, 1977, 9: 428-430). The shape information of the geometry should be invariant to Euclidean transformations (Iyer N, Jayanti S, Lou K Y, Kalyanaraman Y, Ramani K., Proceedings of the TMCE 2004, Apr. 12-16, 2004, Lausanne, Switzerland, Edited by Horvath and Xirouchakis, @ 2004 Millpress, Rotterdam).

A shape, $S_i$, can be represented as a collection, or a set, of attributes:

$$S_i = \{a_1^i, a_2^i, \ldots, a_n^i\}$$

wherein $(a_n^i)$ is a component of attributes for shape object of i.

The similarity between two shapes $S_i$ and $S_j$ can be expressed as, $$S_i \sim S_j = \sum_{m=1}^{n} |a_m^i(d_i) \sim a_m^j(d_j)|$$

wherein $d_i$ and $d_j$ denote the protein coordinates in terms, and the symbol "~" denotes the operation of comparison between two attributes. The similarity should be a collective result of n terms of comparison of each corresponding attribution component starting from m=1. Furthermore, the shape can be represented as different viewing aspects, such as geometric, morphological and topological aspects (Iyer N et al.).

The three-dimensional coordinates of the protein structure according to the PDB contain the complete and accurate geometric information of shape in space. The geometric aspect of the shape is a set $S_G$ of all points $P_j$, $$S_G = \bigcup_{P_j \in R^3} P_j$$

Wherein $P_j \in \Re^3$ builds up the physical extent of a shape and j is index of atoms. However, the protein folding structure is not adequately described by only the atomic coordinates.

To further characterize the folding structural features, the shape of the protein can be represented with morphological aspect that considers similar loops and segments. The morphological aspect of a protein shape $S_M$ is a set of $\{Z_k\}$, which is composed of subsets $Z_k$ for points $P_j$ so that it can be expressed as:

$$S_M = \bigcup_{k=1}^{n} Z_k, Z_k = \bigcup_{P_j \in Z_k} P_j$$

wherein k is index of family and j is index of atoms.

With the secondary structural as the basic fragments to study the protein structural similarity, many methods actually took the morphological feature to describe the protein folding structures (Holm L, Sander C, J. Mol. Biol., 1993a; 233: 123-138; Gerstein M, Levitt, M, In Proc. Fourth Int. Conf. on Intell. Sys. for Mol. Biol. Menlo Park, Calif.: AAAI Press. 1996. p 59-67; Gibrat J F, Madel T, Bryant S H, Curr. Opin. Struct. Biol. 1996; 6:377-385; Singh A P, Brutlag D L, In Proc. Fifth Int. Conf. on Intell. Sys. for Mol. Biol. Menlo Park, Calif.: AAAI Press. 1997. p 284-293; Singh A, Brutlag D, http://gene.stanford.edu/3dSearch; Shindyalov I N, Bourne P E. Protein Eng. 1998; 11(9):739-47; Krissinel E, Henrick K, Acta Crystallogr D Biol Crystallogr. 2004; 60(Pt 12 Pt 1):2256-2268; Balaji S, Sujatha S, Kumar S S C, Srinivasan, N, Nucleic Acids Res. 2001; 29:61-65; Park J H, Ryu S Y, Kim C L, Park I K J, Genome Informatics 2001; 12:350-351; Hadley C, Jones D T, Structure. 1999; 7(9):1099-112; Kabsch W, Sander C, Biopolymers. 1983, 22: 2577-2637; Ridchards F M, Kundrot C E. Proteins. 1988, 3:71-84; Frishman D, Argos P, Proteins. 1995, 23: 566-579; Sklenar H, Etchebest C, Layery R, Proteins. 1989, 6: 46-60; Labesse G, Colloc'h N, Pothier J, Mornon J P, Comput. Appl. Biosci. 1997; 13(3):291-5; and Martin J, Letellier G, Marin A, Taly J F, de Brevern A G, Gibrat J F, BMC Struct. Biol. 2005; 5:17, all of which are hereby incorporated by reference).

In addition, the protein shape can be represented from the perspective of topology because the $C_\alpha$ atom backbone is a topological object. Therefore, a protein backbone can be represented as $S_T$ in term, which is a Hausdorff space (Iyer N et al) because each $C_\alpha$ atom has the neighborhood relation to other $C_\alpha$ atoms. The topological shape of a protein is $S_T$ in which each point $t_i \in S_T$ has a neighborhood homeomorphic to $\Re^3$, so that $$S_T = \bigcup_{i=1}^{\infty} (t_i)$$

wherein $U(t_i) \geq 0$, and it is the number of neighborhoods of point $t_i$. There are other methods that employed the topological aspect to describe the protein structures (Kabsch, W, Acta Crystallogr. A 1978; 34:827-828; Holm L, Sander C, J Mol Biol. 1993; 5; 233(1):123-38; Flower D R, Protein Eng. 1998; 11(9):723-7; Murzin, A., Conte, L. L., Andreeva, A., Howorth, D., Ailey, B., Brenner, S., Hubbard, T., and Chothia, C, http://scop.mrc-lmb.cam.ac.uk/scop/intro.html; Pedro A. De-Alarco'n, Alberto Pascual-Montano, Amarnath Gupta, and Jose M. Carazo, Biophysical Journal 83 (2), 2002, 619-632; Lindorff-Larsen K, Vendruscolo M, Paci E, Dobson C M, Nature Structural & Molecular Biology, 2004: 11, 443-449; Sunyaev S R, Bogopolsky G A, Oleynikova N V, Vlasov P K, Finkelstein A V, Roytberg M A, Proteins, 2004: 54, 569-582; Carugo O, Pongor S, J. Mol. Biol. 2002; 315, 887-898; Jung J, Lee J, Moon H T, Proteins. 2005: 58:389-95, all of which are hereby incorporated by reference).

In summary, one known way of describing proteins is to use their three-dimensional atomic coordinates to provide accurate geometric information and thereby present the protein structural images in space. Some conventional methods studied the secondary structures and similar segments to explore the duplicate structural fragments in proteins by utilizing the morphological features to characterize the proteins' three-dimensional structures. Other conventional methods took the approach of connecting the $C_\alpha$ atoms to emphasize the neighboring environments along the protein backbone. In contrast, the present methods, systems and algorithms of the PFSC invention optimally integrate salient features of these approaches while providing novel and additional ways of gleaning data into more simplified calculations to thereby yield a superior approach to describing proteins with respect to their $C_\alpha$ atom backbone and their consequent likely and possible folding shapes.

Criteria for Shape Representation

To study and compare complex shapes, a high-quality shape description must meet certain criteria as recommended by many researchers (Iyer N et al.; Marr D, Nishihara H K., Proceedings of the Royal Society of London: Part B. 1978, 200: 269-294; Woodham R J. In: Computational Processes in Human Vision, Ed. By Z. Pylyshyn, Norwood, N.J. 1987; and Brady M. In: Human and Machine Vision, Eds. Beck J, Hope B, Rosenfeld A. Academic Press. 1983 p 39-84, all of which are hereby incorporated by reference). A good shape description must simultaneously consider several factors such as scope, uniqueness, stability, sensitivity, efficiency, multi-scale and local support. The present algorithms, systems and methods of the PFSC invention offer an improved protein folding shape description by using an algorithm that meets these criteria mathematically while decreasing computation time.

Scope: The shape representation must be able to describe all the variations of protein folding shapes. The PFSC is a comprehensive method because it uses an algorithm that covers virtually all types of folds of protein $C_\alpha$ atom backbone, including the common secondary structures and various loops from super secondary to tertiary structure.

Uniqueness: The shape representation should give unique descriptions of proteins so that any two different protein sequences would not have the same representation. The present PFSC methods, systems and algorithms aim at giving each protein structure a sole shape code as its structural fingerprint.

Stability: For each individual protein, the shape representation must be stable to small changes of shape so that small changes in shape will produce only small changes in the description. The present PFSC methods, algorithms, and means allow certain tolerances for small changes among similar proteins so that the structural similarity among these proteins can be identified.

Sensitivity: The shape representation must be sensitive enough to capture even subtle changes in the protein shape. The PFSC methods, algorithms and systems are designed to be able to detect the details of dissimilarity among similar protein sequences and structures.

Efficiency: The shape representation should be efficient in computation and analysis. The present PFSC methods and systems use a simplified algorithm that computes and analyzes all possible protein folds with efficiency. Also the present PFSC methods and systems offer a simple means to label and compare protein folding shapes.

Multi-scale capability: The shape representation is required to describe a shape at multiple scales. First, the present PFSC methods and systems define the protein secondary structural elements with consistence of results from X-ray and NMR experiment data. Second, the present PFSC methods and systems provide descriptions of virtually all irregular turns and loops for protein tertiary structures. Third, the same piece of fragment of the PFSC is kept same result disregarding the calculations using protein fragment only or entire protein.

Local illumination: The shape representation must describe local fragment structural information for proteins. First, the present PFSC algorithms, systems and methods are able to consistently describe any piece of fragment independently from entire protein. Secondly, the present PFSC algorithms, systems and methods offer ability to further analyze the local influence from intervening neighboring segments on any given element or sequence.

Vector Transformation

According to this invention, each 5 consecutive $C_\alpha$ atoms of protein backbone is chosen as an "element" for protein backbone folding shape which is shown in FIG. 1.

As it is well known in the art, an amino acid is a basic unit in a protein. In each amino acid, there is an "alpha carbon atom" ($C_\alpha$) that is connected to an amino group (—$NH_2$), a carboxyl group ($CO_2H$), a hydrogen atom, and a side chain. In a dipeptide, the carboxyl group of the first amino acid is connected to the amino group of the second amino acid to form an amide bond. As a result, in the dipeptide, the amino group of the first amino acid is the N-terminus and the carboxyl group of the second amino acid is the C-terminus. In a polypeptide, the amino group of the first amino acid is the N-terminus, and the carboxyl group of the last amino acid is the C-terminus. For this invention, unless otherwise indicated, the alpha carbon atoms of the amino acids in the backbone of a protein, or portion thereof, are oriented from the N-terminus to the C-terminus.

According to the present invention, an "element" is a group of five consecutive alpha-carbon ($C_\alpha$) atoms along the backbone of a protein in the direction from the N-terminus to the C-terminus. For each element, "n−2" is the first alpha carbon, "n−1" is the second alpha carbon, "n" is the third alpha carbon, "n+1" is the fourth alpha carbon, and "n+2" is the fifth alpha-carbon.

The "center of the element" is the third alpha carbon of the element. When it is necessary to compare the linear amino acid sequence of the protein with the linear vector sequence, the vector for the element consisting of the "n−2" alpha carbon atom through the "n+2" alpha carbon atom can be aligned with the "$n^{th}$" amino acid in the linear amino acid sequence.

According to the present invention, the elements of a protein or portion thereof are overlapping such that each succeeding element of the protein overlaps the preceding element by four amino acids. For example, for a protein of 10 amino acids where the amino acids are numbered 1-10, the first element would consist of amino acids 1-5, the second element would consist of amino acids 2-6, the third element would consist of amino acids 3-7, the fourth element would consist of amino acids 4-8, the fifth element would consist of amino acids 5-9, the sixth element would consist of amino acids 6-10.

The shape of each group of 5 consecutive protein $C_\alpha$ atoms is defined as a vector, "v", which is determined by the three-dimensional atomic coordinate (x, y, z), having a total 5×3=15 components in the Cartesian coordinate system.

$$v=(x_1,y_1,z_1,\ldots,x_5,y_5,z_5)$$

Because vectors are invariant to the transformation of coordinate systems, changing the coordinate system may change the magnitudes of the components in the new system but not the vector itself. Under a new coordinate system, the vector of 5 consecutive $C_\alpha$ atoms is invariant and keeps same number of components. The new coordinate system is designed to reveal the attributes of the folding characteristics of 5 consecutive $C_\alpha$ atoms. In this new coordinate system, the vector for 5 consecutive $C_\alpha$ atoms is composed of 15 new independent components: 3 components for the vector absolute location in space, 2 for the orientation token by the vector, 4 for the distances between two adjacent $C_\alpha$ atoms, 3 for the angles of three adjacent $C_\alpha$ atoms, 2 for the torsion angles of four adjacent $C_\alpha$ atoms and 1 for the pitch distance between the two ending $C_\alpha$ atoms. The vector under the new coordinate system is expressed as, $$V=(\tau_1,\tau_2,\tau_3,\ldots,\tau_{13},\tau_{14},\tau_{15})$$

The new vector can be obtained by coordinate transformation from the Cartesian coordinates system:

$$\begin{pmatrix} t_{11} & t_{12} & \ldots & t_{15} \\ t_{21} & t_{22} & \ldots & \ldots \\ \ldots & \ldots & t_{ij} & \ldots \\ t_{151} & \ldots & \ldots & t_{1515} \end{pmatrix} \begin{pmatrix} x_1 \\ y_1 \\ \ldots \\ z_5 \end{pmatrix} = \begin{pmatrix} \tau_1 \\ \tau_2 \\ \ldots \\ \tau_{15} \end{pmatrix}$$

wherein $t_{ij}$ is an element in the transformation matrix. As a result of this transformation, the weight of contribution for folding shape description is redistributed among each component of the vector. Emphasizing the characteristics of shape, the components for the location and the orientation do not directly have contribution to the shape of folding in the protein structures. The components of the distances between adjacent $C_\alpha$ atoms and the angles of adjacent 3 of $C_\alpha$ atoms are relatively stable as constants, because they do not make much contribution to the protein folding shape. However, the remaining 3 components among the components make the most essential contributions to the shape of the folding in the protein structures. They are the 2 components for the torsion angles for each of four adjacent $C_\alpha$ atoms and the 1 component for the pitch distance between two ending $C_\alpha$ atoms.

As shown in FIG. 1, for the 5 consecutive $C_\alpha$ atoms ranging from (n−2), (n−1), n, (n+1) to (n+2), the two torsion angles of four adjacent $C_\alpha$ atoms can be represented by τ(n−2, n−1, n, n+1) and τ(n−1, n, n+1, n+2). As a combination, these two torsion angles describe the folding element of 5 successive $C_\alpha$ atoms.

In the context of the present invention, a "torsion angle" is defined with respect to a group of four consecutive alpha carbon ($C_\alpha$) atoms of four amino acids. The torsion angle with respect to the four alpha carbons is that angle between a plane formed by the first three alpha carbon atoms, and another plane formed by the last three of the four alpha carbons. Thus, for each element of five alpha carbon atoms, there are two torsion angles: a "first torsion angle" defined by the first, second, third and fourth alpha carbon atoms; and a "second torsion angle" defined by the second, third, fourth and fifth alpha carbon atoms.

As illustrated in FIG. 2 (A), a "first torsion angle" is the angle between a first plane and a second plane, where the first plane is defined by the first, second and third alpha carbon atoms, and the second plane is defined by the second, third and fourth alpha carbon atoms. As illustrated in FIG. 2 (B), a "second torsion angle" is the angle between the second plane and a third plane, the third plane being defined by the third, fourth and fifth alpha carbon atoms.

As illustrated in FIG. 3, a "pitch distance" is defined by the first and last of the five consecutive alpha carbon atoms in an element. The pitch distance is the distance between the first and the fifth alpha carbon atoms, expressed in Angstroms.

Within each element, taken together, the first torsion angle and the second torsion angle contribute values toward describing the shape, or conformation, of the element. Thus, the two torsion angles of a given element may indicate a pattern of continuity, such as an α-helix or a β-strand, or a pattern of interruption, such as an irregular turn or a loop. In addition, the distance between two ending $C_\alpha$ atoms, τ(n−2, n+2) expresses a value regarding the overall shape, or conformation, of an element of 5 successive $C_\alpha$ atoms. An advantage of the present invention is that only these three values are necessary in order to characterize the conformation or folding shape of a five amino acid element. With just these three values, a three-dimensional vector expressing the folding shape of five successive $C_\alpha$ atoms in three-dimensional space is obtained.

With the three-dimensional vector, the description of protein folding shapes is greatly simplified. Any three-dimensional vector can be represented as below.

$$V(a,b,c) = V(aA, bB, cC) = aA + bB + cC$$

Here A, B and C denote components a, b and c, which are magnitudes of each component. According to vector properties, A, B and C must be the independent components.

$$A \times B \neq 0, B \times C \neq 0, A \times C \neq 0$$

According to the PFSC method, the two adjacent torsion angles for each 5 consecutive $C_\alpha$ atoms and the pitch from the $C_{\alpha(n-2)}$ to the $C_{\alpha(n+2)}$ atom are defined as independent components. The corresponding scales a, b and c for each component can be calculated based on the $C_\alpha$ atomic coordinates. The angles of the two adjacent torsion angles for each 5 consecutive $C_\alpha$ atoms and the pitch between the $C_{\alpha(n-2)}$ and the $C_{\alpha(n+2)}$ atoms are expressed as:

$$a = \tau(r_{n-2}, r_{n-1}, r_n, r_{n+1}) = \bigcup_{i=n-2}^{n+1} F(x_i, y_i, z_i)$$

$$b = \tau(r_{n-1}, r_n, r_{n+1}, r_{n+2}) = \bigcup_{i=n-1}^{n+2} F(x_i, y_i, z_i)$$

$$c = \tau(r_{n-2}, r_{n+2}) = \bigcup_{i=n-2, n+2} F(x_i, y_i, z_i)$$

wherein, a and b are two torsion angles for each set of 5 consecutive $C_\alpha$ atoms, c is the distance between the $C_{\alpha(n-2)}$ and the $C_{\alpha(n+2)}$ atoms, and F is the polynomial function to calculate torsion angle and distance with using $C_\alpha$ atom coordinates (x, y, z) which are obtained from protein data bank (PDB). The $r_n$ denotes the coordinate of atom n. It is apparent that the 15 coordinate variables (x, y, z) of the 5 consecutive $C_\alpha$ atoms are now reduced to 3 components of vector V in space to represent its folding shape.

Segregation of Vector Space

An ideal description of the folding shape of protein is the ability to study the similarity as well as the dissimilarity of protein structures. At the molecular scale, a vector can describe the continuous change infinitely in space, which is a reliable representation of shape of protein fragment. Any protein structural difference is reflected with these representations. In order to describe the similarity of protein structures, some tolerances on numerical measurement should be allowed. For this reason, the space for vector is segregated, which changes a vector from continuous to discrete and from infinite to finite.

According to the PFSC methods, systems and algorithms of the invention, each of the values for the two torsion angles for a five consecutive $C_\alpha$ atom element, and the value of the pitch distance between the $C_{\alpha(n-2)}$ and the $C_{\alpha(n+2)}$ atoms are combined and partitioned into three regional zones. Each of these combinations of three values corresponds, or sums, to a vector. Each of the possible shape elements of every five successive $C_\alpha$ atom element of a protein backbone corresponds to one of 27 possible vectors. The 27 vectors are obtained or derived as follows:

$$V(a,b,c) \supseteq \sum_{i=1}^{3} \sum_{j=1}^{3} \sum_{k=1}^{3} (a_i A + b_j B + c_k C)$$

Because the pitches of the 4 consecutive $C_\alpha$ atoms segments for many common secondary structures are well known (see Ghelis C, Yon J. Molecular Biology: Protein Folding. New York, London: Academic Press; 1982; Labesse G, Colloc'h N, Pothier J, Mornon J P, Comput. Appl. Biosci. 1997, 13(3):291-5; and Martin J, Letellier G, Marin A, Taly J F, de Brevern A G, Gibrat J F., BMC Struct Biol. 2005, 5: 17, all of which are hereby incorporated by reference), the scale of vector between the $C_{\alpha(n-2)}$ atom and the $C_{\alpha(n+2)}$ atoms can easily be defined for the pitch distance of 5 consecutive $C_\alpha$ atoms.

According to the present invention, the first and the second torsion angles and the pitch distance can be partitioned into different zones, or range values. The use of different zones or range values is helpful in describing the shape and conformation of the protein or a portion of a protein. In one embodiment, the range values for the first torsion angle can be selected from one of the following ranges: range $a_1$, $a_2$ and $a_3$, where $a_1$ can be 0° to 160°, $a_2$ can be +120° to −120°, and $a_3$ can be −160° to 0°. Similarly, the range values for the second torsion angle can be selected from one of the following ranges: range $b_1$, $b_2$ and $b_3$, where $b_1$ can be 0° to 160°, $b_2$ can be +120° to −120°, and $b_3$ can be −160° to 0°. The range values for the pitch distance can angle can be selected from one of the following ranges: range $c_1$, $c_2$ and $c_3$, where $c_1$ can be 0 to 7.0 Å, $c_2$ can be 4.0 Å to 17.0 Å, and $c_3$ can be greater than 17.0 Å.

A particular embodiment for the present invention can be summarized in FIG. 4. According to this embodiment, the partition boundaries attempt to avoid separating currently known folding motifs into different regions. Accordingly, $a_1$ and $b_1$ can be 0° to 130°; $a_2$ and $b_2$ can be >130° to 180° and −180° to −130°; $a_3$ and $b_3$ can be >−130° to 0°. The pitch distance (c) between $C_{\alpha(n-2)}$ and $C_{\alpha(n+2)}$ for five conjunctive $C_\alpha$ atoms can be partitioned into three regions, or range values, i.e. $c_1$ at <5.5 Å, $c_2$ at >5.5 Å to 14.0 Å, and $c_3$ at >14.0 Å. Under this partitioning approach, the folding motifs α-helix, β-strand, γ-helix and π-helix, π-helix, and $3_{10}$ helix and $2.2_7$ helix fit into five different regions. In summary, the 27 PFSC vectors can be obtained by mathematical process based on shape object, and the characteristics of protein structures are considered.

Protein Folding Shape Code (PFSC)

In the PFSC method, the 27 vectors can be represented by 26 alphabetic letters in uppercase and '$' sign. A letter is assigned to the center atom of five consecutive $C_\alpha$ atoms for each vector. The 27 vectors stand for possible folding shapes, and each vector carries specific folding characteristics at N- and C-termini as starting and ending points for the vector.

In the PFSC method, the folding shape patterns of the 27 vectors and the associated characteristics are shown in FIG. 5. Here the three blocks represent three regions of pitch distance, and nine vectors in each block represent the nine folding shape patterns which are the results as two torsion angles change into different zones. A vector is able simultaneously to be represented by three formats, a letter, a folding shape pattern and an arrow line.

In the PFSC method, the specific folding features associated with each vector are listed in Table I. A vector may have multiple features while the same feature may relate to more than one vector. In Table I, for instance, the vector "J" has α-helix characteristics at the N-terminus but β-strand characteristics at the C-terminus. It is an analogous vector for both α-helix and β-strand, it can cap α-helix C-terminus or β-strand N-terminus, and it locates at pitch distance block $c_2$. In another aspect, the α-helical feature at C-terminus related to nine vectors, such as "A", "D", "H", "U", "V", "W", "X", "Y" and "Z".

TABLE I

The metric of 27 PFSC vector characteristics

| PFSC Vector | A | B | C | D | E | F | G | H | I | J | K | L | M | N | O | P | Q | R | S | T | U | V | W | X | Y | Z | $ |
|---|---|---|---|---|---|---|---|---|---|---|---|---|---|---|---|---|---|---|---|---|---|---|---|---|---|---|---|
| α-helix | X | | | | | | | | | | | | | | | | | | | | | | | | | | |
| β-strand | | X | | | | | | | | | | | | | | | | | | | | | | | | | |
| Analogous to α-helix | | | X | | | | | X | | X | | | | | | | | | | | X | | X | | | | |
| Analogous to β-strand | | | | X | X | | | X | | | | | X | | | | | | X | | | X | | | | | |
| Pitch distance $c_1$ | | | | X | | X | | | X | | X | | X | | X | | X | | X | | | | | | X | X | |
| Pitch distance $c_2$ | X | X | X | | | | | X | | X | | X | | X | | X | | X | | | X | | X | | | | |
| Pitch distance $c_3$ | | | | | X | | X | | | X | | | | | | | | | X | X | | X | | X | | | |
| α-helical at C-terminus | X | | | X | | | | X | | | | | | | | | | | | | X | X | X | X | X | X | |
| α-helical at N-terminus | X | | | X | | | | | X | X | X | X | | X | X | X | | | | | | | | | | | |
| β-strand at C-terminus | | X | | X | | X | | | | X | X | X | | | | | | X | X | X | | | | | | | |
| β-strand at N-terminus | | X | | | X | X | | | | | | | X | X | X | | | | | | | X | X | X | | | |
| Irregular at C-terminus | | X | | | X | | | | | | X | X | X | X | X | X | | | | | | | | | | | X |
| Irregular at N-terminus | | X | | | X | | | | | | | | | | | X | X | X | | | | | X | X | X | X | |
| Cap α-helix N-terminus | | | | | | | | X | | | | | | | | | | | X | | | | | X | X | | |
| Cap α-helix C-terminus | | | X | | | | | X | | X | | | | X | X | | | | | | | | | | | | |
| Cap β-strand N-terminus | | | | | | | | X | X | X | | | | | | | | | X | | | | | | | | |
| Cap β-strand C-terminus | | | | | | | | X | | | | | | | | | | | | X | X | X | | | | | |

1. The first row lists 27 PFSC vectors.
2. The left column lists the characters of PFSC vectors.
3. The "X" indicates the characteristics associated with each vector.
4. The definition of pitch distance $c_j$ refers to FIG. 6.
5. The background colors group the characteristics.

In the PFSC method, the relationship for 27 vectors is shown in FIG. 6. The three-dimensional arrangement displays the integral relationship of the 27 PFSC vectors. Three axes of a, b and c represent three components, i.e. two torsion angles and one pitch distance. Each component is partitioned into three ranges, which creates the 27 PFSC vectors. Each vector associates to other vectors in horizontal and vertical directions. Also, a vector shares certain folding features with the surrounding vectors. In addition, the horizontal layer or the vertical slice groups the vectors with same features. Therefore, the 27 vectors are not the isolated folding patterns, and they are closely associated each other in space with a relation diagram in FIG. 6.

In the method of the present invention, a vector describing a five amino acid element of a protein is determined by three input values with respect to the five alpha carbons of that element. These three input values relate to the first and second torsion angles, and a value for the pitch distance between the first and fifth alpha carbons.

With the present method, the three-dimensional conformation for any given five amino acid element can be described, that is, approximated, by combining these three values to arrive at one vector out of a possible 27 PFSC vectors. Each of these vectors are determinable with respect to the ranges of values regarding the three input values. Thus, no pair of two PFSC vectors should have three components the same. Instead, the two vectors may have one, or two, components in the same value range. Having one or two components in the same value range indicates, in one aspect, the degree of similarity between the two vectors. These similarities are represented diagrammatically in the 3-dimensional matrix of FIG. 6.

In FIG. 6, the nine vectors in each horizontal layer have a value range in common, i.e., they all have the same pitch distance value range with respect to three-dimensional space. For instance, all of nine vectors "Y," "V," "A," "S," "B," "J," "C," "M" and "P" in the middle horizontal layer have the same pitch distance value range block of $c_2$. Other commonalities are also shown in the matrix of FIG. 6. For example, the nine vectors in any vertical slice shown in FIG. 6 have one component value the same, i.e. they belong to the same value range for one of two torsion angles. For example, each of the nine vectors "X," "U," "H," "Y," "V," "A," "Z," "W" and "D" in one vertical slice of the matrix have the first torsion angle range of $a_1$.

Closer similarities are shown as "analogies." Thus, if a first vector has two of three input values components in same distribution range as that of a second vector, the two vectors are analogous. For example, vector "A" is defined by three input value components ($a_1$, $b_1$, and $c_2$) as is shown in the matrix of FIG. 6. Vector "A" therefore has six analogous vectors: "J," "P," "V," "Y," "H" and "D." Vectors "V" and "Y" are also analogous to "A" because each of "V" and "Y" are determined partly by the two input values $c_2$ and $a_1$. Similarly, vectors "J" and "P" are also analogous to "A" because each have both of the input values $c_2$ and $b_1$. Moreover, vectors "H" and "D" are also analogous to "A" since each have both of the range values $a_1$ and $b_1$. Similarly, vector "B" has six analogous vectors to "V," "M," "S," "J," "E" and "G" because the vectors "V" and "M" each have $c_2$ and $b_2$, as input values, the vectors "S" and "J" each have $c_2$ and $a_2$ as input values, and vectors "E" and "G" each have $a_2$ and $b_2$, as input values, as does vector "B." In a related aspect, each vector in the middle layer correlates to six analogous vectors. In contrast, each vector in the top and bottom layers has five analogous vectors.

In the PFSC method, by using an arrow, the folding features at initial and terminal points of a vector represent the characteristics of the N- and C-termini respectively. Three types of folding features, which are similar to α-helix, β-strand and irregular coil, are marked at each end of a vector as "α", "β" and "*". They represent the folding angular distribution along the vector direction. For instance, "A" has α-helical features at both the N- and the C-termini; "B" has β-strand features at both the N- and the C-termini; "J" has α-helical feature at the N-terminus but β-strand feature at the C-terminus; "V" has α-helical feature at the C-terminus but β-strand feature at the N-terminus; "H" has α-helical feature at both the N- and the C-termini. Therefore, the PFSC folding patterns are not only distinguished by 27 alphabetic letters, but also by vectors characteristics.

In the PFSC method, the 27 PFSC vectors are associated with each other by sharing certain vector features. For instance, "A", representing an α-helix, is a vector in block 2 (i.e. range $c_2$) of the pitch distance range value, zone 1 (i.e. range $a_1$) of the first torsion angle range value, and zone 1 (i.e. range $b_1$) of the second torsion angle range value. "B", representing a β-strands, is a vector in block 2 (i.e. range $c_2$) of the pitch distance range value, zone 2 (i.e. range $a_2$) of the first torsion angle, and zone 2 (i.e. range $b_2$) of the second torsion angle range value. "J" is a neighbor to both "A" and "B" because "J" has α-helix characteristics at the N-terminus but β-strand at the C-terminus. "V" also a neighbor to both "A" and "B", but "V" has β-strand characteristics at the N-terminus but α-helix characteristics at the C-terminus. "H" is a neighbor of "A" because, like "A," it has α-helix characteristics at both the N- and the C-termini. However, "H" has a larger pitch distance. Therefore, each of the 27 PFSC vectors is helpful in describing the characteristics of folding and conformation because the characteristics at both termini can be identified.

Because the PFSC method offers a seamless description for all loops of protein structures, it has the ability to cover 100% of folding shapes along the protein $C_\alpha$ atoms backbone, including regular secondary structural fragments, and irregular and the rare observed structural fragments, and even those that are unfavorable in terms of the stability of the protein structures. In protein, there are many of irregular bends, coils, turns or loops, and it is especially hard to describe and distinguish them clearly. Particularly for loops with rare appearance, it is difficult to find out them and gives statistic survey results. Also it is quite complicated to describe how these irregular fragments connect together with the regular secondary structure fragments of α-helices and β-strands of. According to this invention, the PFSC algorithm treats all possible folds equally and describes the relationship of folds along protein $C_\alpha$ atoms backbone. So the irregular fragments of protein folding shapes can be described and classified by the PFSC method.

As a computer-implemented method, the PFSC algorithm is coded in Java (J2SE v.1.5.0_07). Its license belongs to MicrotechNano, LLC. Requests to calculate the PFSC for specific proteins can be sent by e-mail to info@proteinshape.com or via Website: http://www.proteinshape.com.

The PFSC method is able to describe the folding motifs of protein given their 3D structures or 3D coordinates. Because the PFSC method only considers the alpha carbon atoms, it can handle even low resolution data obtained from X-ray and NMR. Most of 3D structures of proteins are deposited into the Protein Data Bank (PDB), and are publicly available. The Worldwide Protein Data Bank ("wwPDB") (see http://www.wwpdb.org/) provides access to RCSB PDB (USA) (http://www.rcsb.org/pdb/home/home.do), MSD-EBI (Europe) (see http://www.ebi.ac.uk/msd/), PDBj (Japan) (see http://www.pdbj.org/), and the Biological Magnetic Resonance Data Bank (BMRB) (USA) (see http://www.bmrb.wisc.edu/). In addition, the National Center for Biotechnology Information Molecular Modeling Database (NCBI MMDB) also provides computational structure of proteins (see http://www.ncbi.nlm.nih.gov/Structure/MMDB/mmdb.shtml).

According to the invention, given three-dimensional data of a protein or portion thereof, the PFSC algorithm can be executed to generate the vectors, or the PFSC code, for a target protein or a portion of the target protein. The PFSC algorithm comprises a sequence of steps: (A) dividing the protein into a series of overlapping elements, each element having five amino acids, and with respect to a first element, (B) determining a range value for a first torsion angle, (C) determining a range value for a second torsion angle, (D) determining a range value for a pitch distance, and (E) combining the range values obtained from Steps B, C and D to obtain a first element vector.

The PFSC algorithm further comprises the steps with respect to a second element: (F) repeating Step A to the second element, (G) repeating Step B to the second element, (H) repeating Step C to the second element, (I) repeating Step D to the second element, and (J) combining the range values obtained from Steps G, H, and I to obtain a second element vector.

The PFSC algorithm further comprises Step (K), repeating Steps (F), (G), (H), (I) and (J) with respect to at least a portion of the target protein, and Step (L), repeating Steps (F), (G), (H), (I) and (J) with respect to the entire target protein.

The PFSC algorithm further comprises Step (M), applying one or more algorithms to the set of Vectors to determine one or more aspects of the conformation of the target protein.

The PFSC method provides a new tool to describe protein folding from secondary structures to tertiary structures. The PFSC presents a systematic description for folding shapes along the protein backbone. Also, the PFSC offers the information to reveal protein folding structure in detail and shape transition, and it provides the justification for length, boundary and distortion of secondary structures.

With a given 3D protein structure as input, a computer program has been developed to generate the PFSC as output for protein folding shape description. What follows in this section is an examination of PFSC results and a comparison to other well established methods. First, the PFSC is calculated for a collection of protein structures randomly selected from the PDB. This includes protein structure belonging to different classifications, and those having multiple conformers of the same protein. Second, using PFSC the structural assignments are assessed for the established SALIGN benchmark. (Marti-Renom M A, Madhusudhan M, Sali A. Alignment of protein sequences by their profiles. Protein Sci 2004; 1071-1087) Finally, the PFSC results are compared with the secondary structure assignments found in the PDB, as well as the assignments from other methods.

EXAMPLES

The following Examples are merely illustrative of certain embodiments of the invention and contain comparisons of compositions and methods according to the invention with the prior art and/or embodiments not according to the invention. The following Examples are not meant to limit the scope and breadth of the present invention, as recited in the appended claims.

Comparison of PFSC with PDB

The proteins structures with PDB identifiers (PDB ID) 1ECA, 1AAJ, 2RN2 and 8DFR are randomly selected as examples from the structural classes of $\alpha$, $\beta$, $\alpha+\beta$ and $\alpha/\beta$ respectively. The comparison of structural assignments between PFSC and data in the PDB with these identifiers is displayed in Table II. Here the structural assignments in PDB by author, DSSP and STRIDE are listed with descriptions from PFSC. In order explicitly to describe the assignment for secondary structures, the protein folding shape code assignment for secondary structures (PFSCA) is a simple expression for the PFSC in Table II. The results show three features of the PFSC method. First, the secondary structural assignments from PFSC and PDB ("author", DSSP and STRIDE) have overall agreement. Second, the PFSC method is able to offer the complete description for folding shapes along a protein backbone, including regular fragments, irregular loops and coils. Third, the PFSC is able to discover details of the protein structural folding features with meaningful explanation.

TABLE II

The comparison of structural assignments between PFSC and PDB for proteins of
1ECA, 1AAJ, 2RN2 and 8DFR

```
                    1         10        20        30        40        50        60        70        80
          SEQ ID    |         |         |         |         |         |         |         |         |
          NO. 1:    LSADQISTVQASFDKVKGDPVGILYAVFKADPSIMAKFTQFAGKDLESIKGTAPFETHANRIVGFFSKIIGELPNIEADV
          Athr:     -aaaaaaaaaaaaaaaa-aaaaaaaaaaaaaaaaaaaa------aaaaaa--aaaaaaaaaaaaaaaaaaa---aaaaa
          DSSP:     --HHHHHHHHHHHHTTTT-HHHHHHHHHHH-HHHHTT-TTTTTT--HHHHTT-HHHHHHHHHHHHHHHHHHTTT--HHHH
          STRIDE    --HHHHHHHHHHHHTTTTHHHHHHHHHHHH-HHHHHHTTTTTTT-HHHHH--HHHHHHHHHHHHHHHHHHTTTHHHHH
1ECA      PFSC:        YAAAAAAAAAAAAAAAJVAAAAAAAAAAJVAAAAAJVAAAAHJVAAAAAHAAAAAAAAAAAAAAAAAAAJVAJHAAAA
 α        PFSCA:       Y**************<>***********<>*****<>*****<>******************************<>*<*****

81        90        100       110       120       130
          SEQ ID    |         |         |         |         |         |
          NO. 1:    NTFVASHKPRGVTHDQLNNFRAGFVSYMKAHTDFAGAEAAWGATLDTFFGMIFSKM
          Athr:     aaaaaaaaaaa-aaaaaaaaaaaaaaaaaaaa----aaaaaaaaaaaaaaaa---
          DSSP:     HHHHHHHHHHHT--HHHHHHHHHHHHHHHHHH---HHHHHHHHHHHHHHHHHHH-
          STRIDE:   HHHHHHHGGG---HHHHHHHHHHHHHHHHHH-TTTTHHHHHHHHHHHHHHHH--
          PFSC:     AAAAAAAAAABBBAAAAAAAAAAAAAAAAAAAJVAAAAAAAAAAAAAAAAAAAA
          PFSCA:    ********===********************<>*********************
```

TABLE II-continued

The comparison of structural assignments between PFSC and PDB for proteins of
1ECA, 1AAJ, 2RN2 and 8DFR

```
                  1         10        20        30        40        50        60        70        80
                  |          |         |         |         |         |         |         |         |
1AAJ    SEQ ID
β       NO. 2:    DKATIPSESPFAAAEVADGAIVVDIAKMKYETPELHVKVGDTVTWINREAMPHNVHFVAGVLGEAALKGPMMKKEQAYSL
        Athr:     -bbbbbbbbbbbb---ccccbbbbbbbccc---bbbbbcccbbbbbbbb----bbbbbcccc----bbbbbbbcbbbbbb
        DSSP:     --EE------EEHHH--TT-EEEEEETTEE--EEEE-TT-EEEEEE-----E--EE-TTT-----EE---E-TTEEEEE
        STRIDE:   --EETTTTTTEEGGG-TTTTEEEEEETTEETTTEEEETTTEEEEEEE-----B--EETTTTTTTTTEE---BTTTEEEEE
        PFSC:       JBBVJVAJWSVAJHHAJBBBBBBVQYHBVJVJBBBPYJBBBBBBBVAHHBBUIBBWYAAQCYAJBBWYJBWZJBBBBB
        PFSCA:    <==><*<>S>*<***<======>QY*=><><===PY<=======>***==><==>Y**QCY*<==>Y<=>Z<=====
                  81        90        100
                  |          |         |
        SEQ ID
        NO. 2:    TFTEAGTYDYHCTPHPFMRGKVVVE
        Athr:     bbb--bbbbbbccccccc-bbbbbb
        DSSP:     EE---EEEEEE----TT-EEEEEE-
        STRIDE:   EE---EEEEEEETTEEEEEEEEEE-
        PFSC:     BBVAHPSBBBVJVAJVAJBBBBB
        PFSCA:    ==>**PS===><>*<>*<=====

1         10        20        30        40        50        60        70        80
                  |          |         |         |         |         |         |         |         |
2RN2    SEQ ID
α+β     NO. 3:    MLKQVEIFTDGSCLGNPGPGGYGAILRYRGREKTFSAGYTRTTNNRMELMAAIVALEALKEHCEVILSTDSQYVRQGITQ
        Athr:     ----bbbbbbbbbb----bbbbbbbbbbcccbbbbbbbb---aaaaaaaaaaaaaaaaa---bbbbbbb-aaaaaaaaa-
        DSSP:     ----EEEEEEEEE--TTEEEEEEEEEEEETTEEEEEEEEEEEE-HHHHHHHHHHHHHHT-----EEEEEE--HHHHHHHHH
        STRIDE:   ----EEEEEEEEE-TTTEEEEEEEEEEETTEEEEEEEEEEEE-HHHHHHHHHHHHHH-----EEEEEEE--HHHHHHHH
        PFSC:     VABBBBBBBBBVPZAWSBBBBBBBBW$YJBBBBBBBBVAHHAAAAAAAAAAAAAAAJVPSBBBBBBBBVAAAAAADA
        PFSCA:    >*==========>PZ*>S=========>$Y<=======>**************<>PS=========>********
                  81        90        100       110       120       130       140       150
                  |          |         |         |         |         |         |         |
        SEQ ID
        NO. 3:    WIHNWKKRGWKTADKKPVKNVDLWQRLDAALGQHQIKWEWVKGHAGHPENERCDELARAAAMNPTLEDTGYQVEV
        Athr:     aaaaaaaaaa--cccc---cccaaaaaaaaaaaaabbbbbbbcccc-aaaaaaaaaaaaaaaaaa----cccc----
        DSSP:     THHHHHHTT-E-TT--E-TTHHHHHHHHHHT-EEEEEE--TT---HHHHHHHHHHHHHHT---E--TT-----
        STRIDE:   HHHHHHHHTBTTTT-BTTTHHHHHHHHHH-EEEEEEE-BTTBT-HHHHHHHHHHHHHHHH---B-TTTT----
        PFSC:     AAAAAAAAPSHHAAJWYPYJVAAAAAAAAAAAABBBBBBBHAAAHHAAAAAAAAAAAAAAAAAAJBVABBVABBV
        PFSCA:    ********PS****<>YPY<>*************======**************<=>*==>*==>

1         10        20        30        40        50        60        70        80
                  |          |         |         |         |         |         |         |         |
8DFR    SEQ ID
α/β     NO. 4:    VRSLNSIVAVCQNMGIGKDGNLPWPPLRNEYKYFQRMTSTSHVEGKQNAVIMGKKTWFSIPEKNRPLKDRINIVLSRELK
        Athr:     ---bbbbbbcccc---cccc-----aaaaaaaaaaaaaa--ccccbbbbbbaaaaaaa-cccc--cccc bbbbbb---
        DSSP:     --EEEEEEEE-TT-EEEETTE------HHHHHHHHHHHH----TT-EEEEEEHHHHHH--HHH---TTEEEEEE-----
        STRIDE:   ---EEEEEEETTTTEEEBTTB------HHHHHHHHHHHH---TTTTEEEEEE-HHHHHH--GGGTTTTTEEEEEETTTT-
        PFSC:     SBBBBBBBWZABBVJW$ZPSVAPSBVAAAAAAAAAAAJBVAAAJUIBBBVHAAAAAAHHAAJVAHAAHBBBBBBVAJV
        PFSCA:    S=======>Z*==><>$ZPS>*PS=>***********<=>***<><===>***********<>****======>*<>
                  81        90        100       110       120       130       140       150       160
                  |          |         |         |         |         |         |         |         |
        SEQ ID
        NO. 4:    EAPKGAHYLSKSLDDALALLDSPELKSKVDMVWIVGGTAVYKAAMEKPINHRLFVTRILHEFESDTFFPEIDYKDFKLLT
        Athr:     ---cccc-bbb-aaaaaaaaaaa-----bbbbbbbbbaaaaaaaaaaa--bbbbbbbbbb---------------bbb-
        DSSP:     ---TT--EEE--HHHHHHHHH-HHHHTTEEEEEE----HHHHHHHHH---EEEEEEEE-------EE-----TTT-EE--
        STRIDE:   --TTTT-EEE--HHHHHHHHH-HHHHH-EEEEEE---HHHHHHHHHTTT-EEEEEEEE-------EE----TTTTEEEET
        PFSC:     PYPZABVJBBVAAAAAAAAAAHAAAAAJVJBBBBBWZAAAAAAAAHHPSBBBBBBBBVAIVJBVJVHPSBBVAAJBBBV
        PFSCA:    PYPZ*=><==>**************<><=====>Z*********PS========>*<><=><>*PS==>**<===>
                  161       170       180
                  |          |         |
        SEQ ID
        NO. 4:    EYPGVPADIQEEDGIQYKFEVYQKSV
        Athr:     -cccc------cccbbbbbbbbbbb-
        DSSP:     -ETTE----EEETTEEEEEEEEEE--
        STRIDE:   TBTTB----EEETTEEEEEEEEEE
        PFSC:     JVAAHBVHJBBVQYBBBBBBBBBBB
        PFSCA:    <>***=>*<==>QY==========
```

1. The left column displays the $C_\alpha$ protein backbone structure, name and its classification.
2. SEQ ID NO. 1, SEQ ID NO, 2, SEQ ID NO. 3, SEQ ID NO. 4: Amino acid sequence.
3. Athr: Structural assignments in PDB by authors. "a" indicates α-helices, "b" β-strands, letter "c" turns and "-" for undefined loops.
4. DSSP: Structural assignments from DSSP in PDB. "H" is α-helix, "E" β-strand, "T" turn, "S" bend, "G" $3_{10}$ helix, "B" isolated β-bridge and "-" undefined loops.
5. STRIDE: Structural assignments from STRIDE in PDB. "H" is α-helix, "E" β-sheet, "T" turn, "C" coil, "G" $3_{10}$ helix, "I" π-helix, "B" isolated β-bridge and "-" undefined loops.
6. PFSC: Structural assignments from PFSC method. "A" indicating α-helix and "B" β-strand. All other letters are defined in FIG. 5 and FIG. 6.
7. PFSCA: Expression of secondary structural assignments from PFSC. "*" is α-helix, "=" β-strand, "<" and ">" analogue vectors at N- or C-terminus of secondary structures, and other letters represent irregular tertiary structures defined in FIG. 5 and FIG. 6.
8. The red color indicates the α-helix, the blue color the β-strands. The purple color represents the PFSC analogous vectors for secondary structure.

The Relationship Between Secondary Structures and PFSC Vectors

The PFSC vectors are mathematically derived to describe the protein folding shapes where 27 vectors represent 27 folding patterns in enclosed space. Most types of observed secondary structures can be related to specific PFSC vectors. FIG. 4 shows that the PFSC space is partitioned into nine space zones, which relate to three angular zones and three pitch distance zones. Various secondary structures (β-strands, α-helix, γ-helix, π-helix, δ-helix, $3_{10}$ helix and $2.2_7$ helix) are found in different PFSC space zones. The relation between secondary structure and PFSC vector are shown in FIG. 4, and the corresponding vector letters are represented in FIG. 5 and FIG. 6. For instance, α-helix is located at the zone with torsion angle range 0° to 130° and pitch distance range 5.5 Å to 14.0 Å representing by vector "A"; β-strand is located at the zone with torsion angle range 130° to 180° and −130° to −180° and pitch distance range 5.5 Å to 14.0 Å representing by vector "B"; δ-helix locates at the zone with torsion angle 0° to 130° and pitch distance <5.5 Å representing by vector "D"; $3_{10}$ helix and $2.2_7$ helix locate at the zone with torsion angle 0° to 130° and pitch distance >14.0 Å representing as vector "H"; γ-helix and π-helix locate at the zone with torsion angle 0° to −130° and pitch distance <5.5 Å representing as vector "$".

Boundaries of Secondary Structural Fragments

The PFSC results in Table II show how the termini of secondary structural fragments are connected or extended. The structural assignments are slight different when comparing "author", DSSP, STRIDE and PFSC. Those differences appear primarily with regard to length and relative location of secondary structures. However, with PFSC method, most of boundaries of secondary structures of α-helices and β-strands are capped by analogous vectors to express folding shape transition. For example, for protein 1ECA, the analogous vectors "V", "J", "Y" and "H" appear at the ends of the α-helices with residue numbers [3], [19-20], [31-32], [38], [45-46], [72] and [76]. For protein 1AAJ, the analogous vectors of "V", "J" and "S" appear at the ends of β-strands with residue numbers [3], [6-8], [12-13], [26], [33-34], [48], [66], [71], [75], [83], [97] and [91]. These analogous vectors indicate the smooth shape transition at the ends of α-helix and β-strand fragments. On other hand, if analogous vectors do not appear at the ends of a secondary structural fragment, it may indicate a sharp change at the boundaries. For example, for protein with PDB ID 2RN2, the sharp changes appear at residue numbers [28] and [114-115]; for protein with PDB ID 8DFR, the sharp changes appear at residue numbers [48] and [117-118].

Turns and Loops

The protein secondary structural fragments are connected by turns, coils or loops. The PFSC is able to describe the segment motifs between secondary structural fragments when they are not available in the PDB. For example, in Table II, the structural fragment with residue numbers [36-46] of PDB ID 1ECA is assigned by "author" as "aaa------aa"; by DSSP as "TT-TTTTTT--"; and by STRIDES as "HHTTTTTTT-H". However, it is assigned by PFSC as "AAJVAAAAHJV". The structural fragment of [47-60] of PDB ID 1AAJ is assigned by "author" as "bb----bbbbbccc"; by DSSP as "E-----E--EE-TT"; and by STRIDES as "E-----B--EETTT". By PFSC it is assigned as "BVAHHBBUIB-BWYA". The results in Table II show that all gaps between secondary structures for 1ECA, 1AAJ, 2RN2 and 8DFR in the PDB are filled by the PFSC vectors. The PFSC offers the seamless description of protein folding shapes from secondary to tertiary structures. This completeness in assignment should provide more accurate, descriptive and effective comparison and analysis for protein structures.

Distortion of Secondary Structural Fragments

The PFSC method is able to reveal the distortion inside regular secondary structure fragments. The distorted fragments of proteins with PDB ID 1EAC and 1AAJ are indicated by PFSC, and they are displayed in FIG. 7. For example, in protein structure 1EAC, the folding structure of sequence [19-38] is simply assigned by "author" in PDB as a typical α-helical fragment. However, the PFSC method assigns α-helical analogous vectors "JV" rather than "AA" at residues [31-32], which causes a disruption from typical α-helical shape. The same disruption at residue [31] is also indicated by structural assignments with DSSP and STRIDE. The disruption of α-helical fragment [19-38] is shown with its $C_\alpha$ atom backbone image in the upper left corner of FIG. 7 (A). Three typical α-helical fragments of 1ECA are shown in FIG. 7 (A) for comparison. Another example is shown for the distortion in the α-strand sequence [2-13] for protein structure 1AAJ. This is displayed in the upper left corner of FIG. 7 (B). Here piece of PFSC description "VJVAJWSV" indicates the disruptive section of sequence [6-13] for the β-strand fragment. The structural assignment by "author" in PDB is simply defined this segment as a β-strand, but PFSC indicates that this fragment is not a typical flat β-strand segment. The same disruption is indicated by structural assignments with DSSP and STRIDE at residue [2-13] of 1AAJ. The $C_\alpha$ atom backbone image of fragment [2-13] shows the disrupted section in the second half of the segment. Three typical β-strand fragments of protein 1AAJ are compared with this distorted segment in FIG. 7 (B). For structural description, the PFSC method shows vary similar sensitivity as the DSSP and STRIDE methods. The PFSC has the ability to thoroughly expose the disruption existing within protein secondary structure fragments.

Comparison of PSFC with Other Methods

Various approaches have been developed to assign the secondary and even tertiary structures with alphabetic letters for 3D protein folding structures. First, the method DSSP, STRIDE, DEFINE, PCURVE, PSEA and the assignment in PDB by "author" primarily provide the secondary structural description for proteins. With given knowledge of ideal secondary structures as criteria, most of these methods extract information from the 3D coordinate data to find out the hydrogen bonding patterns, torsion angles around $C_\alpha$ atoms or $C_\alpha$ atom distances and etc. For example, with hydrogen bonding patterns, the DSSP approach tries to recognize eight types of secondary structures, such as α-helix, $3_{10}$ helix, π-helix, β-sheet, β-bridge, random coil and so on. With different design, the PFSC method intends to have a seamless description and provides vector assignment for any possible folding shape in space. However, the PFSC vectors are still able to relate to various secondary structural categories. FIG. 4 shows how the various types of secondary structures relate to the PFSC space zones with specific angular and pitch distance. Especially, it is noted that the methods, which try to construct the hydrogen bonding patterns, require the hydrogen atom positions defined by high resolution structural measurement. However, the PFSC method only requires that the $C_\alpha$ atom be defined, so the protein structures with low resolution data can be described by the PFSC method.

Second, the method SBB and PB are able to assign the alphabetic letters to the protein secondary and tertiary structures. The SBB method defines six optimum structural building blocks as the folding patterns from 97 protein chains and 19,438 of seven-residue segments, and the PB method selects 16 protein blocks from 342 proteins and 86,628 of five-residue segments. The choice of folding patterns from SBB or PB methods is the result of statistic analysis. Also, all folding patterns are not necessary to be associated. However, the 27 PFSC folding patterns are naturally associated each other because each folding pattern clearly represents one region for an enclosed space. Therefore, the meaningful PFSC vectors are able to provide the seamless description of folding shapes along protein backbone.

The results of two proteins are available as samples for PFSC method to compare with various methods for structural assignments. The data of ribosomal protein S15 from *Bacillus Stearothermophilus* (PDB ID 1A32) has been published by PB study to compare with six different methods (40). The data of β-lactamase protein chain A from *Bacillus Licheniformis* (PDB ID 4BLM) has been published by SBB study to compare with DSSP results (36) Based on these given data of proteins 1A32 and 4BLM, the folding structural assignments by PFSC and various methods are listed in Table III and Table IV.

TABLE III

Structural assignments by PFSC and various methods for protein of Ribosomal
S15 from *Bacillus Stearothermophilus* (PDB ID 1A32)

```
1A32         1         10        20        30        40        50        60        70        80
SEQ ID       |         |         |         |         |         |         |         |         |
NO. 5        LTQERKREIIEQFKVHENDTGSPEVQIAILTEQINNLNEHLRVHKKDHHSRRGLLKMVGKRRRLLAYLRNKDVARYREIVEKLGL
PDB          ---aaaaaaaaaa----------aaaaaaaaaaaaaaaaaaaaaa-----aaaaaaaaaaaaaaaaaaaaaa-aaaaaaaaaaa-
DSSP         CCHHHHHHHHHHCCCCCCCCCCHHHHHHHHHHHHHHHHHHHHHCCCCHHHHHHHHHHHHHHHHHHHHHHCHHHHHHHHHHHCC
STRIDE       CCHHHHHHHHHHCCCCCCCCCCHHHHHHHHHHHHHHHHHHHHHCCCCHHHHHHHHHHHHHHHHHHHHHHCHHHHHHHHHHHCC
PESA         CCHHHHHHHHHHHEEEECCCCCHHHHHHHHHHHHHHHHHHHHHCCCCCHHHHHHHHHHHHHHHHHHHHHCHHHHHHHHHHHCC
DEFINE       CCCHHHHHHHHHHHEEECCCCHHHHHHHHHHHHHHHHHHHHHHEEEEHHHHHHHHHHHHHHHHHHHHHHHHHHHHHHHHHHH
PCURVE       CCHHHHHHHHHHCCCCCCCCCCHHHHHHHHHHHHHHHHHHHHHCCCHHHHHHHHHHHHHHHHHHHHHHHCHHHHHHHHHHHCC
PB           ZZklmmmmmmmmmgcehiopafklmmmmmmmmmmmmmmmmmmmmmmbmklmmmmmmmmmmmmmmmmmmmmmmlmmmmmmmnoZZ
PFSC         AAAAAAAAAAAJVPYHBBVJVAAAAAAAAAAAAAAAAAAAAJVABVAAAAAAAAAAAAAAAAAAAAAAQSVAAAAAAAAAA
```

1. 1A32: Protein Ribosomal S15 from *Bacillus Stearothermophilus*.
2. SEQ ID NO. 5: Amino acid sequence of protein structure with PDB ID 1A32.
3. PDB: The secondary structural assignment in PDB data by author, "a" is α-helix and "-" undefined loop.
4. DSSP, STRIDE, PSEA, DEFINE and PCURVE: The structural assignments by these methods respectively. The "H" is α-helix, "E" β-strand and "C" coils.
5. PB: The structural assignments by protein block method. The "m" is α-helix, "d" β-strand, "k", "l", "n", "o" and "p" for loops like α-helix, "a", "b", "c", "e" and "f" for loops like β-strand, "h", "I" and "j" for coil and ZZ for the extremities not assigned.
6. PSFC: The structural assignments by PFSC. The "A" is α-helix, "B" β-strand, and other vectors are defined in FIG. 5 and FIG. 6.
7. The red letter indicates the α-helix, blue letter the β-strand and purple letter the PFSC analogous vectors for secondary structure.

TABLE IV

Structural assignments by PFSC and various methods for protein of β-Lactamase
from *Bacillus Licheniformis* (PDB ID 4BLM, chain A)

```
             31        40        50        60        70        80        90        100       110
SEQ ID       |         |         |         |         |         |         |         |         |
NO. 6        DDFAKLEEQFDAKLGIFALDTGTNRTV  AYRPDERFAFASTIKALTVGVLLQQ  KSIEDLNQRITYTRDDLVNYNPITE
PDB          aaaaaaaaaaaa-bbbbbbbbb--bbbb bb--bbbb---aaaaaaaaaaaaaa  aaaaaaaa-------------aaaaa
DSSP         -HHHHHHHHHHTSEEEEEEEETTT--EE EESTT-EEE-GGGHHHHHHHHHHHH   S-TGGGG-EE---GGG--S--TTGG
STRIDE       HHHHHHHHHH-EEEEEEEETTT--EE   EETTTTEEE-GGGGGGGGHHHHHH--TTTTB---TTTGGG--TTTTTTTGG
SSB          ***aaaaaahtbbbbbbbbizzhtbbb  ibithttbbiizaaaaaaaaaaah   hizzaahtbbbbizzhtizhizzaa
PFSC         AAAAAAAJHHIBBBBBBBVDABBBB    BWSVAHBWSBWYAAAAAAAAAAAA   AHAAAAAHBBBBWYAAJWYJBVDAA 111       120       130       140       150       160       170       180       190
SEQ ID       |         |         |         |         |         |         |         |         |
NO. 6        KHVDTGMTLKELADASLRYSDNAAQNLILKQIGGPESLKKELRKIGDEVTNPERFEPELNEVNPGETQDTS TARALVTSL
PDB          aa-------aaaaaaaaaa-aaaaaaaaaaaa-aaaaaaaaaa-----bbbbb--aaaaaaa-----bbbbbbaaaaaaa
DSSP         G-TTT-EEHHHHHHHHHHHH--HHHHHHHHHTT-HHHHHHHHHHTT-SS-------TTGG---TT--TTEEEEHHHHHHH
STRIDE       GTTTTTTEEHHHHHHHHHHH--HHHHHHHHHH--HHHHHHHHHHHH-TTTTB---TTTGGG--TTTTTTTEEEEHHHHHHHH
SSB          aaahhtbizzaaaaaaaahhtizzaaaaaaaahhizzaaaaaaaaahhizhtbbbizzaahttizhtizhtbizzaaaaaaa
PFSC         AAAAJVHHAAAAAAAAADDABBVAAAAAAAAAADPCZAAAAAAAAADJBVAJBBVAPYAAAAJBWYABBAABUHAAAAAAAA 191       200       210       220       230       240       250       260       270
SEQ ID       |         |         |         |         |         |         |         |         |
NO. 6        RAFALEDKLPSEKRELLIDWMKRNTTGDALIRAGVPDGWEVADKTGAA SYGTRNDIAIIWP PKGDPVVLAVLSSRDKK
PDB          aaaaaa----aaaaaaaaaaaa-----aaaaaaaa---bbbbbbbbbb b-bbbbbbbbbbb ---bbbbbbbbbbb--
DSSP         HHHHHSSSS-HHHHHHHHHHHT-SS-TTTGGGGS-TT-EEEEEEEEE  TTTEEEEEEEEE- SSS--EEEEEEEE-SST
STRIDE       HHHHH-TTTTHHHHHHHHHHHHHTTTTTTTGGG--TTTTEEEEEEEEE TTTEEEEEEEEET TTT--EEEEEEEE--TT
SSB          aaaahhzhhizzaaaaaaaaahtzzaaaazaahtizhtbbbbbbbbi  zhhtbbbbbbbbi zhhbbbbbbbbbbibiz
PFSC         AADDAPYAAHAAAAAAAAAAAAJBVAAAAQZAAAHPYABBBBBBBBBW YQSBBBBBBBBV  APYAJBBBBBBBBBHJV 271       280       290
SEQ ID       |         |         |
NO. 6        DAKYDDKLIAEATKVVMKALN
PDB          -----aaaaaaaaaaaaaaa
DSSP         T----THHHHHHHHHHHHH-
STRIDE       TT---HHHHHHHHHHHHHH-
SSB          htbbizzaaaaaaaaaaa***
PFSC         JBBBBVAAAAAAAAAAAAD
```

1. SEQ ID NO. 6: Amino acid sequence of protein of β-lactamase of *Bacillus Licheniformis* (PDB ID 4BLM, chain A).
2. PDB: The secondary structural assignment by authors in PDB in PDB data, "a" is α-helix, "b" β-strand and "-" undefined loop.
3. DSSP: The structural assignments from Database of Secondary Structure of Proteins method. The "H" is α-helix, "E" β-strand, "T" turn, "S" bend, "G" $3_{10}$ helix, "B" isolated β-bridge and "-" undefined loop.
4. STRIDE: The Structural assignments from STRIDE in PDB. "H" is α-helix, "E" β-sheet, "T" turn, "C" coil, "G" $3_{10}$ helix, "I" π-helix, "B" isolated β-bridge and "-" undefined loop.
5. SBB: The structural assignments by Structural Building Blocks method. The "a" is α-helix, "b" β-strand, "z" and "h" for N- and C-termini of α-helices and "t" and "i" for N- and C-termini of β-strands.
6. PSFC: The structural assignments from PFSC. The "A" is α-helix, "B" β-strand, and other vectors are defined in FIG. 5 and FIG. 6.
7. The red color indicates the α-helix, the blue color the β-strands. The purple color represents the PFSC analogous vectors for secondary structure.

In order easily to compare the structural assignment by various method in Table III and Table IV, the letters with red color represent the α-helices, blue color the β-strands and purple color the PFSC analogous vectors for α-helix or β-strand. The results from these two tables show that the assignments for secondary structures have overall agreement between the PFSC method and other methods. Also it is obvious that different methods do not assign the same exact lengths and boundaries for secondary structure fragments. In fact, the ending shapes of secondary structure fragments are not abruptly terminated in most cases. The ends of secondary structural fragments may be somehow distorted or extended to prepare the shape transition for neighboring motifs. Various methods adopt different algorithms, parameters and tolerance as criteria, which cause the ambiguity of assignments of relative lengths and positions for secondary structure fragments. The 27 PFSC vectors cover an enclosed space with folding patterns, and various folding shapes and shape changes are able to be described. The advantages of the PFSC description for structural assignments are shown by three aspects.

(1) Analogous Vectors for Smooth Transition of Folding Change

Each PFSC vector has a set of analogous vectors surrounding it. For instance, vector "A" has six analogous vectors, "V", "J", "Y", "P", "H" and "D"; vector "B" has six analogous vectors, "V", "J", "S", "M", "E" and "G" in FIG. 6. The analogous vectors may be assigned to the shape transition for structural assignment. The PFSC structural description is obtained by concatenation of local structural assignments, In other words the PFSC description is generated by moving the vector along the protein backbone one $C_\alpha$ atom by one $C_\alpha$ atom. When the end of secondary fragment starts twisting, the transition folding shape may be expressed by the PFSC analogous vectors for α-helix or β-strand.

With benefit from analogous vector, the PFSC has capability to reflect the gradual change at the end of secondary structure fragment. In Table III, the analogous vectors appear on the most of ends of α-helical fragments in protein structure 1A32A, such as "JVPYH" at the C-terminus of α-helix [3-13]; "VJV" at the N-terminus and "JV" at the C-terminus of α-helix [23-43]; "V" at the N-terminus for α-helix [48-70] and α-helix [74-83]. The similar observations are found out in Table IV. The analogous vectors appear on the ends of α-helices and β-strands of protein 4BML, such as "JHH" at the C-terminus of α-helix [33-39]; "Y" at the N-terminus of α-helix [71-86], "JVHH" at the N-terminus and "DD" at the C-terminus of α-helix [119-126], "S" at the N-terminus and "V" at the C-terminus of β-strand [243-251] and "J" at the N-terminus of β-strand [259-267]. With PFSC, it is not necessary to define obvious length and boundary because of the gradual transition can be described at the ends of secondary structural fragments. It is more important to make the structural description with better assignment to reflect the nature of secondary structures. The concept of PFSC analogous vector provides the flexibility to describe the boundaries of secondary structures.

(2) Tendency of Capping Secondary Structures

The tendency of capping secondary structures is also shown by PFSC results. With analogous vectors, the capping secondary structural fragment demonstrates the features of structural assignments by PFSC method, which is shown in Table III and Table IV as well Table II. Here the capping means one extra PFSC vector at N- and C-termini of secondary structural fragment. In order to exhibit how the PFSC vectors are assigned to the N- and C-termini of α-helices and β-strands, all of secondary structural fragments of proteins 1A32 and 4BLM are listed in Table V. The results in Table V show the tendency of assignment for capping secondary structural fragments. The tendency is well associated with the diagram orientation of the 27 vectors in space in FIG. 6. The N-termini of α-helices are capped by vectors ("V", "Y" or "Z") with torsion angle at $a_1$ in zone 1, the C-termini of α-helices by vectors ("J", "P", "D" or "Q") with torsion angle $b_1$ in zone 1. The N-termini of β-strands are capped by vectors ("J", "S" or "I") with torsion angle $a_1$ in zone 2, and the C-termini of β-strands by vectors ("V", "W" or "U") with torsion angle $b_1$ in zone 2. Also, the "H" vector may appear at both N- and C-termini of α-helices and β-strands. The "B" vector may directly connect with the N- and C-termini of α-helices; reversely the "A" vector may directly connect with the N- and C-termini of β-strands. The results evidently illustrate that explicit features exist for capping N- and C-termini for α-helices and β-strands respectively. In other words, the tendency of structural assignments is well shown by capping secondary structure fragments.

The inclination is able to be explained by characteristics of vectors in FIG. 5. The folding shape arrows have angular folding characters attached at the N- and C-terminus of each vector. If two vectors are connected, the C-terminus of one vector must be coupled with the N-terminus of next vector. For smooth folding transition, the folding characters from the N-terminus and the C-terminus should be matched, i.e. "α" connect to "α", "β" to "β" and "*" to "*". Therefore, the vectors ("V", "Y" or "Z") like to use their α-helical C-terminus to couple with the N-terminus of α-helices; the vectors ("J", "P", "D" or "Q") like to use their α-helical N-terminus to couple with the C-terminus of α-helices; the vectors ("J", "S" or "I") like to use β-strand character at C-terminus to couple with the N-terminus of β-strand; the vectors ("V", "W" or "U") like to use β-strand character at N-terminus to couple with the C-terminus of β-strand. These results show the selectivity in making vector coupling, which determines the tendency of capping secondary structures by PFSC method.

The similar tendency of capping secondary structure is also shown by the results of SSB and BP methods. The PFSC method is well compared with SSB and BP methods in capping assignment of secondary structure, which is displayed in Table VI. However, the PFSC has capability to explain the structural capping assignments by vector characteristics.

TABLE V

Capping secondary structure fragments by PFSC for proteins with PDB ID 1A32 and chain A of 4BLM

| | Protein | Residue | Sequence | PFSC |
|---|---|---|---|---|
| α-Helix | 1A32 | 1-16 (SEQ ID NO. 7) | LTQERKREIIEQFKVH | AAAAAAAAAAAJ |
| | 1A32 | 19-46 (SEQ ID NO. 8) | GSPEVQIAILTEQINNLNEHLRVHKK | VAAAAAAAAAAAAAAAAAAAAJ |

TABLE V-continued

Capping secondary structure fragments by PFSC for proteins with PDB ID 1A32 and chain A of 4BLM

| Protein | Residue | Sequence | PFSC |
|---|---|---|---|
| 1A32 | 46-69 (SEQ ID NO. 9) | KDHHSRRGLLKMVGKRRRLLAYLRNKDV | VAAAAAAAAAAAAAAAAAAAAAAAQ |
| 1A32 | 71-85 (SEQ ID NO. 10) | KDVARYREIVEKLGL | VAAAAAAAAA |
| 4BLM | 31-42 (SEQ ID NO. 11) | DDFAKLEEQFDA | AAAAAAAJ |
| 4BLM | 49-56 (SEQ ID NO. 12) | LDTGTNRT | VAAB |
| 4BLM | 60-66 (SEQ ID NO. 13) | YRPDERF | VAH |
| 4BLM | 68-89 (SEQ ID NO. 14) | FASTIKALTVGVLLQQKSIE | YAAAAAAAAAAAAAH |
| 4BLM | 87-95 (SEQ ID NO. 15) | SIEDLNQRI | HAAAAAH |
| 4BLM | 99-102 (SEQ ID NO. 16) | YTRDDLVN | YAAJ |
| 4BLM | 107-114 (SEQ ID NO. 17) | YNPITEKHVDTGM | VAAAAAAAJ |
| 4BLM | 115-130 (SEQ ID NO. 18) | GMTLKELADASLRYS | HAAAAAAAAD |
| 4BLM | 130-144 (SEQ ID NO. 19) | SDNAAQNLILKQIGG | VAAAAAAAAD |
| 4BLM | 143-157 (SEQ ID NO. 20) | GGPESLKKELRKIGD | ZAAAAAAAAD |
| 4BLM | 156-162 (SEQ ID NO. 21) | GDEVTNP | VAJ |
| 4BLM | 161-167 (SEQ ID NO. 22) | NPERFEP | VAP |
| 4BLM | 164-173 (SEQ ID NO. 23) | RFEPELNEVN | YAAAAJ |
| 4BLM | 172-178 (SEQ ID NO. 24) | VNPGETQ | YAB |
| 4BLM | 175-182 (SEQ ID NO. 25) | GETQDTST | BAAB |
| 4BLM | 180-195 (SEQ ID NO. 26) | TSTARALVTSLRAFALE | HAAAAAAAAAD |
| 4BLM | 198-215 (SEQ ID NO. 27) | KLPSEKRELLIDWMKRNT | HAAAAAAAAAAAJ |
| 4BLM | 213-222 (SEQ ID NO. 28) | RNTTGDALIR | VAAAAQ |
| 4BLM | 219-228 (SEQ ID NO. 29) | ALIRAGVPD | ZAAAH |
| 4BLM | 50-257 (SEQ ID NO. 30) | IWPIWP | VAP |
| 4BLM | 254-260 (SEQ ID NO. 31) | PKGDPVV | YAJ |
| 4BLM | 273-291 (SEQ ID NO. 32) | YDDKLIAEATKVVMKALN | VAAAAAAAAAAAA |
| β-Strand 1A32 | 16-23 (SEQ ID NO. 33) | HENDTGSP | HBBV |
| 1A32 | 44-50 (SEQ ID NO. 34) | HKKDHHS | ABV |
| 4BLM | 41-53 (SEQ ID NO. 35) | DAKLGIFALDTGT | IBBBBBBBV |
| 4BLM | 51-62 (SEQ ID NO. 36) | TGTNRTVAYRP | ABBBBBBW |
| 4BLM | 62-68 (SEQ ID NO. 37) | PDERFAF | HBW |
| 4BLM | 75-71 (SEQ ID NO. 38) | RFAFAST | SBW |
| 4BLM | 91-100 (SEQ ID NO. 39) | LNQRITYTRD | HBBBBW |
| 4BLM | 103-109 (SEQ ID NO. 40) | VNYNPIT | JBV |
| 4BLM | 127-134 (SEQ ID NO. 41) | LRYSDNAA | JBBV |
| 4BLM | 154-160 (SEQ ID NO. 42) | KIGDEVT | JBV |
| 4BLM | 158-160 (SEQ ID NO. 43) | EVTNPERF | JBBV |
| 4BLM | 169-175 (SEQ ID NO. 44) | LNEVNPG | JBW |
| 4BLM | 173-180 (SEQ ID NO. 45) | NPGETQDT | ABBA |

TABLE V-continued

Capping secondary structure fragments by PFSC for proteins with PDB ID 1A32 and chain A of 4BLM

| Protein | Residue | Sequence | PFSC |
|---------|---------|----------|------|
| 4BLM | 177-183 (SEQ ID NO. 46) | TQDTSTA | ABU |
| 4BLM | 211-217 (SEQ ID NO. 47) | MKRNTTG | JBV |
| 4BLM | 226-241 (SEQ ID NO. 48) | PDGWEVADKTGAASY | ABBBBBBBBBW |
| 4BLM | 240-255 (SEQ ID NO. 49) | SYGTRNDIAIIWPPK | SBBBBBBBBBV |
| 4BLM | 256-270 (SEQ ID NO. 50) | GDPVVLAVLSSRDKK | JBBBBBBBBBH |
| 4BLM | 269-277 (SEQ ID NO. 51) | KKDAKYDDKL | JBBBBV |

1. The first column is types of secondary structures.
2. The second column is the protein ID code: 1A32 and chain A of 4BLM.
3. The third column is the residue numbers for fragments.
4. The fourth column is amino acid sequences for secondary structure fragments.
5. The fifth column is the secondary structure assignments by the PFSC with one capping vector at the N- and C-termini.
6. The red letter indicates the helix, blue letter the β-strand and purple letter the PFSC analogous vectors for secondary structure.

TABLE VI

Comparison of PFSC, SBB and PB methods for secondary structure capping

| | SBB | PB | PFSC | | SBB | PB | PFSC |
|---|---|---|---|---|---|---|---|
| α-helix | a | m | A | N-Cap | z (ζ) | k, l | V, Y, Z, H |
| | | | | C-Cap | h (η) | n, o, p | J, P, D, Q, H |
| β-strand | b | d | B | N-Cap | t (τ) | a, b, c | J, S, I, H |
| | | | | C-Cap | i (ι) | e, f | V, W, U, H |

1. N-Cap is the capping at N-terminus for α-helix or β-strand fragment.
2. C-Cap is the capping at C-terminus for α-helix or β-strand fragment.
3. The columns of 2, 3 and 4 are the letters for secondary structure assignment, and the columns of 6, 7 and 8 are the letters for capping assignment from method SBB, PB and PFSC respectively.

(3) Structural Assignment for Turns and Loops:

With 27 vectors, the PFSC method is able to offer detail description for turns or loops between regular secondary structures. This capability brings certain advantage to compare with other methods. Most of methods, such as the deposited data in PDB by "author", DSSP, STRIDE, PESA, DEFINE, PCURVE and KAKSI, primarily focus on the assignment of secondary structures. The methods of PB and SBB are able to assign secondary and tertiary for proteins. However, the 27 PFSC vectors of PFSC offer the seamless structural description for protein $C_\alpha$ backbone while they provide the meaningful illustration for structural assignment.

The comparison between PFSC method and "authors", DSSP, STRIDE, DB, SSB methods for the structural assignments for turns or loops is listed in Table VII. The results show that, with the exception of gaps, some degree of agreements exists between various methods while the differences are observed. First, the data in PDB by "authors", and the DSSP, STRIDE and PFSC methods provide the different express to cover the irregular fragments of loops. For turns and loops between secondary structures, the results from data by "authors" are almost without structural assignments. The results from DSSP and STRIDE provide more motifs, but left the undetermined gasps. Also, both methods make the different descriptions for the same residue. For example, each residues of 4BLM [91-110], [153-169], [169-181], [193-203], [212-222] and [266-278] shows the different assignments by the DSSP and STRIDE methods. The PFSC method, however, does not only supply the complete structural assignment, but also has capability to provide the detail folding structural information for turns and loops.

Second, the PFSC method, same as the PB and SSB methods, provides the complete structural descriptions for the turns and loops. Overall, the results show that the assignment from PFSC has better agreement with the result from SSB according the alignment of structural character. For example, β-strand character of 4BLM residues [49-57], [91-110], [153-169], [212-222] and [266-278] show the alignment between PFSC and SSB results. The PB and PFSC methods show the structural character alike, such as 1A32 residues [12-24] and [43-51], but the relative positions for structural character are shifted somehow.

Third, the PFSC method is able to provide a vector description as additional express for protein folding structure. The PFSC with vector assignment (PFSCV) is talented to exhibit the folding shape features and changes. The PFSCV is a supplement for the PFSC letter description, which display the detail structural assignment. For instance, for the fragment of residue [12-24] of protein with PDB ID 1A32 in Table VII, the data in PDB by "author", and the DSSP and STRIDE results do not give detail description; the PB result gives a detail description as "mmgcehiopafkl". However, the PFSC method does not only give this fragment the PFSC letter description "AJVPYHBBVJVA", but also provide the PFSCV as a vector description "α-αα-αα-ββ-αα-**-αα-αβ-ββ-ββ-αα-ββ-αα-α". Here the PFSC results indicate that short and non typical β-strands exist inside the fragment with concurrence to the PSEA, DEFINE and PB methods in Table III. For fragment of residue [91-110] of protein chain A with PDB ID 4BLM in Table IV, the PFSC result not only fills all gaps, but also it gives the letter description "AAHBBBBWYAAJW-YJBVDAA" and the vector description "α-αα-αα-αβ-ββ-ββ-ββ-α*-αα-α-αα-ββ-α*-αα-ββ-ββ-αα-αα-αα-α". The PFSC result, same as the DSSP, STRIDE and SSB, indicates that this fragment contains a short β-strand and a short α-helix. However, the PFSCV result also provides the detail structural information how the short β-strands, α-helices and loops are connected inside this irregular fragment. These samples show that the PFSC method has ability to describe a complicated protein fragment, and to reveal the structure feature for the turn or loop.

TABLE VII

The comparison of structural assignments for turns and loops between PFSC and various methods

| Protein | Residues | Methods | Structural Assignment |
|---|---|---|---|
| 1A32 | 12-24 | SEQ ID NO. 52 | Q F K V H E N D T G S P E |
|  |  | PDB | a a - - - - - - - - - - a |
|  |  | DSSP | H C C C C C C C C C C H H |
|  |  | STRIDE | H H C C C C C C C C C H H |
|  |  | PB | m m g c e h i o p a f k l |
|  |  | PFSC | A A J V P Y H B B V J V A |
|  |  | PFSCV | α-αα-αα-ββ-αα-**-αα-αβ-ββ-ββ-αα-ββ-αα-α |
| 1A32 | 43-51 | SEQ ID NO. 53 | V H K K D H H S R |
|  |  | PDB | a a - - - - - a a |
|  |  | DSSP | H C C C C C H H H |
|  |  | STRIDE | H C C C C C H H H |
|  |  | PB | m m m b m k l m m |
|  |  | PFSC | A J V A B V A A A |
|  |  | PFSCV | α-αα-ββ-αα-αβ-ββ-αα-αα-αα-α |
| 4BLM | 49-57 | SEQ ID NO. 54 | L D T G T N R T V |
|  |  | PDB | b b b - - b b b b |
|  |  | DSSP | E E T T T - - E E |
|  |  | STRIDE | E T T T T - - E E |
|  |  | SSB | b i z z h t b b b |
|  |  | PFSC | B B V A A B B B B |
|  |  | PFSCV | β-ββ-ββ-αα-αα-αβ-ββ-ββ-ββ-β |
| 4BLM | 91-110 | SEQ ID NO. 55 | L N Q R I T Y T R D D L V N Y N P I T E |
|  |  | PDB | a a - - - - - - - - - - - - - - a a a a a |
|  |  | DSSP | G G - E E - - - G G G - - S - - T T G G |
|  |  | STRIDE | G G - E E - - - G G G - T T T T T T G G |
|  |  | SSB | a h t b b b b i z z h t i z h i z z a a |
|  |  | PFSC | A A H B B B B W Y A A J W Y J B V D A A |
|  |  | PFSCV | α-αα-αα-αβ-ββ-ββ-ββ-ββ-α*-αα-αα-αα-ββ-α*-αα-ββ-ββ-αα-αα-αα-α |
| 4BLM | 153-169 | SEQ ID NO. 56 | R K I G D E V T N P E R F E P E L |
|  |  | PDB | a - - - - - b b b b - a a a a a |
|  |  | DSSP | H H T T - S S - - - - - - - T T G |
|  |  | STRIDE | H H H - T T T T B - - - T T T G G |
|  |  | SSB | a a h h i z h t b b b i z z a a |
|  |  | PFSC | A A D J B V A J B B V A P Y A A A |
|  |  | PFSCV | α-αα-αα-αα-ββ-ββ-αα-αα-ββ-ββ-ββ-αα-αα-**-αα-αα-αα-α |
| 4BLM | 169-181 | SEQ ID NO. 57 | L N E V N P G E T Q D T S |
|  |  | PDB | a a a a - - - - b b b b |
|  |  | DSSP | G G - - - T T - - T T E E |
|  |  | STRIDE | G G - - T T T T T T T E E |
|  |  | SSB | a h t t i z h t i z h t b |
|  |  | PFSC | A A J B W Y A B B A A B U |
|  |  | PFSCV | α-αα-αα-ββ-ββ-α*-αα-αβ-ββ-βα-αα-αβ-ββ-α |
| 4BLM | 193-203 | SEQ ID NO. 58 | F A L E D K L P S E K |
|  |  | PDB | a a a a - - - a a a |
|  |  | DSSP | H H H S S S - H H H |
|  |  | STRIDE | H H H - T T T T H H H |
|  |  | SSB | a a h h z h h i z z a |
|  |  | PFSC | D D A P Y A A H A A A |
|  |  | PFSCV | α-αα-αα-αα-**-αα-αα-αα-αα-αα-αα-α |
| 4BLM | 212-222 | SEQ ID NO. 59 | K R N T T G D A L I R |
|  |  | PDB | a - - - - - a a a a a |
|  |  | DSSP | H T - S S - T T T G G |
|  |  | STRIDE | H H T T T T T T T G G |
|  |  | SSB | a h t z z a a a a z a |
|  |  | PFSC | A J B V A A A A Q Z A |
|  |  | PFSCV | α-αα-ββ-ββ-αα-αα-αα-αα-αα-**-αα-α |
| 4BLM | 266-278 | SEQ ID NO. 60 | S R D K K D A K Y D D K L |
|  |  | PDB | b b b - - - - - - - a a a |
|  |  | DSSP | E - S S T T - - - - T H H |
|  |  | STRIDE | E - - T T T T - - - H H H |

TABLE VII-continued

The comparison of structural assignments for turns and loops between PFSC and various methods

| Protein | Residues | Methods | Structural Assignment |
|---------|----------|---------|----------------------|
|         |          | SSB     | b i b i z h t b b i z z a |
|         |          | PFSC    | B B H J V J B B B B V A A |
|         |          | PFSCV   | β-ββ-βα-αα-ββ-αα-ββ-ββ-ββ-ββ-ββ-αα-αα-α |

1. Sequence: Amino acid sequences of protein 1A32 and chain A of protein 4BLM.
2. PDB: The secondary structural assignment in PDB by "authors", "a" is α-helix, "b" β-strand and "-" undefined loop.
3. DSSP: Database of Secondary Structure of Proteins method. The "H" is α-helix, "E" β-strand, "T" turn, "S" bend, "G" $3_{10}$ helix, "B" isolated β-bridge, and "-" undefined loop.
4. STRIDE: Structural assignments from STRIDE in PDB. "H" is α-helix, "E" β-sheet, "T" turn, "C" coil, "G" $3_{10}$ helix, "I" π-helix, "B" isolated β-bridge and "-" undefined loop.
5. PB: The structural assignments from Protein Block method. The "m" is α-helix, "d" β-strand, "k", "l", "n", "o" and "p" for loops like α-helix, "a", "b", "c", "e" and "f" for loops like β-strand, "h", "I" and "j" for coil and ZZ for the extremities not assigned.
6. SBB: The structural assignments from Structural Building Blocks method. The "a" is α-helix, "b" β-strand, "z" and "h" for N- and C-termini of α-helices and "t" and "i" for N- and C-termini of β-strands.
7. PSFC: The structural assignments from PFSC. The "A" is α-helix, "B" β-strand, and other vectors are defined in FIG. 5 and FIG. 6.
8. PFSCV: The PFSC with vector assignments. The 27 vector description is the arrow line defined in FIG. 5.
9. The red letter indicates the helix, blue letter the β-strand and purple letter the PFSC analogous vectors for secondary structure.

Protein Confirmation Analysis with PFSC

Protein conformers are the results of protein folding and folding changes. The protein conformation analysis is important because it studies possible protein folding structures under various conditions, and identifies protein misfolding which may relate to diseases treatment and prevention. The PFSC approach is a powerful tool to analyze protein confirmation since it is able to exhibit the local structural folding features in details. Traditionally, the comparison of protein conformers is to superimpose all of 3D structures, and then to provide the root-mean-square deviation (rmsd) as a numerical measurement. The PFSC method, however, assigns the vectors to folding shapes along the protein backbone, and then the protein folding shape code is able to be aligned for conformation analysis.

A set of 20 conformers of *Escherichia coli* glutaredoxin protein (PDB ID 1EGO) (Xia T H, Bushweller J H, Sodano P, Billeter M, Bjornbger O, Holmgren A, Wuthrich K. NMR structure of oxidized *Escherichia coli* glutaredoxin: Comparison with reduced *E. coli* glutaredoxin and functionally related proteins. Prot. Sci. 1992; 1:310-321) is analyzed by using PFSC approach. The 20 conformers of structures of 1EGO in aqueous solution with NMR measurement are given in PDB. The protein structure 1EGO consists of a four stranded β-sheets and three α-helices. The root-mean-square deviation (rmsd) values from the 20 individual conformers to their averaged coordinates for various selections of heavy atoms are about 1.1 Å for N, $C_\square$ and C' atoms on polypeptide backbone. The superimposed view of $C_\square$ atom backbone of the 20 conformers of 1EGO is displayed in FIG. 8.

The 20 conformers of 1LEGO are similar, and the distinguishing each other is only with slight difference of local folding shapes. To compare the protein conformers successfully, the structural assignments must be accurately to express the local structural fragment, and meanwhile must be sensitively to distinguish minor difference. The folding structural alignment of 20 conformers of 1EGO is listed in Table VIII. With the PFSC, the alignment of protein folding shape description is able to display similarity as well as dissimilarity. In order to have a straightforward analysis, the aligned structural segments are dyed with the same color.

Conformation Similarity

In Table VIII, the results show that eight pieces of structural motifs have exact same PFSC vector code assignments for all of 20 conformers of 1EGO. These eight pieces of similar structural folding segments at sequences [3-5], [13-25], [32-40], [43], [46-50], [61-64, [73-79] and [81] are marked with red color. While these eight segments have similar folding structures, the remainder of segments does not have the same PFSC vector code assignments for all of 20 conformers. Certain similarities, however, still exist within remained segments for some conformers. The further details are able to be exposed by analysis of the PFSC descriptions.

Conformation Dissimilarities:

The segments, which do not have the same assignments for all of 20 conformers, contain the information about dissimilarities of 20 conformers of 1EGO. First, some of dissimilarities may be analyzed by dividing the 20 conformers into different groups. For example, the segment at residue [26-31] does not have same PFSC vector assignments for all 20 of conformers, but the same structural assignments exist among some conformers. Five groups are found for segment at residue [26-31]. The group of conformers 1, 2, 8, 14, 18 and 20 has a set of PFSC vectors as "AAJVAJ". Similarly, the group of conformers 3 and 6 has the "ADJVHJ"; the group of conformers 4, 7 and 9 has the "AAAAB"; the group of conformers 10 and 15 has the "AAJVAB" and the group of conformers 11 and 17 has the "AAAAJB". Also, we note that the conformers 5, 12, 13, 16 and 19 do not belong to any group, so their folding shapes are different from other conformers in this segment. For the segment of residue [26-31], the conformers in same group keep the similarity, but the dissimilarities are distinguished by the groups. The conformers in same group are marked by the same colors in Table VIII.

Second, some of dissimilarities may be further analyzed by partitioning a segment into shorter pieces. For example, the segments of residue [6-12] are more diversionary because no group can be directly formed from 20 of conformers. With partition, some short pieces are found the similar for certain conformers and they are marked by the same colors in Table VIII. For short pieces at residues [6-8], the conformers 2 and 5 have the same set of short piece of "BBW"; the conformers 10 and 16 have the "BHH"; the conformers 11, 13, 17 and 17 have the "BBH". For short piece at residues [9-12], the conformers 2 and 7 have the same set of short piece of "CSBV". For short pieces at residue [10-12], the conformers 10 and 20 have the "SBA"; the conformers 5, 12, 13, 17, and 18 have the "AJV". Although, there is not identical pair among 20 conformers at the segments of residue [6-12], the PFSC still can reveal the similarity as well as dissimilarity within segments in details. These results show that the PFSC is able to align the protein folding structural assignment and compare protein conformation in detail.

A Tool for Conformation Analysis:

With the superimposition approach, the superimposed 3D structures of 20 conformers of 1EGO offer visualization for comparison, and the root-mean-square deviation (rmsd) provides the overall measurement. The PFSC is able to provide a supplement tool to analyze the protein conformations. With the PFSC description, all conformers are able to be simple aligned as one-dimension strings to compare each other. So, the difference of local folding structures of a protein is able to be discovered. The PFSC has the capability to play a significant role to facilitate the protein conformation analysis for either experimental data or result of computational dynamic simulation.

methods. Second, for given 3D coordinates of proteins, the 27 PFSC vectors are able to offer a complete description covering folding shapes and folding changes along the protein backbone. With this features, the 27 PFSC letters provide a useful digital description, which will promote the protein structural comparison. Third, with vector characteristics, the association of the 27 PFSC vectors in space shows the advantage for protein folding shape descriptions, which provides the meaningful structural assignment for protein structure.

Characteristics of PFSC Vector

Association Diagram of PFSC Vectors: The set of 27 PFSC vectors is not a group of protein folding patterns with random order. The 27 PFSC vectors are systemically ranked by distribution of three components, two torsion angles and a pitch distance. The arrangement of PFSC 27 vectors in FIG. 6 actually is an association diagram. The relationship can be

TABLE VIII

Conformation analysis with the PFSC for 20 conformers of the oxidized form of
E. coli glutaredoxin (PDB ID 1EGO)

| SEQ ID NO. | 61 MQTVIFGRSGCPYCVRAKDLAEKLSNER-DDFQYQYVDIRAEGITKEDLQQKAGKPVETVPQIFVDQQHIGGYTDFAAWVKENLDA |
|---|---|
| 1EGO-1 | BBBVHHAAHVAAAAAAAAAAAAAAAJVAJBBBBBBVAAAJBWZAAAAADJBBWSBVAJBBBW$YHJBPCZAAAAAAAAADD |
| 1EGO-2 | BBBBBWCSBVAAAAAAAAAAAAAAAJVAJBBBBBBVAAAJBVAAAAAAAJVBVAJVAJBBBW$YAJWCCZAAAAAAAAAA |
| 1EGO-3 | BBBBVPCSWYAAAAAAAAAAAAAADJVHJBBBBBBVAAABBBAAAAAAAJBBVABWYJBBBW$YHBVPCZAAAAAAAAAA |
| 1EGO-4 | BBBBVHAABVAAAAAAAAAAAAAAAABBBBBBBVAAAJBVAAAAAAAJVPSVAJVJBBBW$YAJVPCZAAAAAAAAAA |
| 1EGO-5 | BBBBBWYAJVAAAAAAAAAAAAAAJVJBBBBBBVAAABBVAAAAAAAJVPSBVJVJBBBW$YHBBPCZAAAAAAAAAD |
| 1EGO-6 | BBBBHBVAHAAAAAAAAAAAAAAADJVHJBBBBBBVAAABBWYAAAAAAJVJVAJWYJBBBWGYHJVPCZAAAAAAAAAD |
| 1EGO-7 | BBBBPCCSBVAAAAAAAAAAAAAAAABBBBBBVAAABBWYAAAAAAJBBVJBWYJBBBWZPCSVPCZAAAAAAAAAA |
| 1EGO-8 | BBBBVHAJBVAAAAAAAAAAAAAAJVAJBBBBBBVAAJBBVAAAAAAAJVJVABVAJBBBW$YHBBVAAAAAAAAAAAA |
| 1EGO-9 | BBBVJBHHHVAAAAAAAAAAAAAAABBBBBBBVAAABBWYAAAAAAJBHHBVPYJBBBW$YAJBPCZAAAAAAAADD |
| 1EGO-10 | BBBBHHPSBAAAAAAAAAAAAAAAJVABBBBBBVAAABBBAAAAAADJVABVPYAJBBBW$YAJBWCZAAAAAAAAAD |
| 1EGO-11 | BBBBBHAABVAAAAAAAAAAAAAAAJBBBBBBBVAAABBWYAAAAAAJBHPYJVAJBBBWZAPSVPCZAAAAAAAAAA |
| 1EGO-12 | BBBVPYAAJVAAAAAAAAAAAAAAJBBBBBBBVAAABBWYAAAAADJBBVAJBAJBBBW$YHBBWCYAAAAAAAAAD |
| 1EGO-13 | BBBBBHAAJVAAAAAAAAAAAAADAJVAJBBBBBBVAAAJBWZAAAAAAAWSBVJVAJBBBW$YHBBWCZAAAAAAAAAA |
| 1EGO-14 | BBBVHBVAHAAAAAAAAAAAAAAAJVAJBBBBBBVAAJBBVAAAAAAAJBHHJBWYJBBBW$YAJBWCZAAAAAAAAAD |
| 1EGO-15 | BBBBHPYJBVAAAAAAAAAAAAAAJVABBBBBBVAAABBHAAAAAAAJVPSBWCYJBBBW$YHBBPCYAAAAAAAAAA |
| 1EGO-16 | BBBBHHAABVAAAAAAAAAAAAAAAPSBBBBBBVAAAJBVAAAAAAAJBBVJWCYJBBBW$SBBBWCZAAAAAAADADD |
| 1EGO-17 | BBBBBHAAJVAAAAAAAAAAAAAAAJBBBBBBBVAAABBWYAAAAAAJVPSVAHVJBBBW$YHBBVJVAAAAAAAAAAA |
| 1EGO-18 | BBBBBHAAJVAAAAAAAAAAAAAAJVAJBBBBBBVAAABBBAAAAAAAJBWYAAJVJBBBW$YHBBPCZAAAAAAAAAA |
| 1EGO-19 | BBBBVHAJBVAAAAAAAAAAAAADAAPSBBBBBBBVAAABBBAAAAAAAJVJVJVPYABBBW$YABBVAAAAAAAAAAAD |
| 1EGO-20 | BBBBHPCSBAAAAAAAAAAAAAAAJVAJBBBBBBVAAJBBBAAAAAAAJVAJBVPYJBBBW$YAJBVAAAAAAAAAAAA |

1. The left column is the label for 20 conformers, and the top row shows the sequence (SEQ ID NO. 61).
2. The red color letters indicate the folding structures with identical assignment by PFSC for all 20 conformers.
3. The fragments are further marked with different colors; the conformers have the structural similarities marked with the same color in columns.

Discussion

The 27 PFSC vectors are obtained mathematically, and they are able to cover the enclosed space systematically. First, the PFSC possesses the general sense of shape object while they are well applied to protein folding description. The specific PFSC space zones and PFSC letters are relate to various types of protein secondary structures. The results show that overall agreement with structural assignment from other observed by various aspects of orientations. The vectors are associated each other by the horizontal layer, vertical slice or surrounding neighboring relation in FIG. 6. The association by 27 PFSC vectors provides the meaningful explanation for structural assignment.

Vector Characteristics of PFSC: The vector characteristics of the 27 PFSC are defined in FIG. 5, the features are summarized in Table I, and the integral relationship is exhibited in FIG. 6. Exception of the 27 PFSC letters, the vector characteristics from the PFSC can be expressed by an addition format of the PFSCV. The 27 PFSCV are able display how the vectors are coupled together for the structural assignment, which provide the detail structural information to analyze and compare protein structures.

Vector Coupling of PFSC: The protein structural assignments can be illustrated by the PFSC vector coupling. With structural assignments, two of the connected vectors share 4 $C_\alpha$ atoms, and each vector only left one $C_\alpha$ atom at each end different. The shared 4 $C_\alpha$ atoms at middle play a role as vector coupling. The structural assignment makes the vector connected one by one. However, the C-terminus of a vector must couple to the N-terminus of next vector. Furthermore, the connection of two vectors may incline coupling with appropriate folding shapes. The 27 PFSC folding shape patterns are able to be represented with the arrow lines as the vectors, and each end of arrow represent the N- or C-terminus. For example, the vectors "A" is for "α-α", "B" for "β-β", "J", for "α-β", "V" for "β-α", "P" for "α-*" and "C" for "*-*", and all 27 PFSC vectors can be obtained in FIG. 5. The folding shape character is attached at the end of arrow line. The regular secondary structures of α-helix or β-strand request same folding pattern extends to the next $C_\alpha$ atom in the protein backbone, so they expect the same folding features at two ends for the vectors. The vectors, "H", "A" and "D", have α-helical at both of the N- and C-termini, so they may be candidate for α-helix; the vectors, "E", "B" and "G", have α-strand at both of the N- and C-termini, so they may be candidate for β-strand. With appropriate pitch distance, the vector "A" is for typical α-helix and the vector "B" for typical β-strand. For smooth transition, the suitable coupling of two vectors prefers to share the same folding shapes character, i.e. formation of "-αα-", "-ββ-" or "-**-" between two of the connected vectors. Consequently, vector "V" prefers to use α-helical at C-terminus to connect to vector "A", but vector "J" prefers to use α-helical at N-terminus to connect to vector "A". If a rough coupling appears, such as "-α*-", "-β*-" or "-αβ-", the structural transition is abrupt. Also, the vector coupling can interprets the assignment capping secondary structures. It is apparently that the vector coupling offers an additional representation to understand the structural assignment. With the information provided by vector coupling, it is possible to identify the active site of protein, and to assist the protein and peptide structure design.

PFSC Vectors with Irregular Loops and Turns: In spite of having the complete description for protein structures, it is still hard to interpret how the irregular loops, coils and turns are formed. With 27 PFSC vectors, the irregular loops and turns may be formed by two factors. First, the irregular fragments are formed by some vectors with irregular folding character among 27 PFSC vectors, i.e. these vectors with "*" marked at the end of arrow in FIG. 5. There are 15 PFSC vectors have the irregular folding character "*", such as "X, R, F, L, O, Y, S, C, M, P, Z, T, $, N, Q". Especially, if these vectors are connected and appear on the structural assignment, they will create the irregular loop and coil, and turn. Second, the irregular fragments are also formed by a rough connection of any pair of PFSC vectors, even the vectors with α-helix and β-strand folding character. If two vectors do not couple with similar folding shape character, they will produce an abrupt transition during the connection, such as the vector "A" directly connects to the vector "B" by vector coupling "α-αβ-β"; the "V" uses the N-terminus to connect to the vector "A" by vector coupling "α-αβ-α", or the vector "J" uses the C-terminus to connect to the vector "A" by vector coupling "α-βα-α". Therefore, with 27 PFSC vectors, the irregular loops and the turns can be analyzed and traced.

In conclusion, the PFSC 27 vectors are not only the prototypes of folding patterns for the protein local structures, but also are the vectors with the explicit space orientation for protein folding descriptions. Also, the association of 27 PFSC vectors plays the significant role to reveal the protein folding structural assignments.

Number of Vectors

In this invention, the PFSC vectors are actually derived from a continuing and enclosed space, which initially has the infinite number of vectors. After partition of space, the 27 PFSC vectors are obtained, and each vector represents a specific folding shape pattern. In general, increasing the number of folding shape patterns may improve the folding description while it will complicate the analysis procedure. To modify the PFSC vector with including more $C_\alpha$ atoms or setting up more partition components would increase the number of folding shape patterns. For example, with same spatial partition mode, the vector with six, seven, or eight successive $C_\alpha$ atoms will have 81, 243 or 729 folding space patterns respectively. A simpler approach to obtain more folding patterns is to combine two consecutive the PFSC vectors. With PFSC strategy, two consecutive PFSC vectors with 6 successive $C_\alpha$ atoms will generate 729 folding motif patterns or vectors. In this mode, the total number of possible folding shape patterns will be $27^{(n-4)}$, where n is the total number of $C_\alpha$ atoms. To increase the number of folding shape patterns is possible, but it may not be necessary until the complication make a remarkable improvement. In this research, the PFSC 27 vectors have shown the significant results for protein folding structures.

Usage of Vectors

The PFSC method has been examined by protein structures from the SALIGN benchmark. The SALIGN benchmark is a test set of 200 pair wise proteins, which has an average pair sharing 20% sequence identity and 65% of structurally equivalent $C_\alpha$ atoms superposed with an rmsd of 3.5 Å. The frequencies of appearance of each PFSC vector for 268 protein chains from the SALIGN benchmark are summarized in FIG. 9. First, the observation coincides with the fact that the 27 vectors are designed to describe all possible folding shapes comprehensively, including the common and uncommon types of folding. Second, the 27 PFSC vectors are generated with equal weight, but their usages vary. The results show that most of 27 of vectors have being used for 268 protein chains. The data show that the vectors "A" and "B" for α-helix and β-strand have the highest numbers for appearance with number 38,274 and 20,361 individually. Overall, the both of α-helices and β-strands take about 67% of the local structural assignments. Three analogous vectors for secondary structures, "V", "J" and "H", are observed with higher numbers of appearance with number 7,176, 6,697 and 3,888 separately, and take about 21% of the local structural assignments. Also, four vectors, "W", "S", "Y" and "P", have higher numbers of appearance over 1000, and take about 9% of the local structural assignments. The eight vectors, "D", "Z", "C", "Q", "T", "$", "U" and "R", have numbers of appearance over 100. The numbers of appearance of vector "M" is zero, indicating without using. Other nine remaining vectors have very low frequencies. In summary, nine of among 27 vectors, "A", "B", "V", "J", "H", "W", "S", "Y" and "P", take about total 97% of the local structural assignments. It is not surprised that individual vector are not often adopted because of the limitations from the essence of protein structures, but all vectors are kept in place to reserve the enclosed space for seamless descriptions. The advantage is that any local structure of five consecutive C_□ atoms for over 46,000 proteins in the PDB should have an assignment with PFSC method.

The frequencies of appearance of 27 vectors in FIG. 9 are able to be explicitly mapped by FIG. 6. The vector "A" and "B" for α-helix and β-strand and three surrounding analogous vectors, "V", "J" and "H", have higher frequencies of appearance numbers for structural assignments. These five vectors are gathered at the top right corner in FIG. 6. Also, it is apparently that most vectors at the middle layer block and most vectors around "H", "A" and "D" have higher frequency of appearance. The distribution mapped in FIG. 6 reflects the nature of protein structures. In order words, most of local structural assignments are formed by the preference from the protein backbone, i.e. the hydrogen bond patterns and the 3D spatial restrictions etc.

Applications of PFSC

The PFSC method serves as a simplified tool to describe protein folding shapes. The PFSC method uses one dimensional alphabet letter string to illustrate the three-dimensional nature of the folding shapes. It is advantageous because, first, it is easy to trace and explore the irregular structures in proteins. Second, by aligning the PFSC with the linear amino acid sequence of the protein, it is possible to understand the folding shape of the protein in increments of 5 consecutive $C_\alpha$ atoms.

The PFSC method offers the seamless description of folding shapes from secondary to tertiary structures along protein $C_\alpha$ atom backbone. Also, any protein with given 3D structure is able to be described by PFSC.

The PFSC method is able to compare the protein 3D structure, and reveals the local and global similarity and dissimilarity. With folding structure alignment, the PFSC provides the score for comparison of similarity of group of proteins. Therefore, the PFSC result will improve the quality of selection of reference proteins or segments for protein structure prediction.

The PFSC method is able to assign all given 3-dimensional protein structures as one-dimensional string stored into a database. Furthermore, the correlation between 5 consecutive sequence and folding structural features is able to generate a universal database for genomics study of relationship between amino acid sequence and folding structures.

The protein folding shape code vector assignment (PFSCV) is a detail structural assignment with folding shape features and changes in protein. Based on the protein folding shapes along alpha-carbon atom backbone, the accessible protein surface code (APSC) is developed to assess the protein surface and cavity. To align the PFSCV with APSC as well as various properties of amino acids along protein backbone, it is able to predict the protein active sites, which is useful to assist the drug design, protein and peptide mutation, and to predict the protein interaction. Here are results of analysis of protein with PDB ID 1DOI. FIG. 10 shows that APSC of protein 1DOI. The FIG. 11 displays a snapshot of image of protein structure 1DOI. The residues on the surface are indicated by arrows. Table IX shows the alignment of Sequence, PFSC, PFSCV, APSC and Amino Acid Hydrophilic Properties for Fragment [50-75] of Protein 1DOI. The results indicate that unsmooth vector coupling β-α*-β on residues [59-60] and a pocket space around residue 59. Also properties of amino acids are aligned with the sequence. All these information together will assist the analysis and predict the active sites on protein.

TABLE IX

Alignment of Sequence, PFSC, PFSCV, APSC and Amino Acid Hydrophilic Properties for Fragment (50-75) of Protein 1 DOI

| | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 |
|---|---|---|---|---|---|---|---|---|---|---|---|---|---|---|---|---|---|---|---|---|---|---|---|---|---|---|
| SEQ ID NO. 62 | E | A | A | E | A | Q | G | Y | D | W | P | F | S | C | R | A | G | A | C | A | N | C | A | A | I | V |
| PFSC | A | A | A | A | A | D | J | B | B | W | S | B | V | J | V | H | H | A | A | H | A | J | B | B | B | B |
| PFSCA | α-αα-α | α-αα-α | α-αα-αα-ββ-β | | ββ-ββ-α*-ββ-β | | | | | | | β-αα-ββ-αα-αα-αα-αα-αα-αα-ββ-β | | | | | | | | | β-ββ-β | | | | β-β |
| APSC | 6 | 6 | 5 | 4 | 7 | 6 | 7 | 6 | 8 | 4 | 6 | 6 | 5 | 7 | 6 | 7 | 3 | 6 | 3 | 7 | 6 | 5 | 6 | 4 | 6 | 6 |
| Hydrophobic | – | X | X | – | X | – | – | – | – | X | X | X | – | X | – | X | – | X | X | X | – | X | X | X | X | X |

PFSC: protein folding shape code.
PFSCV: protein folding shape code vector assignment.
APSC: accessible protein surface code. The larger numbers indicate more accessible surface for protein for certain size of sphere. They are approximately divided as various regions by APSC. The numbers 9, 8 and 7 for protrusions; 6, 5 and 4 fro flat regions; 4, 3 and 2 for pockets; 1 and 0 for non accessible.
Here APSC is obtained by sphere with radius 7.0 A.

The PFSC method can be applied to the understanding of biological phenomena in which the folding of proteins structures is critical (Pietzsch, Protein Folding and Disease, Horizon Symposia, Nature Publishing Group, Oct. 3-5, 2002, which is hereby incorporated by reference). Diseases in which protein folding are in error can be divided into two major groups: (a) diseases related to excessive amounts of wrongly folded proteins, such as Alzheimer's disease, and (b) diseases related to incompletely folded proteins due to genetic errors, such as the p53 protein in cancer. The PFSC method can be applied to interpret experimental data from X-Ray crystallography or NMR spectroscopy to (1) offer an integrated viewing of different experiment data related to theses diseases, (2) detect the occurrence of protein misfolding related to these diseases, and (3) assist in the design of therapy to treat these diseases. Therefore, the PFSC method is useful in the understanding of the protein folding phenomenon in diseases, such as neurodegenerative diseases, metabolic diseases, inherited diseases, and diseases related with cancer and aging, etc.

According to the invention, the PFSC method can be applied to the study of the diseases related to protein folding/misfolding by creating a universal protein folding shape map ("UPFSM") as a platform to display the folding shape information of both individual proteins or a collection of proteins. The UPFSM can describe the complicated protein folding shape with simplicity, and to reveal the folding feature in detail. The UPFSM offers a unique and consistent approach to view various data. It will help to investigate all protein folding data for Alzheimer disease, and other diseases.

The UPFSM is composed of two components: the alignment component and the distribution component. The alignment component displays the PFSC along the protein sequence as a string of codes. Because the UPFSM interprets complicated three-dimensional structures into one-dimensional strings, the UPFSM simplifies the comparison of multiple conformers. In the traditional approach to the analysis of similar protein structures, including multiple conformers of the same protein, the different structures or conformers are compared by superimposing all the three-dimensional structures, and then measuring the value of root-mean-square deviation (RMSD). It is difficult to visualize how the structures are distinguished from each other. In contrast, the alignment component of the UPFSM offers a different approach to analyzing multiple structures and conformers. Because the alignment component aligns all the PFSC along the protein sequence, the UPFSM avoids artificially selecting the length and the location of segment to focus. In addition, by avoiding the confusion of superimposing data, the UPFSM enables the diagnosis for similarity or dissimilarity among structures and conformers in a simple and comprehensive manner. Therefore the alignment component of the UPSFM is a powerful tool for protein comparison and conformation analysis.

The distribution component of the UPFSM offers a new approach to analyze the conformations of proteins. The distribution component displays the protein sequence on a horizontal line and the 27 PFSC vectors on the vertical column. Given a particular protein structure, the distribution component will assign PFSC along the protein sequence. Therefore, distribution map converts the complicated three-dimensional folding shapes into relatively simple two-dimensional distribution map of PFSC. The distribution component is able to show an individual conformer, one set of conformers or multiple sets of proteins or conformers.

The UPFSM offers a new approach to analyze misfolding of alzheimer amyloid β-peptide (1-42) peptides. Amyloid is insoluble fibrous protein aggregation, and it plays a role to cause Alzheimer and other diseases. To better understand how the β-strand is formed inside the amyloid structure, various influential solvents or environments have been created around amyloid peptide, and the related folding structures have been accurately measured by NMR. It is not only difficult to describe the individual conformation of amyloid peptide, but also it is hard to compare the structures under same or different conditions. The structures of 1z0q are the results of 30 conformers in HFIP/H2O 30:70 (v/v) aqueous mixtures and the structures of 1iyt are the results of 10 conformers in HFIP/H2O 80:20 (v/v) aqueous mixtures. These 3D structures are determined by NMR. Here the UPFSM is demonstrated as a powerful tool to compare and analyze the folding structures. The detail illustration can be found in FIG. 12, FIG. 13 and FIG. 14. With UPSFM, the structural features of misfolding are displayed in FIG. 13 and FIG. 14. Also the difference of folding structures in different experiments is well revealed with using FIG. 13 and FIG. 14.

The invention claimed is:

1. A method for describing a structural conformation of a target protein sequence, the method comprising:
   (a) providing a 3D coordinate data set of a target protein sequence, wherein the target protein sequence is a consecutive sequence of amino acids, each amino acid comprises an alpha carbon, and the 3D coordinate data set comprises a coordinate of the alpha carbon of each amino acid;
   (b) dividing the target protein sequence into elements along the consecutive sequence of amino acids, wherein each element consists of five consecutive amino acids, the five consecutive amino acids consists of a first amino acid, a second amino acid, a third amino acid, a fourth amino acid, and a fifth amino acid, and when an element has a succeeding element, the second amino acid, the third amino acid, the fourth amino acid, and the fifth amino acid of the element are the first amino acid, the second amino acid, the third amino acid, and the fourth amino acid of the succeeding element, respectively;
   (c) extracting the coordinates of the alpha carbons of the first amino acid, the second amino acid, and the third amino acid of each element from the 3D coordinate data set to define a first plane of each element;
   (d) extracting the coordinates of the alpha carbons of the second amino acid, the third amino acid, and the fourth amino acid of each element from the 3D coordinate data set to define a second plane of each element;
   (e) calculating a first torsion angle of each element with respect to the first plane and the second plane, and determining a first range for each element within which the first torsion angle falls, wherein the first range is selected from a first range group consisting of range $a_1$, range $a_2$, and range $a_3$;
   (f) extracting the coordinates of the alpha carbons of the third amino acid, the fourth amino acid, and the fifth amino acid of each element from the 3D coordinate data set to define a third plane of each element;
   (g) calculating a second torsion angle of each element with respect to the second plane and the third plane, and determining a second range for each element within which the second torsion angle falls, wherein the second range is selected from a second range group consisting of range $b_1$, range $b_2$, and range $b_3$;

(h) based on the 3D coordinate data set, calculating a pitch distance of each element, and determining a third range for each element within which the pitch distance falls, wherein the pitch distance is a distance between the alpha carbon of the first amino acid and the alpha carbon of the fifth amino acid in each element, and the third range is selected from a third range group consisting of range $c_1$, range $c_2$, and range $c_3$;

(i) combining the first range, the second range, and the third range for each element obtained in (e), (g), and (h) to obtain a Protein Folding Shape Code vector for each element;

(j) designating each Protein Folding Shape Code vector obtained in (i) with a vector letter, wherein each vector letter is selected from 27 vector letters consisting of 26 alphabetic letters from "A" to "Z" and a sign "$;" and (k) arranging the vector letters obtained in (j) in an order in accordance with the consecutive sequence of amino acids to obtain a structural assignment document, wherein the structural assignment document is a description of the structural conformation of the target protein sequence.

2. The method of claim 1, wherein (j) is performed by:

when the Protein Folding Shape Code vector is a combination of the first range of $a_1$, the second range of $b_1$, and the third range of $c_1$, designating the Protein Folding Shape Code vector with a vector letter "D;"

when the Protein Folding Shape Code vector is a combination of the first range of $a_1$, the second range of $b_1$, and the third range of $c_2$, designating the Protein Folding Shape Code vector with a vector letter "A;"

when the Protein Folding Shape Code vector is a combination of the first range of $a_1$, the second range of $b_1$, and the third range of $c_3$, designating the Protein Folding Shape Code vector with a vector letter "H;"

when the Protein Folding Shape Code vector is a combination of the first range of $a_1$, the second range of $b_2$, and the third range of $c_1$, designating the Protein Folding Shape Code vector with a vector letter "W;"

when the Protein Folding Shape Code vector is a combination of the first range of $a_1$, the second range of $b_2$, and the third range of $c_2$, designating the Protein Folding Shape Code vector with a vector letter "V;"

when the Protein Folding Shape Code vector is a combination of the first range of $a_1$, the second range of $b_2$, and the third range of $c_3$, designating the Protein Folding Shape Code vector with a vector letter "U;"

when the Protein Folding Shape Code vector is a combination of the first range of $a_1$, the second range of $b_3$, and the third range of $c_1$, designating the Protein Folding Shape Code vector with a vector letter "Z;"

when the Protein Folding Shape Code vector is a combination of the first range of $a_1$, the second range of $b_3$, and the third range of $c_2$, designating the Protein Folding Shape Code vector with a vector letter "Y;"

when the Protein Folding Shape Code vector is a combination of the first range of $a_1$, the second range of $b_3$, and the third range of $c_3$, designating the Protein Folding Shape Code vector with a vector letter "X;"

when the Protein Folding Shape Code vector is a combination of the first range of $a_2$, the second range of $b_1$, and the third range of $c_1$, designating the Protein Folding Shape Code vector with a vector letter "K;"

when the Protein Folding Shape Code vector is a combination of the first range of $a_2$, the second range of $b_1$, and the third range of $c_2$, designating the Protein Folding Shape Code vector with a vector letter "J;"

when the Protein Folding Shape Code vector is a combination of the first range of $a_2$, the second range of $b_1$, and the third range of $c_3$, designating the Protein Folding Shape Code vector with a vector letter "I;"

when the Protein Folding Shape Code vector is a combination of the first range of $a_2$, the second range of $b_2$, and the third range of $c_1$, designating the Protein Folding Shape Code vector with a vector letter "G;"

when the Protein Folding Shape Code vector is a combination of the first range of $a_2$, the second range of $b_2$, and the third range of $c_2$, designating the Protein Folding Shape Code vector with a vector letter "B;"

when the Protein Folding Shape Code vector is a combination of the first range of $a_2$, the second range of $b_2$, and the third range of $c_3$, designating the Protein Folding Shape Code vector with a vector letter "E;"

when the Protein Folding Shape Code vector is a combination of the first range of $a_2$, the second range of $b_3$, and the third range of $c_1$, designating the Protein Folding Shape Code vector with a vector letter "T;"

when the Protein Folding Shape Code vector is a combination of the first range of $a_2$, the second range of $b_3$, and the third range of $c_2$, designating the Protein Folding Shape Code vector with a vector letter "S;"

when the Protein Folding Shape Code vector is a combination of the first range of $a_2$, the second range of $b_3$, and the third range of $c_3$, designating the Protein Folding Shape Code vector with a vector letter "R;"

when the Protein Folding Shape Code vector is a combination of the first range of $a_3$, the second range of $b_1$, and the third range of $c_1$, designating the Protein Folding Shape Code vector with a vector letter "Q;"

when the Protein Folding Shape Code vector is a combination of the first range of $a_3$, the second range of $b_1$, and the third range of $c_2$, designating the Protein Folding Shape Code vector with a vector letter "P;"

when the Protein Folding Shape Code vector is a combination of the first range of $a_3$, the second range of $b_1$, and the third range of $c_3$, designating the Protein Folding Shape Code vector with a vector letter "0;"

when the Protein Folding Shape Code vector is a combination of the first range of $a_3$, the second range of $b_2$, and the third range of $c_1$, designating the Protein Folding Shape Code vector with a vector letter "N;"

when the Protein Folding Shape Code vector is a combination of the first range of $a_3$, the second range of $b_2$, and the third range of $c_2$, designating the Protein Folding Shape Code vector with a vector letter "M;"

when the Protein Folding Shape Code vector is a combination of the first range of $a_3$, the second range of $b_2$, and the third range of $c_3$, designating the Protein Folding Shape Code vector with a vector letter "L;"

when the Protein Folding Shape Code vector is a combination of the first range of $a_3$, the second range of $b_3$, and the third range of $c_1$, designating the Protein Folding Shape Code vector with a vector letter "$;"

when the Protein Folding Shape Code vector is a combination of the first range of $a_3$, the second range of $b_3$, and the third range of $c_2$, designating the Protein Folding Shape Code vector with a vector letter "C;" and when the Protein Folding Shape Code vector is a combination of the first range of $a_3$, the second range of $b_3$, and the third range of $c_3$, designating the Protein Folding Shape Code vector with a vector letter "F."

3. The method of claim 1, wherein the target protein sequence comprises an N-terminus and a C-terminus, and (a)

further comprises arranging the coordinates of the alpha carbons in an order of from the N-terminus to the C-terminus.

4. The method of claim 1, wherein:
the range $a_1$ ranges from 0° to 160°;
the range $a_2$ ranges from +120° to −120°; and
the range $a_3$ ranges from −160° to 0°.

5. The method of claim 1, wherein:
the range $a_1$ ranges from 0° to 130°;
the range $a_2$ ranges from 130° to 180° and from −180° to −130°; and
the range $a_3$ ranges from −130° to 0°.

6. The method of claim 1, wherein:
the range $b_1$ ranges from 0° to 160°;
the range $b_2$ ranges from +120° to −120°; and
the range $b_3$ ranges from −160° to 0°.

7. The method of claim 1, wherein:
the range $b_1$ ranges from 0° to 130°;
the range $b_2$ ranges from 130° to 180° and from −180° to −130°; and
the range $b_3$ ranges from −130° to 0°.

8. The method of claim 1, wherein:
the range $c_1$ ranges from zero to 7.0 Å;
the range $c_2$ ranges from 4.0 Å to 17.0 Å; and
the range $c_3$ is greater than 12.01.

9. The method of claim 1, wherein:
the range $c_1$ ranges from zero to 5.5 Å;
the range $c_2$ ranges from 5.5 Å to 14.0 Å; and
the range $c_3$ is greater than 14.01.

10. The method of claim 1, wherein (a) further comprises obtaining the 3D coordinate data set from a protein structure database, the protein structure database being selected from Protein Data Bank, WWPDB, RCSB PDB, MSD-EBI, PDBj, BMRB, and NCBI MMDB.

11. A computer-assisted method for describing a folding conformation of a target protein sequence, the method comprising:
(a) selecting a 3D coordinate data set of a target protein sequence from a protein structure database, wherein the target protein sequence is a consecutive sequence of amino acids, each amino acid comprises an alpha carbon, and the 3D coordinate data set comprises a coordinate of the alpha carbon of each amino acid;
(b) inputting the 3D coordinate data set selected in (a) into a computer;
(c) executing an element-dividing program stored in the computer to divide the target protein sequence into elements along the consecutive sequence of amino acids, wherein each element consists of five consecutive amino acids, the five consecutive amino acids consists of a first amino acid, a second amino acid, a third amino acid, a fourth amino acid, and a fifth amino acid, and when an element has a succeeding element, the second amino acid, the third amino acid, the fourth amino acid, and the fifth amino acid of the element are the first amino acid, the second amino acid, the third amino acid, and the fourth amino acid of the succeeding element, respectively;
(d) executing an alpha carbon-identifying program stored in the computer to extract coordinates of the alpha carbons of each element from the 3D coordinate data set;
(e) executing a plane-defining program stored in the computer to define a first plane of each element according to the coordinates of the alpha carbons of the first amino acid, the second amino acid, and the third amino acid of each element;
(f) executing the plane-defining program to define a second plane of each element according to the coordinates of the alpha carbons of the second amino acid, the third amino acid, and the fourth amino acid of each element;
(g) executing the plane-defining program to define a third plane of each element according to the coordinates of the alpha carbons of the third amino acid, the fourth amino acid, and the fifth amino acid of each element;
(h) executing a torsion angle-calculating program stored in the computer to calculate a first torsion angle of each element with respect to the first plane and the second plane of each element, and to calculate a second torsion angle of each element with respect to the second plane and the third plane of each element;
(i) executing a distance-calculating program stored in the computer to calculate a pitch distance of each element, wherein the pitch distance is a distance between the alpha carbon of the first amino acid and the alpha carbon of the fifth amino acid in each element;
(j) executing a range-identifying program stored in the computer to identify a range of the first torsion angle, a range of the second torsion angle, and a range of the pitch distance for each element, wherein the range of the first torsion angle is a member selected from a first range group consisting of $a_1$, $a_2$, and $a_3$, the range of the second torsion angle is a member selected from a second range group consisting of $b_1$, $b_2$, and $b_3$, and the range of the pitch distance is a member selected from a third range group consisting of $c_1$, $c_2$, and $c_3$;
(k) executing a vector-assigning program stored in the computer to combine the range of the first torsion angle, the range of the second range angle, and the range of the pitch distance of each element obtained in (j) to obtain a Protein Folding Shape Code vector for each element;
(l) executing the vector-assigning program to designate each Protein Folding Shape Code vector obtained in (k) with a vector letter; and
(m) executing an outputting program stored in the computer to arrange the vector letters obtained in (1) in an order in accordance with the consecutive sequence of amino acids to obtain a structural assignment document for data output, wherein the structural assignment document is a description of the folding conformation of the target protein sequence.

12. The method of claim 11, wherein (1) is performed by:
executing the vector-assigning program to designate the Protein Folding Shape Code vector with a vector letter "D" when the Protein Folding Shape Code vector is a combination of the range of the first torsion angle of $a_1$, the range of the second torsion angle of $b_1$, and the range of the pitch distance of $c_1$;
executing the vector-assigning program to designate the Protein Folding Shape Code vector with a vector letter "A" when the Protein Folding Shape Code vector is a combination of the range of the first torsion angle of $a_1$, the range of the second torsion angle of $b_1$, and the range of the pitch distance of $c_2$;
executing the vector-assigning program to designate the Protein Folding Shape Code vector with a vector letter "H" when the Protein Folding Shape Code vector is a combination of the range of the first torsion angle of $a_1$, the range of the second torsion angle of $b_1$, and the range of the pitch distance of $c_3$;
executing the vector-assigning program to designate the Protein Folding Shape Code vector with a vector letter "W" when the Protein Folding Shape Code vector is a combination of the range of the first torsion angle of $a_1$, the range of the second torsion angle of $b_2$, and the range of the pitch distance of $c_1$;

executing the vector-assigning program to designate the Protein Folding Shape Code vector with a vector letter "V" when the Protein Folding Shape Code vector is a combination of the range of the first torsion angle of $a_1$, the range of the second torsion angle of $b_2$, and the range of the pitch distance of $c_2$;

executing the vector-assigning program to designate the Protein Folding Shape Code vector with a vector letter "U" when the Protein Folding Shape Code vector is a combination of the range of the first torsion angle of $a_1$, the range of the second torsion angle of $b_2$, and the range of the pitch distance of $c_3$;

executing the vector-assigning program to designate the Protein Folding Shape Code vector with a vector letter "Z" when the Protein Folding Shape Code vector is a combination of the range of the first torsion angle of $a_1$, the range of the second torsion angle of $b_3$, and the range of the pitch distance of $c_1$;

executing the vector-assigning program to designate the Protein Folding Shape Code vector with a vector letter "Y" when the Protein Folding Shape Code vector is a combination of the range of the first torsion angle of $a_1$, the range of the second torsion angle of $b_3$, and the range of the pitch distance of $c_2$;

executing the vector-assigning program to designate the Protein Folding Shape Code vector with a vector letter "X" when the Protein Folding Shape Code vector is a combination of the range of the first torsion angle of $a_1$, the range of the second torsion angle of $b_3$, and the range of the pitch distance of $c_3$;

executing the vector-assigning program to designate the Protein Folding Shape Code vector with a vector letter "K" when the Protein Folding Shape Code vector is a combination of the range of the first torsion angle of $a_2$, the range of the second torsion angle of $b_1$, and the range of the pitch distance of $c_1$;

executing the vector-assigning program to designate the Protein Folding Shape Code vector with a vector letter "J" when the Protein Folding Shape Code vector is a combination of the range of the first torsion angle of $a_2$, the range of the second torsion angle of $b_1$, and the range of the pitch distance of $c_2$;

executing the vector-assigning program to designate the Protein Folding Shape Code vector with a vector letter "I" when the Protein Folding Shape Code vector is a combination of the range of the first torsion angle of $a_2$, the range of the second torsion angle of $b_1$, and the range of the pitch distance of $c_3$;

executing the vector-assigning program to designate the Protein Folding Shape Code vector with a vector letter "G" when the Protein Folding Shape Code vector is a combination of the range of the first torsion angle of $a_2$, the range of the second torsion angle of $b_2$, and the range of the pitch distance of $c_1$;

executing the vector-assigning program to designate the Protein Folding Shape Code vector with a vector letter "B" when the Protein Folding Shape Code vector is a combination of the range of the first torsion angle of $a_2$, the range of the second torsion angle of $b_2$, and the range of the pitch distance of $c_2$;

executing the vector-assigning program to designate the Protein Folding Shape Code vector with a vector letter "E" when the Protein Folding Shape Code vector is a combination of the range of the first torsion angle of $a_2$, the range of the second torsion angle of $b_2$, and the range of the pitch distance of $c_3$;

executing the vector-assigning program to designate the Protein Folding Shape Code vector with a vector letter "T" when the Protein Folding Shape Code vector is a combination of the range of the first torsion angle of $a_2$, the range of the second torsion angle of $b_3$, and the range of the pitch distance of $c_1$;

executing the vector-assigning program to designate the Protein Folding Shape Code vector with a vector letter "S" when the Protein Folding Shape Code vector is a combination of the range of the first torsion angle of $a_2$, the range of the second torsion angle of $b_3$, and the range of the pitch distance of $c_2$;

executing the vector-assigning program to designate the Protein Folding Shape Code vector with a vector letter "R" when the Protein Folding Shape Code vector is a combination of the range of the first torsion angle of $a_2$, the range of the second torsion angle of $b_3$, and the range of the pitch distance of $c_3$;

executing the vector-assigning program to designate the Protein Folding Shape Code vector with a vector letter "Q" when the Protein Folding Shape Code vector is a combination of the range of the first torsion angle of $a_3$, the range of the second torsion angle of $b_1$, and the range of the pitch distance of $c_1$;

executing the vector-assigning program to designate the Protein Folding Shape Code vector with a vector letter "P" when the Protein Folding Shape Code vector is a combination of the range of the first torsion angle of $a_3$, the range of the second torsion angle of $b_1$, and the range of the pitch distance of $c_2$;

executing the vector-assigning program to designate the Protein Folding Shape Code vector with a vector letter "0" when the Protein Folding Shape Code vector is a combination of the range of the first torsion angle of $a_3$, the range of the second torsion angle of $b_1$, and the range of the pitch distance of $c_3$;

executing the vector-assigning program to designate the Protein Folding Shape Code vector with a vector letter "N" when the Protein Folding Shape Code vector is a combination of the range of the first torsion angle of $a_3$, the range of the second torsion angle of $b_2$, and the range of the pitch distance of $c_1$;

executing the vector-assigning program to designate the Protein Folding Shape Code vector with a vector letter "M" when the Protein Folding Shape Code vector is a combination of the range of the first torsion angle of $a_3$, the range of the second torsion angle of $b_2$, and the range of the pitch distance of $c_2$;

executing the vector-assigning program to designate the Protein Folding Shape Code vector with a vector letter "L" when the Protein Folding Shape Code vector is a combination of the range of the first torsion angle of $a_3$, the range of the second torsion angle of $b_2$, and the range of the pitch distance of $c_3$;

executing the vector-assigning program to designate the Protein Folding Shape Code vector with a vector letter "$" when the Protein Folding Shape Code vector is a combination of the range of the first torsion angle of $a_3$, the range of the second torsion angle of $b_3$, and the range of the pitch distance of $c_1$;

executing the vector-assigning program to designate the Protein Folding Shape Code vector with a vector letter "C" when the Protein Folding Shape Code vector is a combination of the range of the first torsion angle of $a_3$, the range of the second torsion angle of $b_3$, and the range of the pitch distance of $c_2$; and executing the vector-assigning program to designate the Protein Folding Shape Code vector with a vector letter "F" when the Protein Folding Shape Code vector is a combination of the range of the first torsion angle of $a_3$, the range of the second torsion angle of $b_3$, and the range of the pitch distance of $c_3$.

13. The method of claim 11, wherein the target protein sequence comprises an N-terminus and a C-terminus, and (c) further comprises executing the element-dividing program to arrange the coordinates of the alpha carbons in an order of from the N-terminus to the C-terminus.

14. The method of claim 11, wherein:

the range $a_1$ ranges from 0° to 160°;

the range $a_2$ ranges from +120° to −120°; and the range $a_3$ ranges from −160° to 0°.

15. The method of claim 11, wherein:

the range $a_1$ ranges from 0° to 130°;

the range $a_2$ ranges from 130° to 180° and from −180° to −130°; and the range $a_3$ ranges from −130° to 0°.

16. The method of claim 11, wherein:

the range $b_1$ ranges from 0° to 160°;

the range $b_2$ ranges from +120° to −120°; and the range $b_3$ ranges from −160° to 0°.

17. The method of claim 11, wherein:

the range $b_1$ ranges from 0° to 130°;

the range $b_2$ ranges from 130° to 180° and from −180° to −130°; and the range $b_3$ ranges from −130° to 0°.

18. The method of claim 11, wherein:

the range $c_1$ ranges from zero to 7.0 Å;

the range $c_2$ ranges from 4.0 Å to 17.0 Å; and the range $c_3$ is greater than 12.01.

19. The method of claim 11, wherein:

the range $c_1$ ranges from zero to 5.5 Å;

the range $c_2$ ranges from 5.5 Å to 14.0 Å; and the range $c_3$ is greater than 14.01.

20. The method of claim 11, wherein (a) further comprises selecting the protein structure database from Protein Data Bank, WWPDB, RCSB PDB, MSD-EBI, PDBj, BMRB, and NCBI MMDB.

* * * * *